United States Patent
Hong et al.

(10) Patent No.: US 12,344,618 B2
(45) Date of Patent: *Jul. 1, 2025

(54) HETEROTRICYCLIC DERIVATIVE COMPOUND AND USE OF SAME

(71) Applicant: HANMI PHARMACEUTICAL CO., LTD., Hwaseong-si (KR)

(72) Inventors: Dong Jin Hong, Hwaseong-si (KR); Seung Hyun Jung, Hwaseong-si (KR); Chang Hee Park, Hwaseong-si (KR); Seo Hee Kim, Hwaseong-si (KR); Ji Young Hwang, Hwaseong-si (KR); Young Gil Ahn, Hwaseong-si (KR)

(73) Assignee: HANMI PHARMACEUTICAL CO., LTD., Hwaseong-si (KR)

( * ) Notice: Subject to any disclaimer, the term of this patent is extended or adjusted under 35 U.S.C. 154(b) by 729 days.

This patent is subject to a terminal disclaimer.

(21) Appl. No.: 17/431,933

(22) PCT Filed: Feb. 19, 2020

(86) PCT No.: PCT/KR2020/002427
§ 371 (c)(1),
(2) Date: Aug. 18, 2021

(87) PCT Pub. No.: WO2020/171606
PCT Pub. Date: Aug. 27, 2020

(65) Prior Publication Data
US 2022/0135582 A1 May 5, 2022

(30) Foreign Application Priority Data
Feb. 19, 2019 (KR) .................. 10-2019-0019544

(51) Int. Cl.
C07D 491/056 (2006.01)
(52) U.S. Cl.
CPC ................. C07D 491/056 (2013.01)
(58) Field of Classification Search
CPC .............. C07D 491/04; C07D 491/056; A61K 31/4743; A61P 35/00
See application file for complete search history.

(56) References Cited

U.S. PATENT DOCUMENTS

| 11,535,629 | B2* | 12/2022 | Jung | ............... A61P 35/00 |
| 2014/0179667 | A1 | 6/2014 | Edwards et al. | |
| 2015/0361067 | A1 | 12/2015 | Collins et al. | |
| 2021/0206776 | A1* | 7/2021 | Côté | ............... A61P 35/00 |
| 2022/0135582 | A1 | 5/2022 | Hong et al. | |

FOREIGN PATENT DOCUMENTS

| EP | 3 929 199 A1 | 12/2021 |
| JP | 7358491 B2 | 10/2023 |
| KR | 10-2015-0100823 A | 9/2015 |
| KR | 10-2016-0132391 A | 11/2016 |
| KR | 10-2017-0016493 A | 2/2017 |
| WO | 2012/142504 A1 | 10/2012 |
| WO | 2013/067302 A1 | 5/2013 |
| WO | 2014097041 A1 | 6/2014 |
| WO | 2015/077194 A1 | 5/2015 |
| WO | 2015/141616 A1 | 9/2015 |
| WO | 2015193765 A1 | 12/2015 |
| WO | 2019/204490 A1 | 10/2019 |
| WO | 2019226491 A1 | 11/2019 |
| WO | 2020/171606 A1 | 8/2020 |

OTHER PUBLICATIONS

Boothroyd, S.; et al. "Why Do Some Molecules Form Hydrates or Solvates?" 2018 Crystal Growth and Design, vol. 18, pp. 1903-1908. (Year: 2018).*
Weers, J. G.; Miller, D. P. "Formulation Design of Dry Powders for Inhalation" 2015, Journal of Pharmaceutical Sciences, vol. 104, pp. 3259-3288. (Year: 2015).*
Perola, E. "An Analysis of the Binding Efficiencies of Drugs and Their Leads in Successful Drug Discovery Programs" 2010, Journal of Medicinal Chemistry, vol. 63, pp. 2986-2997. (Year: 2010).*
S. Fujita, et al., "Dual inhibition of EZH1/2 breaks the quiescence of leukemia stem cells in acute myeloid leukemia", Leukemia, 2018, vol. 32, pp. 855-864 (21 pages).
Communication dated Dec. 12, 2023, issued in European Application No. 20 759 257.7.
Written Opinion dated May 24, 2022 from the Intellectual Property Office of Singapore in Application No. 11202108940R.

(Continued)

*Primary Examiner* — Eric Olson
*Assistant Examiner* — Benjamin M Brandsen
(74) *Attorney, Agent, or Firm* — Sughrue Mion, PLLC

(57) ABSTRACT

A novel heterotricyclic compounds of Formula 1 or pharmaceutically acceptable salts thereof, and uses thereof are disclosed. The novel heterotricyclic compounds exhibit an inhibitory activity against EZH1 (enhancer of zeste homolog 1) and/or EZH2 (enhancer of zeste homolog 2) activity. Pharmaceutical compositions containing these compounds as active ingredient is also disclosed. The heterotricyclic compound, pharmaceutically acceptable salts thereof, or compositions containing the compound or salt are useful in treating tumor or cancer in a subject.

Formula 1

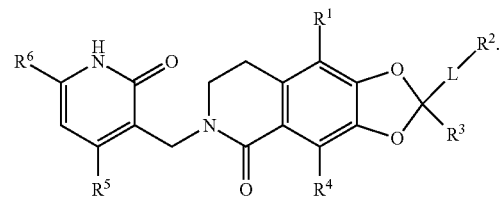

12 Claims, No Drawings

(56) References Cited

OTHER PUBLICATIONS

Search Report dated May 24, 2022 from the Intellectual Property Office of Singapore in Application No. 11202108940R.
Pei-Pei Kung et al., "Design and Synthesis of Pyridone-Containing 3,4-Dihydroisoquinoline-1(2H)-ones as a Novel Class of Enhancer of Zeste Homolog 2 (EZH2) Inhibitors", Journal of Medical Chemistry, 2016, pp. 8306-8325, vol. 59.
International Search Report for PCT/KR2020/002427, dated Jun. 9, 2020.

* cited by examiner

HETEROTRICYCLIC DERIVATIVE COMPOUND AND USE OF SAME

CROSS REFERENCE TO RELATED APPLICATIONS

This application is a National Stage of Application No. PCT/KR2020/002427 filed Feb. 19, 2020, claiming priority based on Korean Patent Application No. 10-2019-0019544 filed Feb. 19, 2019.

TECHNICAL FIELD

The present disclosure relates to novel heterotricyclic derivative compounds and the use thereof, and more particularly, to novel heterotricyclic derivative compounds having inhibitory activity against EZH1 (enhancer of zeste homolog 1) and/or EZH2 (enhancer of zeste homolog 2) activity, pharmaceutically acceptable salts thereof, or pharmaceutical compositions containing these compounds.

BACKGROUND ART

Chromosomes dynamically control gene replication or transcription by changing their higher-order structures through methylation of their constituent DNA or various modifications (acetylation, methylation, phosphorylation, ubiquitination, etc.) of histones (histones H2A, H2B, H3 and H4).

In general, trimethylation of lysine at the 4$^{th}$ position from the N-terminus of histone H3 (H3K4me3) functions to activate transcription, whereas trimethylation of lysine at the 27$^{th}$ position (H3K27me3) functions to inhibit transcription. The former and latter trimethylations are performed by a trithorax complex and Polycomb repressive complex 2 (PRC2), respectively (*Cell* 2007, 128, 735-745; *Nat. Rev. Cancer* 2010, 10, 669-682).

The Polycomb gene group was identified as a gene controlling the embryogenesis of *Drosophila* and is also conserved in vertebrates (*Nat. Rev. Genet.* 2007, 8, 9-22). In *Drosophila*, the enhancer of zeste protein is a catalytic subunit responsible for the H3K27 methylation of PRC2. Both EZH1 (enhancer of zeste homolog 1 (*Drosophila*)) and EZH2 (enhancer of zeste homolog 2 (*Drosophila*)) are mammalian homologs of the *Drosophila* enhancer of zeste (*EMBO J.* 1997, 16, 3219-3232; *Mamm. Genome.* 1999, 10, 311-314). The enzyme activity domains (SET domains) of EZH1 and EZH2 have high homology. In humans or mice, two types of PRC2 (PRC2-EZH1 and PRC2-EZH2) exist which contain EZH1 or EZH2 as a catalytic subunit (*Mol. Cell* 2008, 32, 491-502; *Mol. Cell* 2008, 32, 503-518).

In ES cells, EZH1 and EZH2 function cooperatively or complementarily, and are involved in the maintenance of ES cells (*Mol. Cell* 2008, 32, 491-502). In addition, it has been reported that EZH1 and EZH2 also cooperatively act on the formation and maintenance of hair follicles or the differentiation of Merkel cells, and both are also critical to the maintenance of hematopoietic stem cells (*Genes Dev.* 2011, 25, 485-498; *EMBO J.* 2013, 32, 1990-2000; *Blood* 2011, 118, 6553-6561; *Cell Stem Cell* 2012, 11, 649-662; *Cell Stem Cell* 2014, 14, 68-80).

Until now, increased expression of EZH2 has been reported in a number of cancers including prostate cancer, breast cancer, stomach cancer, lung cancer, ovarian cancer, pancreatic cancer, kidney cancer, and head and neck cancer, and it has also been reported that the poor prognosis in some of these cancers correlates with increased expression of EZH2 (*Nature* 2002, 419, 624-629; *Proc. Natl. Acad. Sci. USA* 2003, 100, 11606-11611; *Asian Pac. J. Cancer Prev.* 2012, 13, 3173-3178; *Clin, Cancer Res.* 2013, 19, 6556-6565; *Cancer Cell* 2010, 18, 185-197; *Hum. Pathol.* 2010, 41, 1205-1209; *BMC Cancer* 2010, 10, 524; *Cancer* 2012, 118, 2858-2871; *Mutat. Res.* 2008, 647, 21-29). There is also a report indicating that EZH2 knockdown in cell lines derived from these cancers inhibits cell growth ((*Nature* 2002, 419, 624-629; *Oncogene* 2009, 28, 843-853). In addition, when EZH2 is overexpressed in non-cancerous cell lines of the epithelial system, characteristic phenotypes of cancer appears, such as invasiveness or enhanced cell proliferation in a soft agar medium (*Proc. Natl. Acad. Sci. USA* 2003, 100, 11606-11611).

It has been reported that, in follicular lymphoma (FL) or follicular center B cell-type diffuse large B-cell lymphoma (DLBCL), somatic mutations are found at tyrosine 641, alanine 677, and alanine 687 (Y641F, Y641N, Y641S, Y641H, Y641C, A677G, and A687V) of EZH2, and due to these mutations, the function of EZH2 is enhanced, and thus the H3K27me3 modification level in the cell significantly increases (*Nat. Genet.* 2010, 42, 181-185; *FEBS Lett.* 2011, 585, 3011-3014; *Proc. Natl. Acad. Sci. USA* 2012, 109, 2989-2994; *FEBS Lett.* 2012, 586, 3448-3451). Compounds that specifically inhibit the enzymatic activity of EZH2 inhibit, both in vitro and in vivo (xenograft model), the growth of a cancer cell line having this somatic mutation in EZH2 (*Nature* 2012, 492, 108-112; *Nat. Chem. Biol.* 2012, 8, 890-896).

These facts suggest that knockdown of EZH2 or inhibition of the enzymatic activity thereof is useful for the treatment of cancer having increased expression of EZH2 or a somatic mutation in EZH2.

Although there is a lot of knowledge about cellular carcinogenesis induced by EZH2, little analysis has yet been done on the relationship between EZH1 and cellular carcinogenesis. However, it has recently been found that general inhibition of PRC2 suppresses the progression of acute myeloid leukemia (AML) caused by a MLL-AF9 fusion gene, but inhibition of EZH2 alone is not sufficient for this suppression (*Proc. Natl. Acad. Sci. USA* 2012, 109, 5028-5033). This means that inhibition of PRC2-EZH2 alone is insufficient for suppressing acute myeloid leukemia caused by the MLL-AF9 fusion gene, and that simultaneous inhibition of PRC2-EZH1 and PRC2-EZH2 is necessary for this suppression.

The present inventors have conducted studies on compounds of the above-described concept, and as a result, have found that novel heterotricyclic derivative compounds have inhibitory activity against EZH1 and/or EZH2, thereby completing the present disclosure.

DISCLOSURE

Technical Problem

An object of the present disclosure is to provide a novel heterotricyclic derivative compound having excellent inhibitory activity against EZH1 and/or EZH2.

Another object of the present disclosure is to provide a pharmaceutical composition containing a therapeutically effective amount of the compound.

Technical Solution

In accordance with an embodiment of the present disclosure, there is provided a compound selected from among a heterotricyclic derivative compound of the following Formula 1, a pharmaceutically acceptable salt thereof, an optical isomer thereof, a hydrate thereof, and a solvate thereof:

[Formula 1]

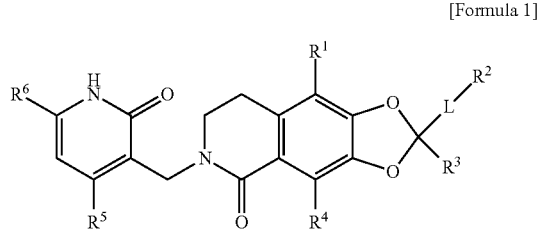

wherein:
- $R^1$ is H, a halogen, cyano, a $C_{1-6}$ alkyl containing 0 to 3 halogen atoms, a $C_{1-6}$ alkoxy containing 0 to 3 halogen atoms, $C_{3-6}$ cycloalkyl, $C_{1-6}$ alkylcarbonyl, $C_{2-6}$ alkenyl, $C_{2-6}$ alkynyl, $C_{3-6}$ cycloalkenyl, aryl, a 5- to 6-membered aromatic heterocyclyl containing 1 to 3 heteroatoms independently selected from the group consisting of N, O and S in a ring thereof, or a 5- to 6-membered aliphatic heterocyclyl containing 1 or 2 heteroatoms independently selected from the group consisting of N, O and S in a ring thereof and containing or not containing an unsaturated bond in a part of the ring thereof,
the $C_{3-6}$ cycloalkyl, the aryl, the 5- to 6-membered aromatic heterocyclyl containing 1 to 3 heteroatoms independently selected from the group consisting of N, O and S in the ring thereof, or the 5- to 6-membered aliphatic heterocyclyl containing 1 or 2 heteroatoms independently selected from the group consisting of N, O and S in a ring thereof and containing or not containing an unsaturated bond in a part of the ring thereof is unsubstituted or substituted with one to three independently selected from Group A below;
L is a bond, $C_{1-6}$ alkylene, or oxy($C_{1-6}$)alkylene;
$R^2$ is H, $C_{1-6}$ alkyl, $C_{3-6}$ cycloalkyl, a 5- to 6-membered aliphatic heterocyclyl containing 1 or 2 heteroatoms independently selected from the group consisting of N, O and S in a ring thereof, aryl, a 5- to 6-membered aromatic heterocyclyl containing 1 to 3 heteroatoms independently selected from the group consisting of N, O and S in a ring thereof, or 5- to 12-membered bicyclic heteroaryl;
the $C_{1-6}$ alkyl, the $C_{3-6}$ cycloalkyl, the 5- to 6-membered aliphatic heterocyclyl, the aryl, the 5- to 6-membered aromatic heterocyclyl, or the 5- to 12-membered bicyclic heteroaryl is unsubstituted or substituted with one or three independently selected from Group C below;
$R^3$ is $C_{1-6}$ alkyl;
$R^4$ is H, a halogen, or a $C_{1-6}$ alkyl containing 0 to 3 halogen atoms;
$R^5$ is $C_{1-6}$ alkyl or $C_{1-6}$ alkoxy;
$R^6$ is $C_{1-6}$ alkyl;
Group A is a halogen, $C_{1-6}$ alkyl, $C_{1-6}$ alkoxy, or a 5 to 6-membered aliphatic heterocyclyl containing 1 or 2 heteroatoms independently selected from the group consisting of N, O and S in a ring thereof, wherein the $C_{1-6}$ alkyl, the $C_{1-6}$ alkoxy and the 5 to 6-membered aliphatic heterocyclyl are unsubstituted or substituted with one to three independently selected from Group B below;
Group B is a halogen, $C_{1-6}$ alkyl, or a 5 to 6-membered aliphatic heterocyclyl containing 1 or 2 heteroatoms independently selected from the group consisting of N, O and S in a ring thereof; and
Group C is hydroxy, formyl, a $C_{1-6}$ alkyl substituted with 0 to 3 halogen atoms, substituted or unsubstituted $C_{1-6}$ alkylcarbonyl, $C_{1-6}$ alkoxy, $C_{1-6}$ alkylsulfonyl, —$NR^{20}R^{21}$, ($C_{1-6}$)alkoxy($C_{1-6}$)alkyl, di($C_{1-6}$)alkylamino($C_{1-6}$)alkyl, or a 4- to 6-membered aliphatic heterocyclyl containing 1 to 2 heteroatoms independently selected from the group consisting of N, O and S in a ring thereof, wherein $R^{20}$ and $R^{21}$ are each independently H, formyl, $C_{1-6}$ alkyl, or substituted or unsubstituted $C_{1-6}$ alkylcarbonyl.

In accordance with another embodiment of the present disclosure, there is provided a pharmaceutical composition and a pharmaceutical preparation for preventing or treating various diseases associated with EZH1 and/or EZH2, the pharmaceutical composition and the pharmaceutical preparation containing a therapeutically effective amount of the compound.

The heterotricyclic derivative compound represented by Formula 1, which provided in the present disclosure, has excellent inhibitory activity against EZH1 and/or EZH2, and thus has anticancer activity against cancer associated with the activity of EZH1, EZH2 or both EZH1 and EZH2, and may be effectively used as a therapeutic agent against the cancer.

Advantageous Effects

The heterotricyclic derivative compound represented by Formula 1, which provided in the present disclosure, has excellent inhibitory activity against EZH1 and/or EZH2, and thus has anticancer activity against cancer associated with the activity of EZH1, EZH2 or both EZH1 and EZH2, and may be effectively used as a therapeutic agent against the cancer.

MODE FOR INVENTION

The definitions listed below are definitions of various terms used to describe the present disclosure. These definitions apply throughout this specification, individually or as part of terms covering them, unless otherwise limited.

As used herein, the term "halogen" refers to fluorine, chlorine, bromine or iodine, unless otherwise stated.

As used herein, the term "hydroxyl" refers to a —OH group, unless otherwise stated.

As used herein, the term "alkyl" refers to saturated linear or branched hydrocarbon radicals represented by $C_nH_{2n+1}$, unless otherwise stated. Specifically, the term "alkyl" refers to saturated linear or branched hydrocarbon radicals, each containing 1 to 6, 1 to 8, 1 to 10, or 1 to 20 carbon atoms. Examples of these radicals include, but are not limited to, methyl, ethyl, propyl, isopropyl, n-butyl, t-butyl, neopentyl, n-hexyl, heptyl, and octyl radicals. For example, the term "$C_{1-6}$ alkyl" as used herein refers to a linear or branched hydrocarbon radical having 1 to 6 carbon atoms, unless otherwise specified. Examples thereof include, but are not limited to, methyl, ethyl, propyl, isopropyl, n-butyl, sec-butyl, t-butyl, n-pentyl, n-hexyl, and the like.

The term "alkenyl" as used herein, unless otherwise stated, refers to a monovalent group derived from an unsaturated linear or branched hydrocarbon moiety having at least one carbon-carbon double bond. Specifically, the term "alkenyl" refers to unsaturated linear or branched monovalent radicals, each containing 2 to 6, 2 to 8, 2 to 10, or 2 to 20 carbon atoms. Examples thereof include, but are not limited to, ethenyl, propenyl, butenyl, 1-methyl-2-buten-1-yl, heptenyl, and octenyl radicals.

The term "alkynyl" as used herein, unless otherwise stated, refers to a monovalent group derived from an unsaturated linear or branched hydrocarbon moiety having at least one carbon-carbon triple bond.

The term "alkoxy" as used herein, unless otherwise stated, refers to a monovalent oxygen radical represented by $OC_nH_{2n+1}$, which contains 1 to 6, 1 to 8, 1 to 10, or 1 to 20 carbon atoms and is derived from a saturated linear or branched hydrocarbon moiety. For example, "$C_{1-6}$ alkoxy" refers to an oxygen radical having a linear or branched hydrocarbon radical containing 1 to 6 carbon atoms, unless otherwise specified. Examples thereof include, but are not limited to, methoxy, ethoxy, propoxy, isopropoxy, n-butoxy, sec-butoxy, t-butoxy, pentoxy, hexoxy, and the like.

The term "cycloalkyl" as used herein, unless otherwise stated, refers to a monovalent group derived from a saturated monocyclic or partially unsaturated monocyclic carbocyclic ring compound. For example, the term "$C_{3-7}$ cycloalkyl" as used herein, unless otherwise stated, refers to a monocyclic saturated or partially unsaturated hydrocarbon functional group having 3 to 7 carbon atoms. Examples of saturated cycloalkyl include, but are not limited to, cyclopropyl, cyclobutyl, cyclopentyl, cyclohexyl, cycloheptyl, and the like.

The term "heterocyclyl" as used herein, unless otherwise stated, refers to a 3- to 7-membered monocyclic monovalent group containing 1 to 3 heteroatoms or functional groups selected from among N, O, S, SO and $SO_2$. Examples thereof include, but are not limited to, oxetan-3-yl, tetrahydrofuran-3-yl, tetrahydro-2H-pyran-4-yl, tetrahydro-2H-pyran-3-yl, oxepan-4-yl, oxepan-3-yl, piperidin-1-yl, piperidin-3-yl, piperidin-4-yl, piperazin-1-yl, morpholin-4-yl, thiomorpholin-4-yl, 1,1-dioxide thiomorpholin-4-yl, pyrrolidin-1-yl, pyrrolidin-3-yl, azetidin-1-yl, azetidin-3-yl, aziridin-1-yl, azepan-1-yl, azepan-3-yl, azepan-4-yl.

The term "aryl" as used herein, unless otherwise stated, refers to a mono- or poly-cyclic carbocyclic ring system containing 6 to 14 carbon atoms and having one or more fused or unfused aromatic rings. Examples of aryl include, but are not limited to, phenyl, naphthyl, tetrahydronaphthyl, indenyl, andracenyl, and the like.

The term "heteroaryl" as used herein, unless otherwise stated, refers to a 5- to 12-membered (preferably 5- to 7-membered) monocyclic or bicyclic or higher aromatic group containing at least one, for example, 1 to 4, preferably 1 to 3 heteroatoms, selected from among O, N and S. Examples of monocyclic heteroaryl include, but are not limited to, thiazolyl, oxazolyl, thiophenyl, furanyl, pyrrolyl, imidazolyl, isoxazolyl, pyrazolyl, triazolyl, thiadiazolyl, tetrazolyl, oxadiazolyl, pyridinyl, pyridazinyl, pyrimidinyl, pyrazinyl, and groups similar thereto. Examples of bicyclic heteroaryl include, but are not limited to, indolyl, benzothiophenyl, benzofuranyl, benzimidazolyl, benzoxazolyl, benzisoxazolyl, benzthiazolyl, benzthiadiazolyl, benztriazolyl, quinolinyl, isoquinolinyl, purinyl, furopyridinyl, and similar groups thereto.

As used herein, the term "enzymatic activity of EZH1 and/or EZH2" means an enzymatic activity of EZH1 and/or EZH2 that introduces a methyl group into lysine 27 of histone H3, and the term "increased expression of EZH1 and/or EZH2" means that the expression level of EZH1 protein and/or EZH2 protein is increased by enhancement of gene transcription activity, promotion of translation, inhibition of protein degradation, enhancement of protein stabilization, or the like.

As used herein, the expression "mutation exists in EZH1 and/or EZH2" means that a mutation exists in the nucleotide sequence and/or amino acid sequence of EZH1 and/or EZH2. For example, somatic mutations exist at tyrosine 641, alanine 677, alanine 687 of EZH2 (Y641F, Y641N, Y641S, Y641C, A677G, and A687V).

Hereinafter, the present disclosure will be described in more detail.

The present disclosure relates to novel heterotricyclic derivative compounds of the following Formula 1 and the use thereof, and more particularly, to novel heterotricyclic derivative compounds having inhibitory activity against EZH1 (enhancer of zeste homolog 1) and/or EZH2 (enhancer of zeste homolog 2) activity, pharmaceutically acceptable salts thereof, or pharmaceutical compositions containing these compounds.

Specifically, in accordance with an embodiment of the present disclosure, there is provided a compound selected from among a heterotricyclic derivative compound of the following Formula 1, a pharmaceutically acceptable salt thereof, an optical isomer thereof, a hydrate thereof, and a solvate thereof:

[Formula 1]

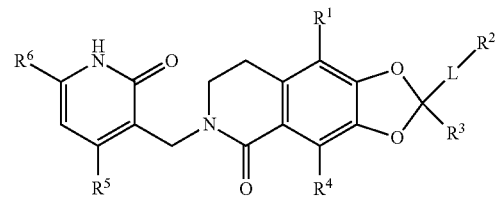

wherein:
$R^1$ is H, a halogen, cyano, a $C_{1-6}$ alkyl containing 0 to 3 halogen atoms, a $C_{1-6}$ alkoxy containing 0 to 3 halogen atoms, $C_{3-6}$ cycloalkyl, $C_{1-6}$ alkylcarbonyl, $C_{2-6}$ alkenyl, $C_{2-6}$ alkynyl, $C_{3-6}$ cycloalkenyl, aryl, a 5- to 6-membered aromatic heterocyclyl containing 1 to 3 heteroatoms independently selected from the group consisting of N, O and S in a ring thereof, or a 5- to 6-membered aliphatic heterocyclyl containing 1 or 2 heteroatoms independently selected from the group consisting of N, O and S in a ring thereof and containing or not containing an unsaturated bond in a part of the ring thereof;

the $C_{3-6}$ cycloalkyl, the aryl, the 5- to 6-membered aromatic heterocyclyl containing 1 to 3 heteroatoms independently selected from the group consisting of N, O and S in the ring thereof, or the 5- to 6-membered aliphatic heterocyclyl containing 1 or 2 heteroatoms independently selected from the group consisting of N, O and S in a ring thereof and containing or not containing an unsaturated bond in a part of the ring thereof is unsubstituted or substituted with one to three independently selected from Group A below;

L is a bond, $C_{1-6}$ alkylene, or oxy($C_{1-6}$)alkylene;

$R^2$ is H, $C_{1-6}$ alkyl, $C_{3-6}$ cycloalkyl, a 5- to 6-membered aliphatic heterocyclyl containing 1 or 2 heteroatoms independently selected from the group consisting of N, O and S in a ring thereof, aryl, a 5- to 6-membered aromatic heterocyclyl containing 1 to 3 heteroatoms independently selected from the group consisting of N, O and S in a ring thereof, or 5- to 12-membered bicyclic heteroaryl;

the $C_{1-6}$ alkyl, the $C_{3-6}$ cycloalkyl, the 5- to 6-membered aliphatic heterocyclyl, the aryl, the 5- to 6-membered aromatic heterocyclyl, or the 5- to 12-membered bicyclic heteroaryl is unsubstituted or substituted with one or three independently selected from Group C below;

$R^3$ is $C_{1-6}$ alkyl;

$R^4$ is H, a halogen, or a $C_{1-6}$ alkyl containing 0 to 3 halogen atoms;

$R^5$ is $C_{1-6}$ alkyl or $C_{1-6}$ alkoxy;

$R^6$ is $C_{1-6}$ alkyl;

Group A is a halogen, $C_{1-6}$ alkyl, $C_{1-6}$ alkoxy, or a 5 to 6-membered aliphatic heterocyclyl containing 1 or 2 heteroatoms independently selected from the group consisting of N, O and S in a ring thereof, wherein the $C_{1-6}$ alkyl, the $C_{1-6}$ alkoxy and the 5 to 6-membered aliphatic heterocyclyl are unsubstituted or substituted with one to three independently selected from Group B below;

Group B is a halogen, $C_{1-6}$ alkyl, or a 5 to 6-membered aliphatic heterocyclyl containing 1 or 2 heteroatoms independently selected from the group consisting of N, O and S in a ring thereof; and Group C is hydroxy, formyl, a $C_{1-6}$ alkyl containing 0 to 3 halogen atoms, substituted or unsubstituted $C_{1-6}$ alkylcarbonyl, $C_{1-6}$ alkoxy, $C_{1-6}$ alkylsulfonyl, —NR$^{20}$R$^{21}$, $(C_{1-6})$alkoxy$(C_{1-6})$alkyl, di$(C_{1-6})$alkylamino$(C_{1-6})$alkyl, or a 4- to 6-membered aliphatic heterocyclyl containing 1 to 2 heteroatoms independently selected from the group consisting of N, O and S in a ring thereof, wherein $R^{20}$ and $R^{21}$ are each independently H, formyl, $C_{1-6}$ alkyl, or substituted or unsubstituted $C_{1-6}$ alkylcarbonyl.

Preferably, the compound selected from among the heterotricyclic derivative compound of Formula 1 according to the present disclosure, a pharmaceutically acceptable salt thereof, an optical isomer thereof, a hydrate thereof, and a solvate thereof may be a compound wherein $R^1$ is H, a halogen, a $C_{1-6}$ alkyl containing 0 to 3 halogen atoms, $C_{1-6}$ alkoxy, $C_{3-6}$ cycloalkyl, $C_{2-6}$ alkenyl, $C_{2-6}$ alkynyl, $C_{3-6}$ cycloalkenyl, aryl, a 5- to 6-membered aromatic heterocyclyl containing 1 to 3 heteroatoms independently selected from the group consisting of N, O and S in a ring thereof, or a 5- to 6-membered aliphatic heterocyclyl containing 1 or 2 heteroatoms independently selected from the group consisting of N, O and S in a ring thereof and containing or not containing an unsaturated bond in a part of the ring thereof.

Preferably, the compound selected from among the heterotricyclic derivative compound of Formula 1 according to the present disclosure, a pharmaceutically acceptable salt thereof, an optical isomer thereof, a hydrate thereof, and a solvate thereof may be a compound wherein $R^1$ is H, halogen, methyl, ethyl, nitrile, methoxy, ethoxy, cyclopropyl, vinyl, acetylenyl, phenyl, isopropenyl, isopropyl, cyclopentenyl, cyclopentyl, cyclohexenyl, cyclohexyl, furanyl, pyridine, pyrazolyl, dihydropyranyl, or thiazolyl.

Preferably, the compound selected from among the heterotricyclic derivative compound of Formula 1 according to the present disclosure, a pharmaceutically acceptable salt thereof, an optical isomer thereof, a hydrate thereof, and a solvate thereof may be a compound wherein $R^2$ is $C_{1-6}$ alkyl, $C_{3-6}$ cycloalkyl, a 5- to 6-membered aliphatic heterocyclyl containing 1 or 2 heteroatoms independently selected from the group consisting of N, O and S in a ring thereof, aryl, a 5- to 6-membered aromatic heterocyclyl containing 1 to 3 heteroatoms independently selected from the group consisting of N, O and S in a ring thereof, or 5- to 12-membered bicyclic heteroaryl, wherein the $C_{1-6}$ alkyl, the $C_{3-6}$ cycloalkyl, the 5- to 6-membered aliphatic heterocyclyl, the aryl, the 5- to 6-membered aromatic heterocyclyl, or the 5- to 12-membered bicyclic heteroaryl is unsubstituted or substituted with one or three independently selected from the group consisting of $C_{1-6}$ alkyl, $C_{1-6}$ alkylsulfonyl, hydroxy, $C_{1-6}$ alkoxy, amino, $C_{1-6}$ alkylamino, di$(C_{1-6})$alkylamino, a 3- to 6-membered aliphatic heterocyclyl containing 1 or 2 heteroatoms in a ring thereof, and alkylamide.

Preferably, the compound selected from among the heterotricyclic derivative compound of Formula 1 according to the present disclosure, a pharmaceutically acceptable salt thereof, an optical isomer thereof, a hydrate thereof, and a solvate thereof may be a compound wherein L is a bond or methylene;

$R^2$ is butyl, cyclobutyl, cyclopentyl, cyclohexyl, tetrahydropyranyl, piperidyl, phenyl, pyridine, indole, or isoxazole; and $R^3$ is methyl, wherein the butyl, cyclobutyl, cyclopentyl, cyclohexyl, tetrahydropyranyl, piperidyl, phenyl, pyridine, indole, or isoxazole is unsubstituted or substituted with one independently selected from the group consisting of methyl, ethyl, ethylsulfonyl, hydroxy, methoxy, amino, methylamino, ethylamino, dimethylamino, diethylamino, ethylmethylamino, piperidyl, pyrrolidyl, trifluoroethyl, and (R)-2-hydroxybutanamide.

Preferably, the compound selected from among the heterotricyclic derivative compound of Formula 1 according to the present disclosure, a pharmaceutically acceptable salt thereof, an optical isomer thereof, a hydrate thereof, and a solvate thereof may be a compound wherein L is a bond;

$R^1$ and $R^4$ are each independently H, a halogen, or methyl;

$R^2$ is $C_{3-6}$ cycloalkyl or a $C_{3-6}$ cycloalkyl substituted with NR$^{20}$R$^{21}$; and $R^3$, $R^5$ and $R^6$ are methyl;

wherein NR$^{20}$R$^{21}$ is one selected from the group consisting of amino, $C_{1-6}$ alkylamino, and di$(C_{1-6})$alkylamino.

In addition, preferred examples of the compound of Formula 1 according to the present disclosure include, but are not limited to:

6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one;

4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one;

4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one isomer A;

4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one isomer B;

4,9-dichloro-6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one;

2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer A;

9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer B;

9-chloro-6-((4,6-dimethyl-2-oxo-1,2-dihydropyridin-3-yl)methyl)-2-(cis-4-(dimethylamino)cyclohexyl)-2,4-dimethyl-7,8-dihydro-[1,3]dioxolo[4,5-g]isoquinolin-5(6H)-one;

9-chloro-2-(trans-4-(dimethylamino)cyclohexyl)-6-((4-methoxy-6-methyl-2-oxo-1,2-dihydropyridin-3-yl)methyl)-2,4-dimethyl-7,8-dihydro-[1,3]dioxolo[4,5-g]isoquinolin-5(6H)-one;

9-chloro-2-(trans-4-(dimethylamino)cyclohexyl)-2,4-dimethyl-6-((6-methyl-2-oxo-4-propyl-1,2-dihydropyridin-3-yl)methyl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(trans-4-(ethylamino)cyclohexyl)-2,4-dimethyl-7,8-dihydro-[1,3]dioxolo[4,5-g]isoquinolin-5(6H)-one;

9-chloro-2-(trans-4-(diethylamino)cyclohexyl)-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(trans-4-(piperidin-1-yl)cyclohexyl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(trans-4-(pyrrolidin-1-yl)cyclohexyl)-7,8-dihydro-[1,3]dioxolo[4,5-g]isoquinolin-5(6H)-one;

(2S)—N-(trans-4-(9-chloro-6-((4,6-dimethyl-2-oxo-1,2-dihydropyridin-3-yl)methyl)-2,4-dimethyl-5-oxo-5,6,7,8-tetrahydro-[1,3]dioxolo[4,5-g]isoquinolin-2-yl)cyclohexyl)-2-hydroxybutanamide;

2-((trans-4-aminocyclohexyl)methyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(((trans-4-(dimethylamino)cyclohexyl))methyl)-2,4-dimethyl-7,8-dihydro-[1,3]dioxolo[4,5-g]isoquinolin-5(6H)-one;

9-chloro-2-cyclohexyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one;

9-chloro-2-cyclopentyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(tetrahydro-2H-pyran-4-yl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(4-(dimethylamino)phenyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(4-(dimethylamino)butyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(3,5-(dimethylisoxazol-4)-yl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(piperidin-4-yl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(1-methylpiperidin-4-yl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(1-((R)-2-hydroxybutanoyl)piperidin-4-yl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(1-(2,2,2-trifluoroethyl)piperidin-4-yl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(1-methyl-1H-indol-5-yl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(trans-4-methoxycyclohexyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(trans-3-(dimethylamino)cyclobutyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(cis-3-(dimethylamino)cyclohexyl)-2,4-dimethyl-7,8-dihydro-[1,3]dioxolo[4,5-g]isoquinolin-5(6H)-one;

9-chloro-6-((4,6-dimethyl-2-oxo-1,2-dihydropyridin-3-yl)methyl)-2-(cis-3-(dimethylamino)cyclopentyl)-2,4-dimethyl-7,8-dihydro-[1,3]dioxolo[4,5-g]isoquinolin-5(6H)-one;

2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one isomer A;

6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one isomer B;

2-(trans-4-(dimethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one;

2-(trans-4-(dimethylamino)cyclohexyl)-2,4,9-trimethyl-6-((6-methyl-2-oxo-4-propyl-1,2-dihydropyridin-3-yl)methyl)-7,8-dihydro-[1,3]dioxolo[4,5-g]isoquinolin-5(6H)-one;

2-cyclohexyl-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one;

2-(trans-4-(ethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one;

2-(trans-4-(diethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one;

2-(trans-4-(ethyl(methyl)amino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one;

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer A;

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer B;

9-bromo-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-vinyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-ethynyl-2,4-dimethyl-7,8-dihydro-[1,3]dioxolo[4,5-g]isoquinolin-5(6H)-one;

9-cyclopropyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(4-(morpholinomethyl)phenyl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-phenyl-7,8-dihydro-[1,3]dioxolo[4,5-g]isoquinolin-5(6H)-one;

9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

9-cyclopentyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

9-(cyclohex-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

9-cyclohexyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(prop-1-en-2-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-isopropyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-ethyl-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one;

9-(3,6-dihydro-2H-pyran-4-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one;

6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one; and 6-((4,6-dimethyl-2-oxo-1,2-dihydropyridin-3-yl)methyl)-2-(trans-4-(dimethylamino)cyclohexyl)-2,4-dimethyl-5-oxo-5,6,7,8-tetrahydro-[1,3]dioxolo[4,5-g]isoquinoline-9-carbonitrile.

In the present disclosure, a method for producing the compound represented by Formula 1 is not particularly limited, but the compound represented by Formula 1 may be synthesized, for example, by a production method shown in the following Reaction Scheme 1:

[Reaction Scheme 1]

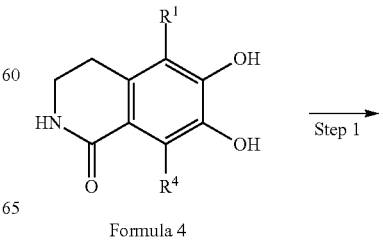

Formula 4

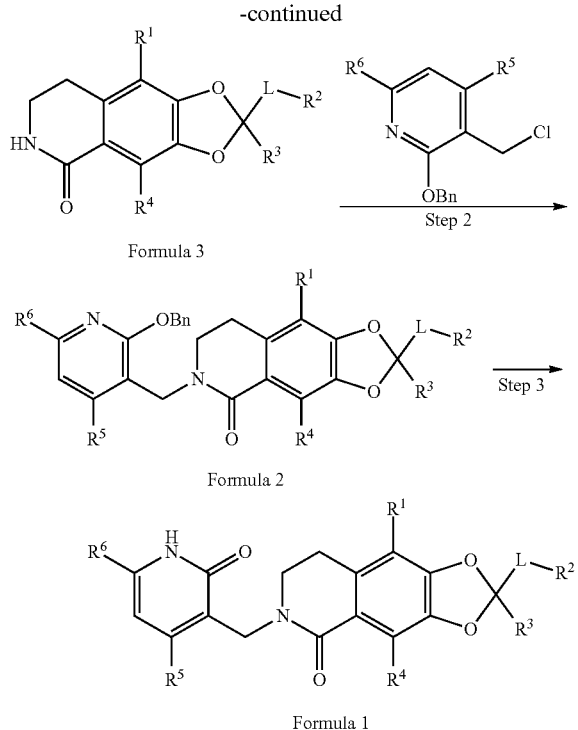

wherein R¹, R², R³, R⁴, R⁵ and R⁶ are each as defined above with respect to Formula 1.

The ketalization reaction of Step 1 in Reaction Scheme 1 may be carried out under the conditions shown in Ming Li et. al., *J. Org. Chem.* 2008, 73, 8658-8660. Step 1 is a step of obtaining the compound of Formula 3 by stirring the compound of Formula 4 together with an equal or excess amount of an acetylene derivative in a solvent inert to the reaction in the presence of 0.01 to 0.3 equivalents of a Ru catalyst under heating conditions for 1 to 24 hours. The condensation reaction of Step 2 is a process of obtaining the compound of Formula 2 by stirring the compound of Formula 3 together with an equal or excess amount of a corresponding alkyl halide in a solvent inert to the reaction in the presence of a base such as potassium t-butoxide under low-temperature conditions for 1 to 24 hours. The deprotection reaction of Step 3 is a process of obtaining the compound of Formula 1 by stirring the compound of Formula 2 containing a benzyl group in a solvent inert to the reaction in the presence of an acid under cooling or heating conditions for 0.5 to 24 hours.

The compounds according to the present disclosure may also form pharmaceutically acceptable salts. These pharmaceutically acceptable salts are not particularly limited as long as they are salts formed with an acid that forms a non-toxic acid addition salt containing a pharmaceutically acceptable anion. Examples of the salts include acid addition salts formed with inorganic acids such as hydrochloric acid, sulfuric acid, nitric acid, phosphoric acid, hydrobromic acid, hydroiodic acid and the like; organic carboxylic acids such as tartaric acid, formic acid, citric acid, acetic acid, trichloroacetic acid, trifluoroacetic acid, gluconic acid, benzoic acid, lactic acid, fumaric acid, maleic acid and the like; or sulfonic acids such as methanesulfonic acid, benzenesulfonic acid, p-toluenesulfonic acid, naphthalenesulfonic acid, and the like.

Meanwhile, the compounds according to the present disclosure may have an asymmetric carbon center, and thus may exist as R or S isomers, racemic compounds, diastereomeric mixtures, or individual diastereomers, and these isomers and mixtures are all included within the scope of the present disclosure.

In addition, solvate and hydrate forms of Formula 1 are also included within the scope of the present disclosure.

In accordance with another embodiment of the present disclosure, there is provided a pharmaceutical composition containing a therapeutically effective amount of a compound selected from the compound of Formula 1 and a pharmaceutically acceptable salt thereof.

The pharmaceutical composition of the present disclosure is useful for preventing or treating various diseases associated with EZH1 and/or EZH2, because the compound of Formula 1 contained therein inhibits the activity of EZH1 and/or EZH2.

According to another embodiment of the present disclosure, the pharmaceutical composition is a pharmaceutical composition for preventing or treating cancer or tumors that may be treated by inhibiting the enzymatic activity of EZH1 and/or EZH2.

According to still another embodiment of the present disclosure, there is provided a pharmaceutical preparation comprising the pharmaceutical composition.

The pharmaceutical formation of the present disclosure may be in various oral dosage forms such as tablets, pills, powders, capsules, syrups or emulsions, or parenteral dosage forms for intramuscular, intravenous or subcutaneous administration, such as injections, and may preferably be in an oral dosage form.

In addition, the pharmaceutical preparation may be formulated according to a conventional method by adding a conventional non-toxic pharmaceutically acceptable additive, for example, at least one selected from the group consisting of carriers, adjuvants and excipients, in addition to the active ingredient.

Excipients that may be used in the pharmaceutical preparation of the present disclosure include, but are not limited to, sweeteners, binders, solubilizers, dissolution aids, wetting agents, emulsifiers, isotonic agents, adsorbents, disintegrants, antioxidants, preservatives, lubricants, fillers, fragrances, etc. For example, as excipients, there may be used lactose, dextrose, sucrose, mannitol, sorbitol, cellulose, glycine, silica, magnesium aluminum silicate, starch, gelatin, gum tragacanth, arginic acid, sodium alginate, methylcellulose, sodium carboxymethyl cellulose, water, ethanol, polyethylene glycol, polyvinylpyrrolidone, sodium chloride, calcium chloride, orange essence, strawberry essence, vanilla flavor, etc.

When the pharmaceutical preparation of the present disclosure is in an oral dosage form, examples of a carrier that is used in this case include, but are not limited to, cellulose, calcium silicate, corn starch, lactose, sucrose, dextrose, calcium phosphate, stearic acid, magnesium stearate, calcium stearate, gelatin, talc, and the like.

When the pharmaceutical preparation of the present disclosure is in the form of an injection, examples of the carrier include, but are not limited to, water, saline, aqueous glucose solution, aqueous pseudo-sugar solution, alcohol, glycol, ether, oil, fatty acid, fatty acid ester, glyceride, etc.

To use the compound according to the present disclosure as a pharmaceutical agent, the latter are brought into the form of a pharmaceutical preparation, which in addition to the active ingredient for oral or parenteral administration, contains suitable pharmaceutical, organic or inorganic inert support media, for example, water, gelatin, gum arabic, lactose, starch, vegetable oil, polyalkylene glycol, etc. The pharmaceutical preparation may be present in solid form, for example, as tablets, coated tablets, suppositories, or capsules, or in liquid form, for example, as solutions, suspensions, or emulsions. Moreover, the pharmaceutical preparation optionally contains adjuvants, such as preservatives, stabilizers, wetting agents or emulsifiers; salts for changing the osmotic pressure or buffers.

For parenteral administration, especially injection solutions or suspensions are suitable.

As carrier systems, surface-active adjuvants, such as salts of bile acids or animal or plant phospholipids, but also mixtures thereof, as well as liposomes or their components may also be used.

For oral administration, especially tablets, coated tablets or capsules containing talc and/or hydrocarbon vehicles or binders, for example, lactose, corn or potato starch, are suitable. The administration may also be carried out in liquid form, for example, as a juice, to which a sweetener is added.

In addition, the dosage of the compound of Formula 1 according to the present disclosure for the human body is preferably in the range of 0.1 mg/day to 2,000 mg/day for an adult patient weighing 70 kg in general. The compound according to the present disclosure may be administered once or several times a day. However, the above dosage may vary depending on the patient's health status, age, weight and sex, dosage form and the severity of the disease, and accordingly, the scope of the present disclosure is not limited to the above-described dosage.

Hereinafter, the present disclosure will be described in more detail with reference to the following production examples and examples, but these examples are merely illustrative of the present disclosure, and the scope of the present disclosure is not limited thereto.

EXAMPLES

Intermediate Synthesis Examples

[Intermediate 1] 6,7-dihydroxy-8-methyl-3,4-dihydroisoquinolin-1(2H)-one

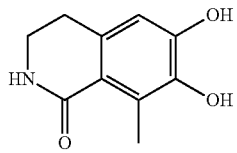

Step 1. Production of methyl 3,4-dimethoxy-2-methylbenzoate

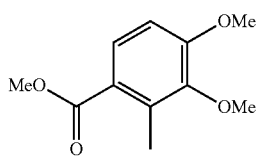

Methyl 3,4-dihydroxy-2-methylbenzoate (5.0 g, 27.4 mmol) was dissolved in acetone (50 ml), and then potassium carbonate (18.9 g, 137.0 mmol) and iodomethane (5.1) ml, 82.3 mmol) were sequentially added thereto. After completion of the addition, the mixture was stirred at room temperature for 24 hours. The reaction product was diluted with dichloromethane and water, and the organic layer was extracted. The extracted organic layer was dried over anhydrous sodium sulfate and distilled under reduced pressure to obtain the title compound (5.4 g), which was used without further purification.

Step 2. Production of 3,4-dimethoxy-2-methylbenzoic acid

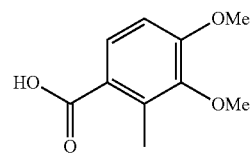

Methyl 3,4-dimethoxy-2-methylbenzoate (5.4 g, 27.4 mmol) synthesized in Step 1 above was added to a mixture of methanol/water (1/1, 54 ml), and then sodium hydroxide (3.3 g, 82.2 mmol) was added thereto. After completion of the addition, the mixture was warmed and refluxed for 4 hours. After completion of the reaction, the reaction solution was cooled to low temperature and then acidified to a pH of about 1 using 6.0N aqueous hydrochloric acid. The resulting solid was stirred at low temperature for 1 hour, collected by filtration, washed with water, and dried to obtain the title compound (5.4 g), which was used without further purification.

Step 3. Production of N-(2,2-dimethoxyethyl)-3,4-dimethoxy-2-methylbenzamide

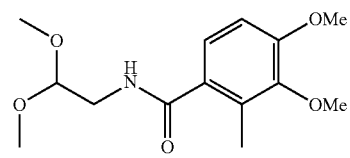 [SMILES: COc1ccc(C(=O)NCC(OC)OC)c(C)c1OC]

3,4-dimethoxy-2-methylbenzoic acid (5.4 g, 27.4 mmol) synthesized in Step 2 above was dissolved in N,N-dimethylformamide (54 ml), and then 1-hydroxybenzotriazole (4.8 g, 35.6 mmol), 1-ethyl-3-(3-dimethylaminopropyl)carbodiimide hydrochloride (6.8 g, 35.6 mmol) and triethylamine (5 ml, 35.6 mmol) were sequentially added thereto, followed by stirring at room temperature for 1 hour. A mixture of aminoacetaldehyde dimethyl acetal (3.9 ml, 35.6 mmol) and triethylamine (5 ml, 35.6 mmol) was added dropwise thereto over about 5 minutes, and then the resulting mixture was stirred at room temperature overnight. The reaction product was diluted with dichloromethane and water, and the organic layer was extracted. The extracted organic layer was washed with water and brine, dried over anhydrous sodium sulfate, and distilled under reduced pressure to obtain the title compound (7.8 g), which was used without further purification.

Step 4. Production of 7-hydroxy-6-methoxy-8-methylisoquinolin-1(2H)-one

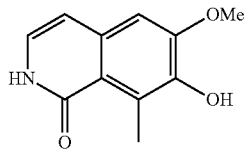

N-(2,2-dimethoxyethyl)-3,4-dimethoxy-2-methylbenzamide (7.8 g, 27.4 mmol) synthesized in Step 3 above was added to concentrated sulfuric acid (35 ml) and then heated to 60° C., followed by stirring for 4 hours. The reaction solution was cooled to room temperature, poured into ice water, and then stirred for 30 minutes. The resulting solid was collected by filtration, washed with excess water and dried to obtain the title compound (5.7 g), which was used without further purification.

Step 5. Production of 7-hydroxy-6-methoxy-8-methyl-3,4-dihydroisoquinolin-1(2H)-one

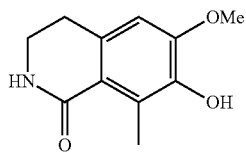

7-hydroxy-6-methoxy-8-methylisoquinolin-1(2H)-one (5.7 g, 27.4 mmol) synthesized in Step 4 above and 10% palladium/carbon (2.7 g) were added to a mixture of methanol/ethanol (1/1, 57 ml), and then a hydrogen balloon was attached. The reaction solution was heated to 60° C., stirred overnight, cooled to room temperature, filtered through celite, and then distilled under reduced pressure. The resulting product was stirred in dichloromethane, collected by filtration, washed with dichloromethane and dried to obtain the title compound (3.39 g).

Step 6. Production of 6,7-dihydroxy-8-methyl-3,4-dihydroisoquinolin-1(2H)-one

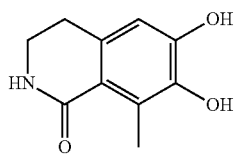

7-hydroxy-6-methoxy-8-methyl-3,4-dihydroisoquinolin-1(2H)-one (100 mg, 0.482 mmol) synthesized in Step 5 above was added to dichloromethane (2 ml) under nitrogen, and then the reaction solution was cooled to 0° C. Tribromoboron (1 ml, 0.96 mmol, 1M solution in dichloromethane) was added thereto, and then the mixture was warmed slowly to room temperature and stirred overnight. Ice water was added to the reaction solution, and the resulting solid was stirred for 1 hour, collected by filtration, washed with excess water and dichloromethane, and dried to obtain the title compound (53 mg).

[Intermediate 2] 6,7-dihydroxy-3,4-dihydroisoquinolin-1(2H)-one

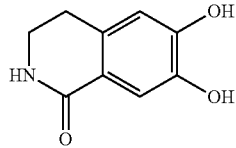 [SMILES: O=C1NCCc2cc(O)c(O)cc21]

The same reaction as in Step 6 of Intermediate 1 was performed using 6,7-dimethoxy-3,4-dihydroisoquinolin-1(2H)-one (500 mg, 15.6 mmol) synthesized according to the method described in Asian Journal of Organic Chemistry, 5(2), 287-292; 2016, and the resulting residue was purified by silica gel column chromatography to obtain the title compound (190 mg).

[Intermediate 3] 6,7-dihydroxy-5,8-dimethyl-3,4-dihydroisoquinolin-1(2H)-one

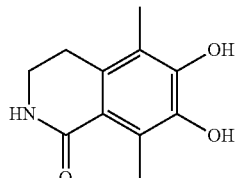

Step 1. Production of methyl 3,4-dimethoxy-2,5-dimethylbenzoate

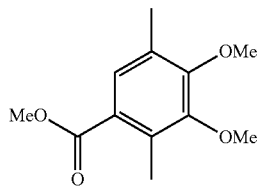 [SMILES: COC(=O)c1cc(C)c(OC)c(OC)c1C]

The title compound (2.3 g) was obtained by performing the same reaction as in Step 1 of Intermediate 1, except that methyl 3,4-dihydroxy-2,5-dimethylbenzoate (2.0 g, 10.1 mmol) was used instead of methyl 3,4-dihydroxy-2-methylbenzoate.

Step 2. Production of 3,4-dimethoxy-2,5-dimethylbenzoic acid

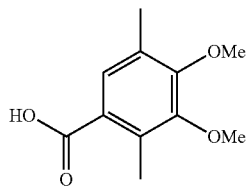

The title compound (2.1 g) was obtained by performing the same reaction as in Step 2 of Intermediate 1 using methyl 3,4-dimethoxy-2,5-dimethylbenzoate (2.3 g, 10.1 mmol) synthesized in Step 1 above.

Step 3. Production of N-(2,2-dimethoxyethyl)-3,4-dimethoxy-2,5-dimethylbenzamide

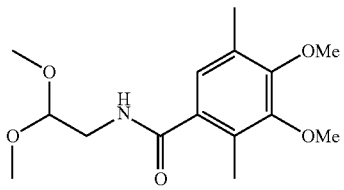 [SMILES: COc1c(C)cc(C(=O)NCC(OC)OC)c(C)c1OC]

The title compound (3.0 g) was obtained by performing the same reaction as in Step 3 of Intermediate 1 using 3,4-dimethoxy-2,5-dimethylbenzoic acid (2.1 g, 10.1 mmol) synthesized in Step 2 above.

Step 4. Production of 6,7-dihydroxy-5,8-dimethylisoquinolin-1(2H)-one

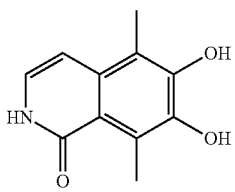

The title compound (1.8 g) was obtained by performing the same reaction as in Step 4 of Intermediate 1 for 24 hours using N-(2,2-dimethoxyethyl)-3,4-dimethoxy-2,5-dimethylbenzamide (3.0 g, 10.1 mmol) synthesized in Step 3 above.

Step 5. Production of 6,7-dihydroxy-5,8-dimethyl-3,4-dihydroisoquinolin-1(2H)-one

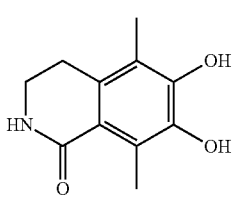

The title compound (780 mg) was obtained by performing the same reaction as in Step 5 of Intermediate 1 for 48 hours using 6,7-dihydroxy-5,8-dimethylisoquinolin-1(2H)-one (1.8 g, 8.8 mmol) synthesized in Step 4 above.

[Intermediate 4] 5-chloro-6,7-dihydroxy-8-methyl-3,4-dihydroisoquinolin-1(2H)-one

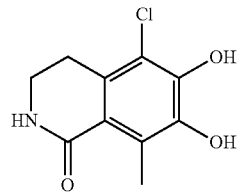

Step 1. Production of 5-chloro-7-hydroxy-6-methoxy-8-methyl-3,4-dihydroisoquinolin-1(2H)-one

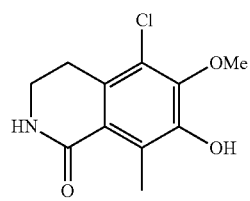

7-hydroxy-6-methoxy-8-methyl-3,4-dihydroisoquinolin-1(2H)-one (938 mg, 4.53 mmol) synthesized in Step 5 of Intermediate 1 was dissolved in acetic acid (20 ml), and N-chlorosuccinimide (1.2 g, 9.05 mmol) was added thereto. The reaction solution was heated to 70° C. and stirred for 1 hour. The reaction solution was cooled to room temperature, neutralized by adding saturated aqueous sodium bicarbonate solution, and extracted using 20% methanol-chloroform. The extracted organic layer was washed with brine, dried using anhydrous sodium sulfate, and distilled under reduced pressure. The resulting residue was purified by silica gel column chromatography, and the resulting residue was stirred in diethyl ether for 1 hour. The resulting solid was filtered and washed to obtain the title compound (380 mg).

Step 2. Production of 5-chloro-6,7-dihydroxy-8-methyl-3,4-dihydroisoquinolin-1(2H)-one

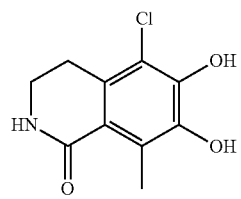

The title compound (293 mg) was obtained by performing the same reaction as in Step 6 of Intermediate 1 using 5-chloro-7-hydroxy-6-methoxy-8-methyl-3,4-dihydroisoquinolin-1(2H)-one (377 mg, 1.56 mmol) synthesized in Step 1 above.

[Intermediate 5] 8-chloro-6,7-dihydroxy-5-methyl-3,4-dihydroisoquinolin-1(2H)-one

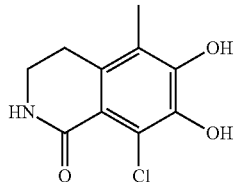

Step 1. Production of methyl 5-chloro-3,4-dihydroxy-2-methylbenzoate

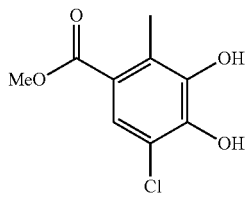

Methyl 3,4-dihydroxy-2-methylbenzoate (2.0 g, 10.98 mmol) was dissolved in ethyl acetate (44 mL), and N-chlorosuccinimide (2.2 g, 16.47 mmol) was added thereto. The reaction solution was stirred at room temperature for 1 hour, and p-anisole (1.2 mL, 10.98 mmol) was added thereto. After stirring for an additional 15 minutes, the reaction solution was extracted using ethyl acetate. The organic layer was dried using anhydrous sodium sulfate and then distilled under reduced pressure. Dichloromethane (5 mL) was added to the resulting residue, followed by stirring for 30 minutes. Then, the solution was filtered to obtain the title compound (1.1 g), which was used without further purification.

Step 2. Production of methyl 5-chloro-3,4-dimethoxy-2-methylbenzoate

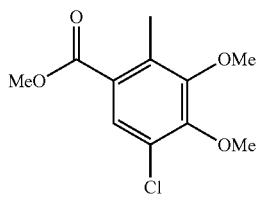 [SMILES: COC(=O)c1cc(Cl)c(OC)c(OC)c1C]

The title compound (2.6 g) was obtained by performing the same reaction as in Step 1 of Intermediate 1, except that methyl 5-chloro-3,4-dihydroxy-2-methylbenzoate (2.3 g, 10.59 mmol) synthesized in Step 1 above was used instead of methyl 3,4-dihydroxy-2-methylbenzoate.

Step 3. Production of (5-chloro-3,4-dimethoxy-2-methylphenyl)methanol

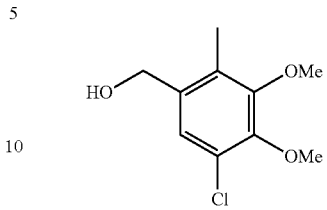

Methyl 5-chloro-3,4-dimethoxy-2-methylbenzoate (2.6 g, 10.63 mmol) synthesized in Step 2 above was dissolved in tetrahydrofuran (26 mL), argon gas replacement was performed, followed by cooling to 0° C. LiAlH$_4$ (403 mg, 10.63 mmol) was added to the reaction solution, followed by stirring at room temperature for 1 hour. The reaction product was cooled to 0° C., and excess water and 15% aqueous sodium hydroxide solution (2.5 mL) were added dropwise thereto. After stirring at room temperature for additional 2 hours, the reaction solution was filtered through celite. The resulting residue was extracted with ethyl acetate, dried using anhydrous sodium sulfate, and then distilled under reduced pressure to obtain the title compound (2.3 g).

Step 4. Production of 1-chloro-5-(chloromethyl)-2,3-dimethoxy-4-methylbenzene

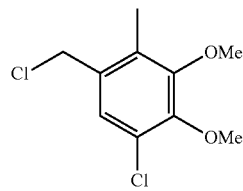

(5-chloro-3,4-dimethoxy-2-methylphenyl)methanol (2.1 g, 9.69 mmol) synthesized in Step 3 above was dissolved in ethyl acetate (50 mL) and cooled to 0° C. Thionyl chloride (1.1 mL, 14.53 mmol) was added dropwise to the reaction solution, followed by stirring at 0° C. for 1 hour. Excess water was added dropwise to the reaction product, followed by extraction with ethyl acetate. The obtained organic layer was dried using anhydrous sodium sulfate and distilled under reduced pressure to obtain the title compound (2.3 g), which was used without further purification.

Step 5. Production of 2-(5-chloro-3,4-dimethoxy-2-methylphenyl)acetonitrile

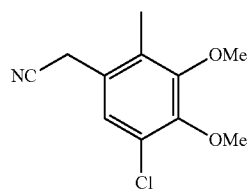

1-chloro-5-(chloromethyl)-2,3-dimethoxy-4-methylbenzene (2.3 g, 9.78 mmol) synthesized in Step 4 above was dissolved in dimethyl sulfoxide (23 mL), and then sodium cyanide (576 mg, 11.74 mmol) was added thereto at room temperature. The reaction solution was stirred at room temperature for 2 hours, and then excess water was added dropwise to the reaction product, followed by extraction with ethyl acetate. The obtained organic layer was dried using anhydrous sodium sulfate and distilled under reduced pressure to obtain the title compound (2.2 g), which was used without further purification.

Step 6. Production of 2-(5-chloro-3,4-dimethoxy-2-methylphenyl)ethan-1-amine

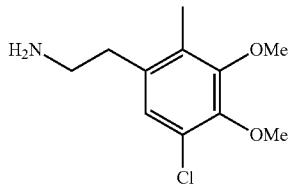

2-(5-chloro-3,4-dimethoxy-2-methylphenyl)acetonitrile (2.2 g, 9.75 mmol) synthesized in Step 5 above and an excess amount of Raney-nickel were dissolved in ethyl acetate (45 mL)), and then a hydrogen balloon was attached. The reaction solution was stirred at room temperature for 18 hours, filtered through celite, and distilled under reduced pressure to obtain the title compound (2.0 g), which was used without further purification.

Step 7. Production of 4-nitrophenyl(5-chloro-3,4-dimethoxy-2-methylphenethyl)carbamate

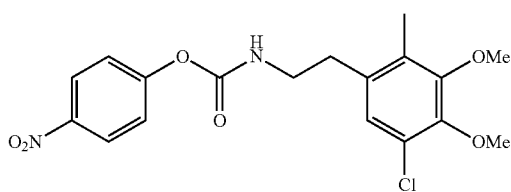 [SMILES: COc1c(Cl)cc(CCNC(=O)Oc2ccc([N+](=O)[O-])cc2)c(C)c1OC]

2-(5-chloro-3,4-dimethoxy-2-methylphenyl)ethan-1-amine (2.0 g, 8.71 mmol) synthesized in Step 6 above and sodium carbonate (2.77 g, 26.12 mmol)) were dissolved in 1,2-dichloroethane (40 mL), and 4-nitrophenylchloroformate (2.63 g, 13.06 mmol) was added thereto. After the reaction solution was stirred at room temperature for 18 hours, excess water was added dropwise to the reaction product, followed by extraction with dichloromethane. The obtained organic layer was dried using anhydrous sodium sulfate and distilled under reduced pressure. The resulting residue was purified by silica gel column chromatography to obtain the title compound (3.0 g).

Step 8. Production of 8-chloro-6,7-dimethoxy-5-methyl-3,4-dihydroisoquinolin-1(2H)-one

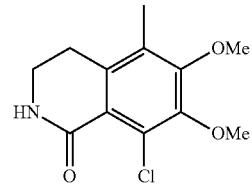 [SMILES: COc1c(C)c2c(c(Cl)c1OC)C(=O)NCC2]

4-nitrophenyl(5-chloro-3,4-dimethoxy-2-methylphenethyl)carbamate (3.0 g, 7.60 mmol) synthesized in [Step 7] above was dissolved in 1,2-dichloroethane (50 mL) and then cooled to 0° C. Triflic acid (7.3 mL, 81.1 mmol) was slowly added dropwise to the reaction solution, followed by stirring at 70° C. for 2 hours. The reaction product was cooled to room temperature, and then slowly added dropwise to excess ice water and stirred for 1 hour until the ice completely melted. The organic layer obtained by extraction with dichloromethane was neutralized with 2N aqueous sodium hydroxide solution. The organic layer was dried using anhydrous sodium sulfate and distilled under reduced pressure. The resulting residue was purified by silica gel column chromatography to obtain the title compound (1.6 g).

Step 9. Production of 8-chloro-6,7-dihydroxy-5-methyl-3,4-dihydroisoquinolin-1(2H)-one

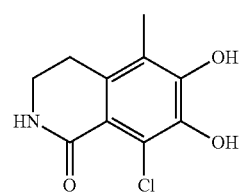

The title compound (1.2 g) was obtained by performing the same reaction as in Step 6 of Intermediate 1, except that 8-chloro-6,7-dimethoxy-5-methyl-3,4-dihydroisoquinolin-1(2H)-one (1.6 g, 6.14 mmol) synthesized in Step 8 above was used instead of 7-hydroxy-6-methoxy-8-methyl-3,4-dihydroisoquinolin-1(2H)-one.

[Intermediate 6] 6,7-dihydroxy-5-methyl-3,4-dihydroisoquinolin-1(2H)-one

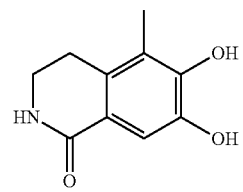

The title compound (220 mg) was obtained by performing the same reactions as in Step 1 to Step 9 of Intermediate 5, except that 3,4-dimethoxy-2-methylbenzoic acid (5.3 g, 27.01 mmol) was used instead of methyl 5-chloro-3,4-dimethoxy-2-methylbenzoate in Step 3 of Intermediate 5.

[Intermediate 7] 5,8-dichloro-6,7-dihydroxy-3,4-dihydroisoquinolin-1(2H)-one

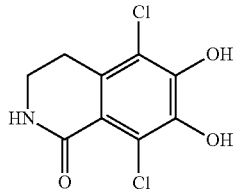 [SMILES: O=C1NCCc2c(Cl)c(O)c(O)c(Cl)c21]

3,4-dihydrobenzoic acid (10.0 g, 64.88 mmol) was added to acetic acid (44 mL), and sulfuryl chloride (12.6 ml, 155.72 mmol) was added thereto. The reaction solution was warmed to 50° C. and then stirred overnight. After the reaction solution was cooled to 0° C., the resulting solid was filtered and recrystallized from an ethyl acetate/hexane solvent to obtain 2,5-dichloro-3,4-dihydrobenzoic acid (4.2 g).

The title compound (55 mg) was obtained by performing the same reactions as in Step 1 to Step 9 of Intermediate 5, except that the above-synthesized 2,5-dichloro-3,4-dihydrobenzoic acid (4.2 g, using 18.92 mmol) was used instead of methyl 3,4-dihydroxy-2-methylbenzoate in Step 2 of Intermediate 5.

[Intermediate 8]
trans-4-ethynyl-N,N-dimethylcyclohexan-1-amine

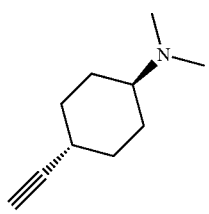

Step 1. Production of
trans-4-ethynylcyclohexan-1-amine

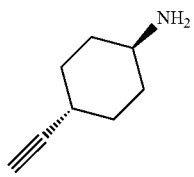

t-butyl-(trans-4-ethynylcyclohexyl)carbamate (2.5 g, 11.2 mmol) was added to methanol (25 ml), and then 4M hydrochloric acid-1,4-dioxane solution (24 ml, 95.2 mmol) was added thereto, followed by stirring at room temperature for 2 hours. After completion of the reaction, the reaction solution was neutralized by adding saturated aqueous sodium bicarbonate solution and extracted with using 20% methanol-chloroform. The extracted organic layer was washed with brine, dried using anhydrous sodium sulfate, and distilled under reduced pressure to obtain the title compound (1.3 g).

Step 2. Production of
trans-4-ethynyl-N,N-dimethylcyclohexan-1-amine

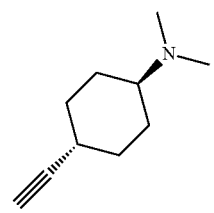

Trans-4-ethynylcyclohexan-1-amine (1.3 g, 10.6 mmol) synthesized in Step 1 above was added to methanol (110 ml), and 37% aqueous formaldehyde solution (1.8 ml, 23.5 mmol) was added thereto. The mixture was stirred at room temperature for 10 minutes, and then sodium triacetoxyborohydride (11.9 g, 56.0 mmol) was added thereto, followed by stirring at room temperature for 18 hours. After completion of the reaction, the reaction solution was neutralized with 1M aqueous sodium hydroxide solution and extracted using 20% methanol-chloroform. The extracted organic layer was washed with brine, dried using anhydrous sodium sulfate, and distilled under reduced pressure. The resulting residue was purified by basic silica gel column chromatography to obtain the title compound (1.4 g).

[Intermediate 9]
t-Butyl-(cis-4-ethynylcyclohexyl)carbamate

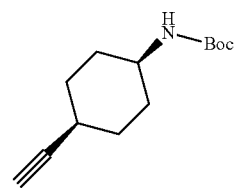 [SMILES: C#C[C@H]1CC[C@@H](NC(=O)OC(C)(C)C)CC1]

t-butyl-(cis-4-formylcyclohexyl)carbamate (800 mg, 3.52 mmol) was added to methanol (14 ml), and potassium carbonate (967 mg, 7.04 mmol) and dimethyl(1-diazo-2-oxopropyl)phosphonate (0.94 ml, 3.52 mmol) were added thereto. The mixture was stirred at room temperature for 1 hour and concentrated under reduced pressure. Ethyl acetate was added to the resulting residue, followed by washing with saturated brine. The obtained organic layer was dried using anhydrous sodium sulfate and distilled under reduced pressure. The resulting residue was purified by basic silica gel column chromatography to obtain the title compound (735 mg).

[Intermediate 10] t-butyl-(cis-4-ethynylcyclohexyl)carbamate

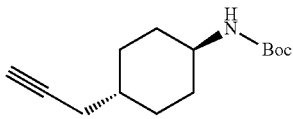 [SMILES: C#CC[C@H]1CC[C@H](NC(=O)OC(C)(C)C)CC1]

The title compound (720 mg) was obtained by performing the same reactions as in Intermediate 9, except that t-butyl-(trans-4-(2-oxoethyl)cyclohexyl)carbamate (1 g, 4.1 mmol) was used instead of t-butyl-(cis-4-formylcyclohexyl)carbamate.

[Intermediate 11] t-butyl-(trans-4-ethynylcyclohexyl)(methyl)carbamate

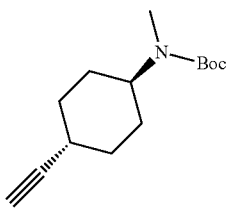 [SMILES: C#C[C@H]1CC[C@H](N(C)C(=O)OC(C)(C)C)CC1]

t-butyl-(trans-4-ethynylcyclohexyl)carbamate (1.0 g, 4.48 mmol) was added to N,N-dimethylformamide (4 ml). After argon gas replacement, sodium hydride (60%) (0.54 g, 13.44 mmol) was added to the reaction solution at 0° C., followed by stirring at room temperature for 30 minutes, and then methyl iodide (2.8 mL, 44.8 mmol) was slowly added to the reaction solution at 0° C. The reaction solution was stirred at room temperature for 16 hours, and dichloromethane was added to the resulting residue to separate the organic layer. The obtained organic layer was dried using anhydrous sodium sulfate and distilled under reduced pressure. The resulting residue was purified by basic silica gel column chromatography to obtain the title compound (0.55 g).

[Intermediate 12] trans-1-ethynyl-4-methoxycyclohexane

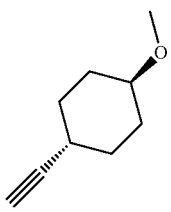

The title compound (250 mg) was obtained by performing the same reactions as in Intermediate 11, except that trans-4-ethynylcyclohexan-1-ol (300 mg, 2.42 mmol) was used instead of t-butyl-(trans-4-ethynylcyclohexyl)carbamate.

[Synthesis Example 1] 6-((4,6-dimethyl-2-oxo-1,2-dihydropyridin-3-yl)methyl)-2(trans-4-(dimethylamino)cyclohexyl)-2,4-dimethyl-7,8-dihydro-[1,3]dioxolo[4,5-g]isoquinolin-5(6H)-one [Compound 1]

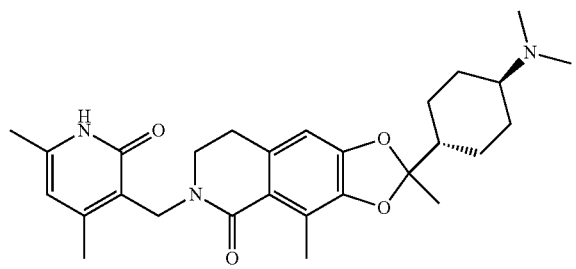

Step 1. Production of 2-(trans-4-(dimethylamino)cyclohexyl)-2,4-dimethyl-7,8-dihydro-[1,3]dioxolo[4,5-g]isoquinolin-5(6H)-one

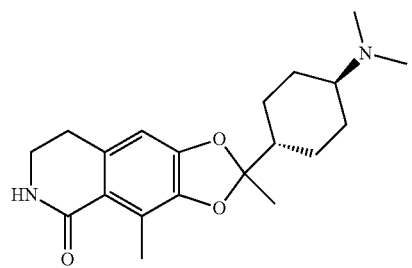 [SMILES: Cc1c2c(cc3c1C(=O)NCC3)OC(C)([C@H]1CC[C@H](N(C)C)CC1)O2]

6,7-dihydroxy-8-methyl-3,4-dihydroisoquinolin-1(2H)-one (61 mg, 0.3 mmol, Intermediate 1), $Ru_3(CO)_{12}$ (5 mg, 0.008 mmol) and Bippyphos (12 mg, 0.02 mmol) were added to 1,4-dioxane (1 ml), and argon gas replacement was performed, followed by refluxing at 120° C. for 10 minutes. A solution of trans-4-ethynyl-N,N-dimethylcyclohexan-1-amine (95 mg, 0.6 mmol, Intermediate 8) dissolved in 1,4-dioxane (0.3 ml) was added dropwise thereto, and then the mixture was refluxed at 120° C. for 36 hours. The reaction solution was cooled to room temperature and then concentrated under reduced pressure. The resulting residue was purified by silica gel column chromatography to obtain the title compound (24 mg).

Step 2. Production of 6-((2-(benzyloxy)-4,6-dimethylpyridin-3-yl)methyl)-2-(trans-4-(dimethylamino)cyclohexyl)-2,4-dimethyl-7,8-dihydro-[1,3]dioxolo[4,5-g]isoquinolin-5(6H)-one

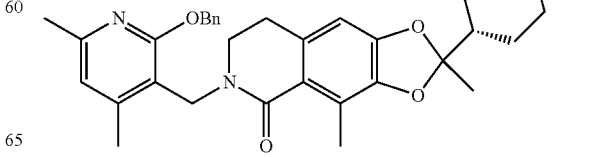

2-(trans-4-(dimethylamino)cyclohexyl)-2,4-dimethyl-7,8-dihydro-[1,3]dioxolo[4,5-g]isoquinolin-5(6H)-one (24 mg, 0.07 mmol) synthesized in Step 1 above was added to N,N-dimethylformamide (0.7 ml). The reaction solution was cooled to 0° C., and then 1.0M potassium t-butoxide (90 μl, 0.09 mmol) was added dropwise thereto, followed by stirring for 5 minutes. 2-(benzyloxy)-3-(chloromethyl)-4,6-dimethylpyridine (24 mg, 0.09 mmol) synthesized according to the method described in WO2014097041 was dissolved in N,N-dimethylformamide (0.3 ml) and was added to the mixture, followed by stirring at 0° C. for 1 hour. After completion of the reaction, ammonium chloride solution was added to the reaction solution, followed by extraction using 10% methanol-chloroform. The extracted organic layer was dried using anhydrous sodium sulfate and distilled under reduced pressure. The resulting residue was purified by basic silica gel column chromatography to obtain the title compound (20 mg).

Step 3. Production of 6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one

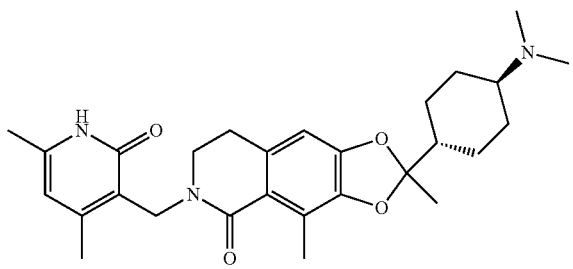

6-((2-(benzyloxy)-4,6-dimethylpyridin-3-yl)methyl)-2-(trans-4-(dimethylamino)cyclohexyl-2,4-dimethyl-7,8-dihydro-[1,3]dioxolo[4,5-g]isoquinolin-5(6H)-one (20 mg, 0.03 mmol) synthesized in Step 2 above was added to dichloromethane (0.5 ml). 4M hydrochloric acid-1,4-dioxane solution (0.2 ml, 0.8 mmol) was added to the reaction solution, followed by stirring at room temperature for 3 hours. After completion of the reaction, the reaction solution was neutralized by adding saturated aqueous sodium bicarbonate solution and extracted using 20% methanol-chloroform. The extracted organic layer was dried using anhydrous sodium sulfate and concentrated under reduced pressure. The resulting residue was purified by basic silica gel column chromatography to obtain the title compound (9 mg).

[Synthesis Example 2] 6-((4,6-dimethyl-2-oxo-1,2-dihydropyridin-3-yl)methyl)-2(trans-4-(dimethylamino)cyclohexyl)-2-methyl-7,8-dihydro-[1,3]dioxolo[4,5-g]isoquinolin-5(6H)-one [Compound 2]

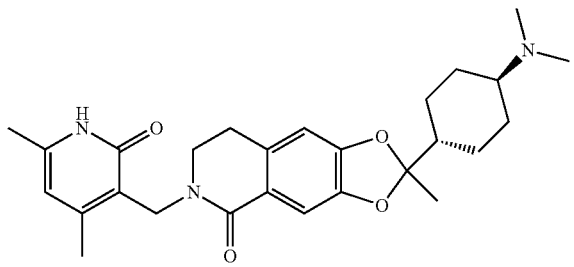

Step 1. Production of t-butyl (trans-4-(2-methyl-5-oxo-5,6,7,8-tetrahydro-[1,3]dioxolo[4,5-g]isoquinolin)-2-yl)cyclohexyl)carbamate

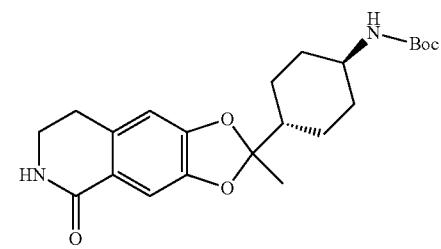 [SMILES: CC(C)(C)OC(=O)N[C@H]1CC[C@H](C2(C)Oc3cc4c(cc3O2)C(=O)NCC4)CC1]

6,7-dihydroxy-3,4-dihydroisoquinolin-1(2H)-one (190 mg, 1.06 mmol, Intermediate 2), t-butyl-(trans-4-ethynylcyclohexyl)carbamate (355 mg, 1.59 mmol), Ru$_3$(CO)$_{12}$ (34 mg, 0.05 mmol) and Bippyphos (81 mg, 0.16 mmol) were sequentially added to 1,4-dioxane (9.5 ml), and argon gas replacement was performed, followed by refluxing at 120° C. for 16 hours. The reaction solution was cooled to room temperature and then concentrated under reduced pressure. The resulting residue was purified by silica gel column chromatography to obtain the title compound (320 mg).

Step 2. Production of t-butyl (trans-4-(6-((2-(benzyloxy)-4,6-dimethylpyridin-3-yl)methyl)-2-methyl-5-oxo-5,6,7,8-tetrahydro-[1,3]dioxolo[4,5-g]isoquinolin-2-yl)cyclohexyl)carbamate

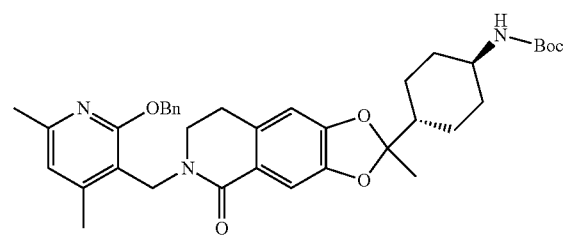 [SMILES: Cc1cc(C)c(CN2CCc3cc4c(cc3C2=O)OC(C)([C@H]2CC[C@H](NC(=O)OC(C)(C)C)CC2)O4)c(OCc2ccccc2)n1]

The title compound (225 mg) was obtained by performing the same reaction as in Step 2 of Synthesis Example 1, except that t-butyl(trans-4-(2-methyl-5-oxo-5,6,7,8-tetrahydro-[1,3]dioxolo[4,5-g]isoquinolin-2-yl)cyclohexyl)carbamate (320 mg, 0.77 mmol) synthesized in Step 1 above was used instead of 2-(trans-4-(dimethylamino)cyclohexyl)-2,4-dimethyl-7,8-dihydro-[1,3]dioxolo[4,5-g]isoquinolin-5(6H)-one.

Step 3. Production of t-butyl(trans-4-(6-((4,6-dimethyl-2-oxo-1,2-dihydropyridin-3-yl)methyl)-2-methyl-5-oxo-5,6,7,8-tetrahydro-[1,3]dioxolo[4,5-g]isoquinolin-2-yl)cyclohexyl)carbamate

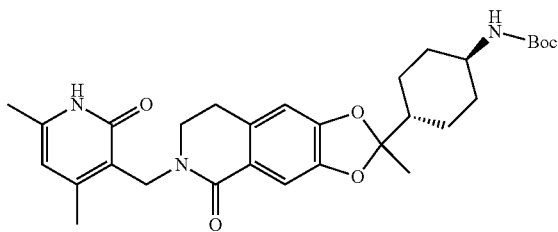 [SMILES: Cc1cc(C)c(CN2CCc3cc4c(cc3C2=O)OC(C)([C@H]2CC[C@H](NC(=O)OC(C)(C)C)CC2)O4)c(=O)[nH]1]

t-butyl(trans-4-(6-((2-(benzyloxy)-4,6-dimethylpyridin-3-yl)methyl)-2-methyl-5-oxo-5,6,7,8-tetrahydro-[1,3]dioxolo[4,5-g]isoquinolin-2-yl)cyclohexyl)carbamate (225 mg, 0.36 mmol) synthesized in Step 2 above and 10% palladium/carbon (25 mg) were added to methanol (5 ml), and then a hydrogen balloon was attached. The reaction solution was stirred at room temperature for 2 hours, filtered through celite, and distilled under reduced pressure to obtain the title compound (212 mg).

Step 4. Production of 2-(trans-4-aminocyclohexyl)-6-((4,6-dimethyl-2-oxo-1,2-dihydropyridin-3-yl)methyl)-2-methyl-7,8-dihydro-[1,3]dioxolo[4,5-g]isoquinolin-5(6H)-one

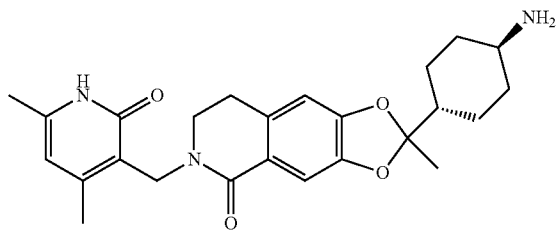 [SMILES: Cc1cc(C)c(CN2CCc3cc4c(cc3C2=O)OC(C)([C@H]2CC[C@H](N)CC2)O4)c(=O)[nH]1]

t-butyl(trans-4-(6-((4,6-dimethyl-2-oxo-1,2-dihydropyridin-3-yl)methyl)-2-methyl-5-oxo-5,6,7,8-tetrahydro-[1,3]dioxolo[4,5-g]isoquinolin-2-yl)cyclohexyl)carbamate (200 mg 0.37 mmol) synthesized in Step 3 above and 4M hydrochloric acid-1,4-dioxane solution (2 ml) were sequentially added to methanol (5 ml), and then the reaction solution was stirred at room temperature for 1 hour. After completion of the reaction, the reaction solution was neutralized by adding saturated aqueous sodium bicarbonate solution and extracted using 20% methanol-chloroform. The extracted organic layer was dried using anhydrous sodium sulfate and concentrated under reduced pressure, and the resulting residue was purified by basic silica gel column chromatography to obtain the title compound (182 mg).

Step 5. 6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one [Compound 3]

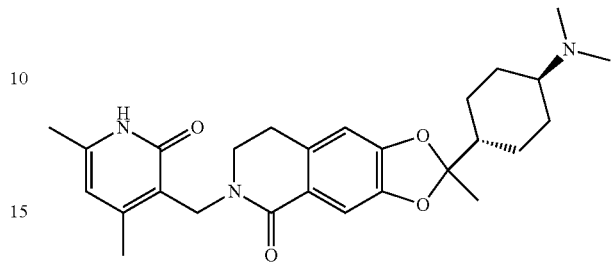

2-(trans-4-aminocyclohexyl)-6-((4,6-dimethyl-2-oxo-1,2-dihydropyridin-3-yl)methyl)-2-methyl-7,8-dihydro-[1,3]dioxolo[4,5-g]isoquinolin-5(6H)-one (160 mg, 0.37 mmol) synthesized in Step 4 above and 37% formaldehyde aqueous solution (67 µl, 0.8 mmol) were sequentially added to methanol (4 ml). The mixture was stirred at room temperature for 10 minutes, and sodium triacetoxyboron hydride (388 mg, 1.83 mmol) was added thereto, followed by stirring at room temperature for 18 hours. After completion of the reaction, the reaction solution was neutralized with sodium bicarbonate and extracted using 20% methanol-chloroform. The extracted organic layer was washed with brine, dried using anhydrous sodium sulfate, and distilled under reduced pressure. The resulting residue was purified by basic silica gel column chromatography to obtain the title compound (112 mg).

[Synthesis Example 3] 6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one [Compound 3]

The title compound (30 mg) was obtained by performing the same reactions as in Synthesis Example 2, except that 6,7-dihydroxy-5-methyl-dihydroisoquinolin-1(2H)-one (Intermediate 6) was used instead of 6,7-dihydroxy-3,4-dihydroisoquinolin-1(2H)-one in Step 1 of Synthesis Example 2.

[Synthesis Example 4] 4-chloro-6-((4,6-dimethyl-2-oxo-1,2-dihydropyridin-3-yl)methyl)-2-(trans-4-(dimethyl)amino)cyclohexyl)-2,9-dimethyl-7,8-dihydro-[1,3]dioxolo[4,5-g]isoquinolin-5(6H)-one [Compound 4]

The title compound (160 mg) was obtained by performing the same reactions as in Synthesis Example 2, except that 8-chloro-6,7-dihydroxy-5-methyl-3,4-dihydroisoquinolin-1(2H)-one [Intermediate 5] was used instead of 6,7-dihydroxy-3,4-dihydroisoquinolin-1(2H)-one in Step 1 of Synthesis Example 2.

[Synthesis Example 5] Production of 4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one isomers A and B [Compounds 5 and Compound 6]

4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one [Compound 4] synthesized in Synthesis Example 4 was separated into enantiomers under the following conditions. The absolute stereochemistry of each isomer was not determined.

Column: Daicel Chiralcel OZ-H, 4.6×250 mm, 5 μM
Temperature: 35° C.
Flow rate: 0.8 ml/min
Wavelength: 270 nm
Elution solvent: n-hexane:ethanol:diethylamine=500:500:0.4 (v/v %)
First peak: 17.9 min—isomer A (99.9% ee)
Second peak: 28.3 min—isomer B (99.9% ee)

[Synthesis Example 6] 4,9-dichloro-6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one [Compound 7]

The title compound (1.8 mg) was obtained by performing the same reactions as in Synthesis Example 2, except that 5,8-dichloro-6,7-dihydroxy-5-methyl-3,4-dihydroisoquinolin-1(2H)-one [Intermediate 7] was used instead of 6,7-dihydroxy-3,4-dihydroisoquinolin-1(2H)-one in Step 1 of Synthesis Example 2.

TABLE 1

| Structure # / $^1$H-NMR Spectrum (300 MHz) | Nomenclature | MS[M + H]$^+$ |
|---|---|---|
| 1 | 6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 480.3 |
| $^1$H-NMR spectrum (300 MHz, CDCl$_3$) δ 6.33(s, 1H), 5.91(s, 1H), 4.79(s, 2H), 3.70-3.42(m, 2H), 2.70-2.65(m, 2H), 2.53(s, 3H), 2.27(s, 12H), 2.24-2.19(m, 1H), 2.01-1.95(m, 4H), 1.65-1.62(m, 1H), 1.55(s, 3H), 0.90-0.83(m, 4H). | | |
| 2 | 6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one | 466.3 |
| $^1$H-NMR spectrum (300 MHz, CDCl$_3$) δ 11.92(bs, 1H), 7.44(s, 1H), 6.46(s, 1H), 5.92(s, 1H), 4.75(s, 2H), 3.58(t, 2H), 2.74(t, 2H), 2.40-2.05(m, 13H), 2.10-1.80(m, 4H), 1.70-1.62(m, 1H), 1.56(s, 3H), 1.40-1.05(m, 4H). | | |
| 3 | 6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one | 480.3 |
| $^1$H-NMR spectrum (300 MHz, CDCl$_3$) δ 11.67(brs, 1H), 7.36(s, 1H), 5.91(s, 1H), 4.76(2H, d), 3.59(t, 2H), 2.69(t, 2H), 2.30(s, 3H), 2.28(d, 9H), 2.16(m, 1H), 2.09(s, 3H), 1.97(m, 4H), 1.75(m, 1H), 1.57(s, 3H), 1.25(m, 4H). | | |

TABLE 1-continued

| Structure # | Nomenclature / ¹H-NMR Spectrum (300 MHz) | MS[M + H]⁺ |
|---|---|---|
| 4 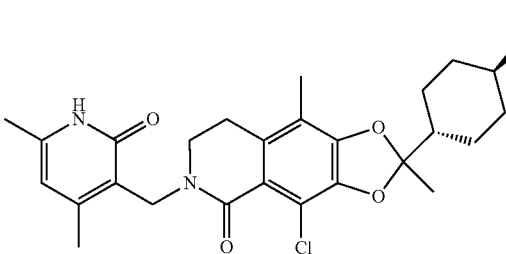 | 4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one | 514.2 |

¹H-NMR spectrum (300 MHz CDCl₃) δ 11.30(brs, 1H), 5.91(s, 1H), 4.77(d, 2H), 3.55(t, 2H), 2.65(t, 2H), 2.34(s, 3H), 2.27(d, 9H), 2.15(m, 1H), 2.06(s, 3H), 1.98(m, 4H), 1.81(m, 1H), 1.62(s, 3H), 1.27-1.23(m, 4H).

| Structure # | Nomenclature | MS[M + H]⁺ |
|---|---|---|
| 5 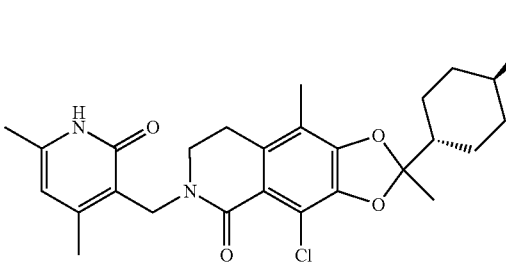 | 4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one isomer A | 514.2 |

¹H-NMR was not measured due to limited quantities.

| Structure # | Nomenclature | MS[M + H]⁺ |
|---|---|---|
| 6 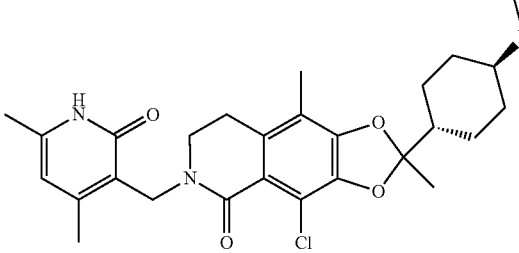 | 4-chloro-6-((4,6-dimethyl-2-oxo-1,2-dihydropyridin-3-yl)methyl)-2-(trans-4-(dimethylamino)cyclohexyl)-2,9-dimethyl-7,8-dihydro-[1,3]dioxolo[4,5-g]isoquinolin-5(6H)-one isomer B | 514.2 |

¹H-NMR was not measured due to limited quantities.

| Structure # | Nomenclature | MS[M + H]⁺ |
|---|---|---|
| 7 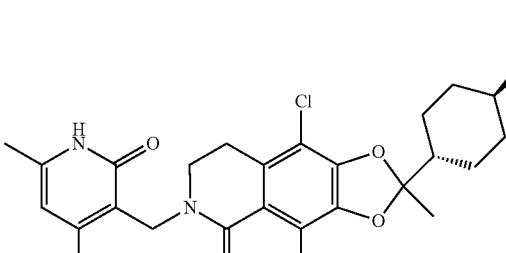 | 4,9-dichloro-6-((4,6-dimethyl-2-oxo-1,2-dihydropyridin-3-yl)methyl)-2-(trans-4-(dimethylamino)cyclohexyl)-2-methyl-7,8-dihydro-[1,3]dioxolo[4,5-g]isoquinolin-5(6H)-one | 534.2 |

¹H-NMR spectrum (300 MHz, CDCl₃) δ 11.2(bs, 1H), 5.91(s, 1H), 4.74(s, 2H), 3.59(t, 2H), 2.83(t, 2H), 2.33(s, 3H), 2.30(s, 6H), 2.26(s, 3H), 2.22(t, 1H), 2.01-1.98(m, 4H), 1.85(t, 1H), 1.67(s, 3H), 1.31-1.22(m, 4H).

[Synthesis Example 7] 2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one [Compound 8] and 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one racemate [Compound 9]

Step 1. Production of t-butyl-((trans-4-(2,4-dimethyl-5-oxo-5,6,7,8-tetrahydro-[1,3]dioxolo[4,5-g]isoquinolin-2-yl)cyclohexyl)carbamate

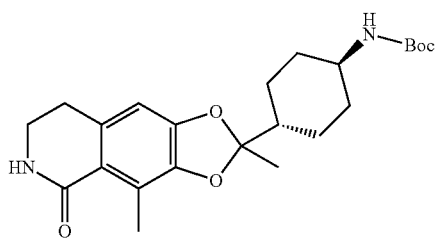 [SMILES: Cc1c2c(cc3c1C(=O)NCC3)OC(C)([C@H]1CC[C@H](NC(=O)OC(C)(C)C)CC1)O2]

6,7-dihydroxy-8-methyl-3,4-dihydroisoquinolin-1(2H)-one (2.5 g, 12.9 mmol, Intermediate 1), t-butyl-(trans-4-ethynylcyclohexyl)carbamate (7.2 g, 32.2 mmol), Ru₃(CO)₁₂ (415 mg, 0.65 mmol) and Bippyphos (985 mg, 1.94 mmol) were sequentially added to 1,4-dioxane (125 ml), and argon gas replacement was performed, followed by refluxing at 120° C. for 16 hours. The reaction solution was cooled to room temperature and then concentrated under reduced pressure. The resulting residue was purified by silica gel column chromatography to obtain the title compound (3.59 g).

Step 2. Production of t-butyl-((trans-4-(9-chloro-2,4-dimethyl-5-oxo-5,6,7,8-tetrahydro-[1,3]dioxolo[4,5-g]isoquinolin-2-yl)cyclohexyl)carbamate

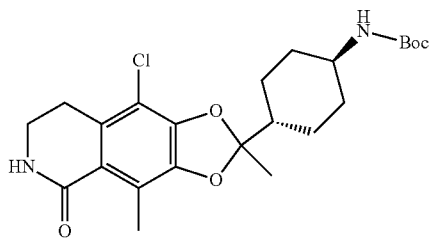 [SMILES: Cc1c2c(c(Cl)c3c1C(=O)NCC3)OC(C)([C@H]1CC[C@H](NC(=O)OC(C)(C)C)CC1)O2]

t-butyl-((trans-4-(2,4-dimethyl-5-oxo-5,6,7,8-tetrahydro-[1,3]dioxolo[4,5-g]isoquinolin-2-yl)cyclohexyl)carbamate (885 mg, 2.1 mmol) synthesized in Step 1 above was added to acetic acid (10 ml), and then N-chlorosuccinimide (567 mg, 4.3 mmol) was added thereto. The reaction solution was heated to 70° C. and stirred for 1 hour. After completion of the reaction, the reaction solution was cooled to room temperature, neutralized by adding saturated aqueous sodium bicarbonate solution, and extracted using ethyl acetate. The extracted organic layer was dried over anhydrous sodium sulfate and distilled under reduced pressure. The obtained residue was purified by silica gel column chromatography to obtain the title compound (356 mg).

Step 3. Production of t-butyl-((trans-4-(6-((2-(benzyloxy)-4,6-dimethylpyridin-3-yl)methyl)-9-chloro-2,4-dimethyl-5-oxo-5,6,7,8-tetrahydro-[1,3]dioxolo[4,5-g]isoquinolin-2-yl)cyclohexyl)carbamate

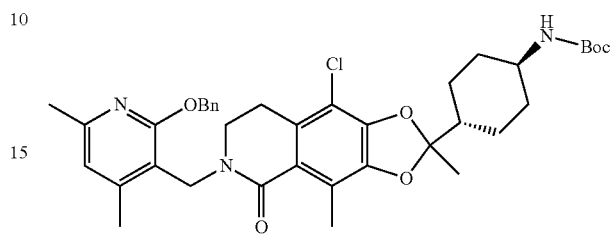

The title compound (150 mg) was obtained by performing the same reaction as in Step 2 of Synthesis Example 2 using t-butyl-((trans-4-(9-chloro-2,4-dimethyl-5-oxo-5,6,7,8-tetrahydro-[1,3]dioxolo[4,5-g]isoquinolin-2-yl)cyclohexyl)carbamate (150 mg, 0.33 mmol) synthesized in Step 2 above.

Step 4. Production of t-butyl-(trans-4-(9-chloro-6-((4,6-dimethyl-2-oxo-1,2-dihydropyridin-3-yl)methyl)-2,4-dimethyl-5-oxo-5,6,7,8-tetrahydro-[1,3]dioxolo[4,5-g]isoquinolin-2-yl)cyclohexyl)carbamate

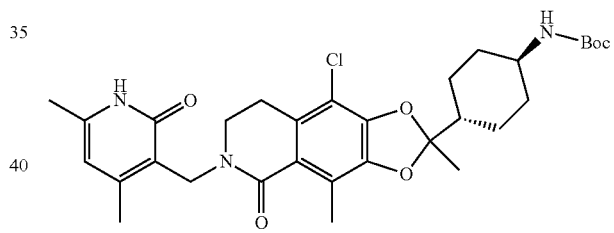

The title compound (120 mg) was obtained by performing the same reaction as in Step 3 of Synthesis Example 2 using t-butyl-((trans-4-(6-((2-(benzyloxy)-4,6-dimethylpyridin-3-yl)methyl)-9-chloro-2,4-dimethyl-5-oxo-5,6,7,8-tetrahydro-[1,3]dioxolo[4,5-g]isoquinolin-2-yl)cyclohexyl)carbamate (150 mg, 0.22 mmol) synthesized in Step 3 above.

Step 5. Production of 2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one [Compound 8]

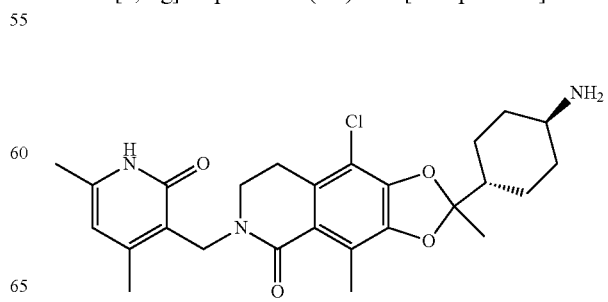

t-butyl-(trans-4-(9-chloro-6-((4,6-dimethyl-2-oxo-1,2-dihydropyridin-3-yl)methyl)-2,4-dimethyl-5-oxo-5,6,7,8-tetrahydro-[1,3]dioxolo[4,5-g]isoquinolin-2-yl)cyclohexyl)carbamate (120 mg, 0.20 mmol) synthesized in Step 4 above and 4M hydrochloric acid-1,4-dioxane solution (2 ml) were sequentially added to methanol, and then the reaction solution was stirred at room temperature for 2 hours. After completion of the reaction, the reaction solution was neutralized by adding saturated aqueous sodium bicarbonate solution and extracted using 20% methanol-chloroform. The extracted organic layer was dried using anhydrous sodium sulfate and concentrated under reduced pressure to obtain the title compound (91 mg).

Step 6. Production of 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 9]

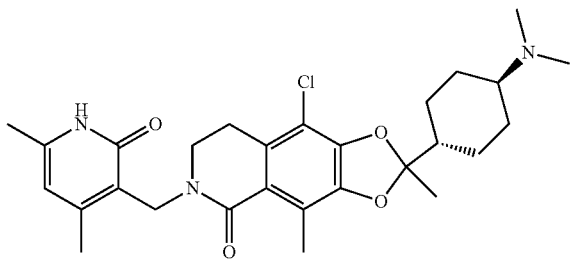

2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one (90.6 mg, 0.19 mmol) synthesized in Step 5 above and 37% formaldehyde aqueous solution (31 μl, 0.41 mmol) were sequentially added to methanol (2 ml), followed by stirring at room temperature for 10 minutes. Sodium triacetoxyboron hydride (197 mg, 0.93 mmol) was added to the reaction mixture, followed by stirring at room temperature for 18 hours. After completion of the reaction, the reaction solution was neutralized with 1M aqueous sodium hydroxide solution and extracted using 20% methanol-chloroform. The extracted organic layer was washed with brine, dried using anhydrous sodium sulfate, and distilled under reduced pressure. The resulting residue was purified by basic silica gel column chromatography to obtain the title compound (50 mg).

[Synthesis Example 8] 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomers A and B [Compound 10 and Compound 11]

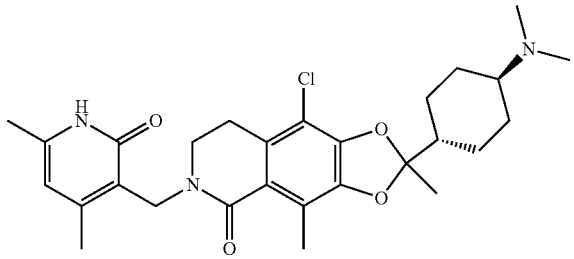

9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 9] synthesized in Synthesis Example 7 was separated into enantiomers under the following conditions. The absolute stereochemistry of each isomer was not determined.

Column: Daicel Chiralcel OZ-H, 4.6×250 mm, 5 μM
Temperature: 35° C.
Flow rate: 0.9 ml/min
Wavelength: 270 nm
Elution solvent: n-hexane:ethanol:diethylamine=600:400:0.4 (v/v %)
First peak: 13.7 min—isomer A (99.9% ee)
Second peak: 22.0 min—isomer B (99.9% ee)

[Synthesis Example 9] 9-chloro-6-((4,6-dimethyl-2-oxo-1,2-dihydropyridin-3-yl)methyl)-2-(cis-4-(dimethylamino)cyclohexyl)-2,4-dimethyl-7,8-dihydro-[1,3]dioxolo[4,5-g]isoquinolin-5(6H)-one [Compound 12]

The title compound (25 mg) was obtained by performing the same reactions as in Synthesis Example 7, except that t-butyl-(cis-4-ethynylcyclohexyl)carbamate [Intermediate 9] was used instead of t-butyl-(trans-4-ethynylcyclohexyl)carbamate in Step 1 of Synthesis Example 7.

[Synthesis Example 10] 9-chloro-2-(trans-4-(dimethylamino)cyclohexyl)-6-((4-methoxy-6-methyl-2-oxo-1,2-dihydropyridin-3-yl)methyl)-2,4-dimethyl-7,8-dihydro-[1,3]dioxolo[4,5-g]isoquinolin-5(6H)-one [Compound 13]

The title compound (31 mg) was obtained by performing the same reactions as in Synthesis Example 7, except that 2-(benzyloxy)-3-(chloromethyl)-4-methoxy-6-methylpyridine was used instead of 2-(benzyloxy)-3-(chloromethyl)-4,6-dimethylpyridine in Step 3 of Synthesis Example 7.

[Synthesis Example 11] 9-chloro-2-(trans-4-(dimethylamino)cyclohexyl)-2,4-dimethyl-6-((6-methyl-2-oxo-4-propyl-1,2-dihydropyridin-3-yl)methyl)-7,8-dihydro-[1,3]dioxolo[4,5-g]isoquinolin-5(6H)-one [Compound 14]

The title compound (50 mg) was obtained by performing the same reactions as in Synthesis Example 7, except that 2-(benzyloxy)-3-(chloromethyl)-6-methyl-4-propylpyridine was used instead of 2-(benzyloxy)-3-(chloromethyl)-4,6-dimethylpyridine in Step 3 of Synthesis Example 7.

[Synthesis Example 12] 9-chloro-6-((4,6-dimethyl-2-oxo-1,2-dihydropyridin-3-yl)methyl)-2-(trans-4-(ethylamino)cyclohexyl)-2,4-dimethyl-7,8-dihydro-[1,3]dioxolo[4,5-g]isoquinolin-5(6H)-one [Compound 15]

The title compound (12 mg) was obtained by performing the same reaction as in Step 6 of Synthesis Example 7, except that acetaldehyde (1 eq.) was used instead of 37% formaldehyde aqueous solution in Step 6 of Synthesis Example 7.

[Synthesis Example 13] 9-chloro-2-(trans-4-(diethylamino)cyclohexyl)-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one [Compound 16]

The title compound (34 mg) was obtained by performing the same reaction as in Step 6 of Synthesis Example 7, except that acetaldehyde (1.5 eq.) was used instead of 37% formaldehyde aqueous solution in Step 6 of Synthesis Example 7.

[Synthesis Example 14] 9-chloro-6-((4,6-dimethyl-2-oxo-1,2-dihydropyridin-3-yl)methyl)-2,4-dimethyl-2-(trans-4-(piperidin-1-yl)cyclohexyl)-7,8-dihydro-[1,3]dioxolo[4,5-g]isoquinolin-5(6H)-one [Compound 17]

2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one (21 mg, 0.043 mmol) synthesized in Step 5 of Synthesis Example 7 was added to N,N-dimethylformamide (0.5 ml), and then potassium carbonate (30 mg, 0.215 mmol) and 1,5-dibromopentane (7 µl, 0.052 mmol) were sequentially added thereto. The reaction solution was stirred at room temperature for 17 hours and then extracted using water and 20% methanol-chloroform. The extracted organic layer was dried using anhydrous sodium sulfate and concentrated under reduced pressure. The resulting residue was purified by basic silica gel column chromatography to obtain the title compound (12.2 mg).

[Synthesis Example 15] 9-chloro-6-((4,6-dimethyl-2-oxo-1,2-dihydropyridin-3-yl)methyl)-2,4-dimethyl-2-(trans-4-(pyrrolidin-1-yl)cyclohexyl)-7,8-dihydro-[1,3]dioxolo[4,5-g]isoquinolin-5(6H)-one [Compound 18]

The title compound (5.6 mg) was obtained by performing the same reactions as in Synthesis Example 14, except that 1,4-dibromobutane was used instead of 1,5-dibromobutane in Synthesis Example 14.

[Synthesis Example 16] (2S)—N-(trans-4-(9-chloro-6-((4,6-dimethyl-2-oxo-1,2-dihydropyridin-3-yl))methyl)-2,4-dimethyl-5-oxo-5,6,7,8-tetrahydro-[1,3]dioxolo[4,5-g]isoquinolin-2-yl)cyclohexyl)-2-hydroxybutanamide [Compound 19]

2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one (21 mg, 0.043 mmol) synthesized in Step 5 of Synthesis Example 7, (R)-2-hydroxybutanoic acid (4.2 mg, 0.04 mmol), 1-ethyl-3-(3-dimethylaminopropyl)carbodiimide hydrochloride (11 mg, 0.057 mmol) and hydroxybenzotriazole (7.3 mg, 0.054 mmol) were sequentially added to N,N-dimethylformamide (0.5 ml), followed by stirring at room temperature for 18 hours. Ice water was added to the reaction solution, the resulting solid was collected by filtration and purified by basic silica gel column chromatography to obtain the title compound (9 mg).

[Synthesis Example 17] 2-((trans-4-aminocyclohexyl)methyl)-9-chloro-6-((4,6-dimethyl-2-oxo-1,2-dihydropyridin-3)-yl)methyl)-2,4-dimethyl-7,8-dihydro-[1,3]dioxolo[4,5-g]isoquinolin-5(6H)-one [Compound 20] and 9-chloro-6-((4,6-dimethyl-2-oxo-1,2-dihydropyridin-3-yl)methyl)-2-((trans-4-(dimethylamino)cyclohexyl)methyl)-2,4-dimethyl-7,8-dihydro-[1,3]dioxolo[4,5-g]isoquinolin-5(6H)-one [Compound 21]

The title compounds (9 mg of Compound 20 and 5 mg of Compound 21) were each obtained by performing the same reactions as in Synthesis Example 7, except that t-butyl-(trans-4-(propyn-2-yl)cyclohexyl)carbamate was used instead of t-butyl-(trans-4-ethynylcyclohexyl)carbamate in Step 1 of Synthesis Example 7.

[Synthesis Example 18] 9-chloro-2-cyclohexyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one [Compound 22]

The title compound (36 mg) was obtained by performing the same reactions as in Step 1 to Step 4 of Synthesis Example 7, except that ethynylcyclohexane was used instead of t-butyl-(trans-4-ethynylcyclohexyl)carbamate in Step 1 of Synthesis Example 7.

[Synthesis Example 19] 9-chloro-2-cyclopentyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one [Compound 23]

The title compound (58 mg) was obtained by performing the same reactions as in Step 1 to Step 4 of Synthesis Example 7, except that ethynylcyclopentane was used instead of t-butyl-(trans-4-ethynylcyclohexyl)carbamate in Step 1 of Synthesis Example 7.

[Synthesis Example 20] 9-chloro-6-((4,6-dimethyl-2-oxo-1,2-dihydropyridin-3-yl)methyl)-2,4-dimethyl-2-(tetrahydro-2H-pyran-4-yl)-7,8-dihydro-[1,3]dioxolo[4,5-g]isoquinolin-5(6H)-one [Compound 24]

The title compound (23 mg) was obtained by performing the same reactions as in Step 1 to Step 4 of Synthesis Example 7, except that 4-ethynyltetrahydro-2H-pyran was used instead of t-butyl-(trans-4-ethynylcyclohexyl)carbamate in Step 1 of Synthesis Example 7.

[Synthesis Example 21] 9-chloro-6-((4,6-dimethyl-2-oxo-1,2-dihydropyridin-3-yl)methyl)-2-(4-(dimethylamino)phenyl)-2,4-dimethyl-7,8-dihydro-[1,3]dioxolo[4,5-g]isoquinolin-5(6H)-one [Compound 25]

The title compound (18 mg) was obtained by performing the same reactions as in Synthesis Example 7, except that 5-chloro-6,7-dihydroxy-8-methyl-3,4-dihydroisoquinolin-1 (2H)-one [Intermediate 4] and 4-ethynyl-N,N-dimethylaniline were used instead of 6,7-dihydroxy-8-methyl-3,4-dihydroisoquinolin-1(2H)-one and t-butyl-(trans-4-ethynylcyclohexyl)carbamate, respectively, in Step 1 of Synthesis Example 7.

[Synthesis Example 22] 9-chloro-6-((4,6-dimethyl-2-oxo-1,2-dihydropyridin-3-yl)methyl)-2-(4-(dimethylamino)butyl)-2,4-dimethyl-7,8-dihydro-[1,3]dioxolo[4,5-g]isoquinolin-5(6H)-one [Compound 26]

The title compound (5.9 mg) was obtained by performing the same reactions as in Synthesis Example 21, except that N,N-dimethylhex-5-yn-1-amine was used instead of 4-ethynyl-N,N-dimethylaniline in Synthesis Example 21.

[Synthesis Example 23] 9-chloro-6-((4,6-dimethyl-2-oxo-1,2-dihydropyridin-3-yl)methyl)-2-(3,5-(dimethylisoxazol-4-yl)-2,4-dimethyl-7,8-dihydro-[1,3]dioxolo[4,5-g]isoquinolin-5(6H)-one [Compound 27]

The title compound (40 mg) was obtained by performing the same reactions as in Synthesis Example 7, except that 4-ethynyl-3,5-dimethylisoxazole was used instead of t-butyl-(trans-4-ethynylcyclohexyl)carbamate in Step 1 of Synthesis Example 7.

[Synthesis Example 24] 9-chloro-6-((4,6-dimethyl-2-oxo-1,2-dihydropyridin-3-yl)methyl)-2,4-dimethyl-2-(piperidin-4-yl)-7,8-dihydro-[1,3]dioxolo[4,5-g]isoquinolin-5(6H)-one [Compound 28] and 9-chloro-6-((4,6-dimethyl-2-oxo-1,2-dihydropyridin-3-yl)methyl)-2,4-dimethyl-2-(1-methylpiperidin-4-yl)-7,8-dihydro-[1,3]dioxolo[4,5-g]isoquinolin-5 (6H)-one [Compound 29]

The title compounds (125 mg of Compound 28 and 30 mg of Compound 29) were each obtained by performing the same reactions as in Synthesis Example 7, except that t-butyl-4-ethynylpiperidine-1-carboxylate was used instead of t-butyl-(trans-4-ethynylcyclohexyl)carbamate in Step 1 of Synthesis Example 7.

[Synthesis Example 25] 9-chloro-6-((4,6-dimethyl-2-oxo-1,2-dihydropyridin-3-yl)methyl)-2-(1-((R)-2-hydroxybutanoyl)piperidin-4-yl)-2,4-dimethyl-7,8-dihydro-[1,3]dioxolo[4,5-g]isoquinolin-5(6H)-one [Compound 30]

The title compound (21 mg) was obtained by performing the same reactions as in Synthesis Example 16, except that 9-chloro-6-((4,6-dimethyl-2-oxo-1,2-dihydropyridin-3-yl)methyl)-2,4-dimethyl-2-(piperidin-4-yl)-7,8-dihydro-[1,3]dioxolo[4,5-g]isoquinolin-5(6H)-one [Compound 28] synthesized in Synthesis Example 24 was used instead of 2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one in Synthesis Example 16.

[Synthesis Example 26] 9-chloro-6-((4,6-dimethyl-2-oxo-1,2-dihydropyridin-3-yl)methyl)-2,4-dimethyl-2-(1-(2,2,2-trifluoroethyl)piperidin-4-yl)-7,8-dihydro-[1,3]dioxolo[4,5-g]isoquinolin-5(6H)-one [Compound 31]

9-chloro-6-((4,6-dimethyl-2-oxo-1,2-dihydropyridin-3-yl)methyl)-2,4-dimethyl-2-(piperidin-4-yl)-7,8-dihydro-[1,3]dioxolo[4,5-g]isoquinolin-5(6H)-one (20 mg, 0.04 mmol, Compound 28) synthesized in Synthesis Example 24, potassium carbonate (16 mg, 0.12 mmol) and 1,1,1-trifluoro-2-iodomethane (19.6 mg, 0.10 mmol) were sequentially added to N,N-dimethylformamide (1.0 ml). The reaction solution was refluxed at 90° C. for 18 hours. After the reaction solution was cooled to room temperature, 20% methanol-chloroform and water were added thereto, and the organic layer was extracted. The extracted organic layer was dried using anhydrous sodium sulfate and distilled under reduced pressure. The resulting residue was purified by basic silica gel column chromatography to obtain the title compound (2.5 mg).

[Synthesis Example 27] 9-chloro-6-((4,6-dimethyl-2-oxo-1,2-dihydropyridin-3-yl)methyl)-2,4-dimethyl-2-(1-methyl-1H-indol-5-yl)-7,8-dihydro-[1,3]dioxolo[4,5-g]isoquinolin-5(6H)-one [Compound 32]

The title compound (109 mg) was obtained by performing the same reactions as in Synthesis Example 21, except that 5-ethynyl-1-methyl-TH-indole synthesized according to the method described in WO2016154434 was used instead of 4-ethynyl-N,N-dimethylaniline in Synthesis Example 21.

[Synthesis Example 28] 9-chloro-6-((4,6-dimethyl-2-oxo-1,2-dihydropyridin-3-yl)methyl)-2-(trans-4-methoxycyclohexyl)-2,4-dimethyl-7,8-dihydro-[1,3]dioxolo[4,5-g]isoquinolin-5(6H)-one [Compound 33]

The title compound (50 mg) was obtained by performing the same reactions as in Synthesis Example 21, except that trans-1-ethynyl-4-methoxycyclohexane was used instead of 4-ethynyl-N,N-dimethylaniline in Synthesis Example 21.

[Synthesis Example 29] 9-chloro-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one [Compound 34]

The title compound (35 mg) was obtained by performing the same reactions as in Step 1 to Step 5 of Synthesis Example 7, except that t-butyl-(trans-ethynylcyclohexyl)(methyl)carbamate [Intermediate 11] was used instead of t-butyl-(trans-4-ethynylcyclohexyl)carbamate in Step 1 of Synthesis Example 7.

[Synthesis Example 30] 9-chloro-6-((4,6-dimethyl-2-oxo-1,2-dihydropyridin-3-yl)methyl)-2-(trans-3-(dimethylamino)cyclobutyl)-2,4-dimethyl-7,8-dihydro-[1,3]dioxolo[4,5-g]isoquinolin-5(6H)-one [Compound 35]

The title compound (3.5 mg) was obtained by performing the same reactions as in Synthesis Example 7, except that t-butyl-(trans-3-ethynylcyclobutyl)carbamate was used instead of t-butyl-(trans-4-ethynylcyclohexyl)carbamate in Step 1 of Synthesis Example 7.

[Synthesis Example 31] 9-chloro-6-((4,6-dimethyl-2-oxo-1,2-dihydropyridin-3-yl)methyl)-2-(cis-3-(dimethylamino)cyclohexyl)-2,4-dimethyl-7,8-dihydro-[1,3]dioxolo[4,5-g]isoquinolin-5(6H)-one [Compound 36]

The title compound (19 mg) was obtained by performing the same reactions as in Synthesis Example 7, except that t-butyl-(cis-3-ethynylcyclohexyl)carbamate was used instead of t-butyl-(trans-4-ethynylcyclohexyl)carbamate in Step 1 of Synthesis Example 7.

[Synthesis Example 32] 9-chloro-6-((4,6-dimethyl-2-oxo-1,2-dihydropyridin-3-yl)methyl)-2-(cis-3-(dimethylamino)cyclopentyl)-2,4-dimethyl-7,8-dihydro-[1,3]dioxolo[4,5-g]isoquinolin-5(6H)-one [Compound 37]

The title compound (8 mg) was obtained by performing the same reactions as in Synthesis Example 7, except that t-butyl-(cis-3-ethynylcyclopentyl)carbamate was used instead of t-butyl-(trans-4-ethynylcyclohexyl)carbamate in Step 1 of Synthesis Example 7.

TABLE 2

| # | Structure | Name | Mass |
|---|---|---|---|
| 8 | 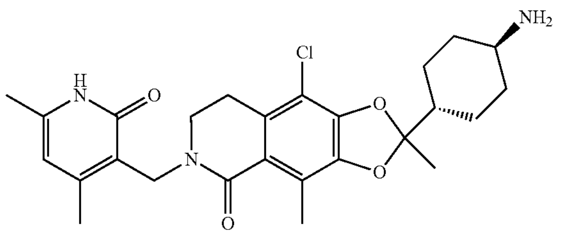 [SMILES: Cc1cc(C)c(CN2CCc3c(Cl)c4c(c(C)c3C2=O)OC(C)([C@H]2CC[C@H](N)CC2)O4)c(=O)[nH]1] | 2-(trans-4-aminocyclohexyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one | 486.2 |
| | $^1$H-NMR spectrum (300 MHz, CDCl3 + MeOD) δ 5.96(s, 1H), 4.74(s, 2H), 3.42-3.37(m, 2H), 2.82-2.80(m, 2H), 2.46(s, 3H), 2.25(s, 6H), 2.05-2.01(m, 4H), 1.90-1.81(m, 2H), 1.62(s, 3H), 1.29-1.25(m, 4H). | | |
| 9 | 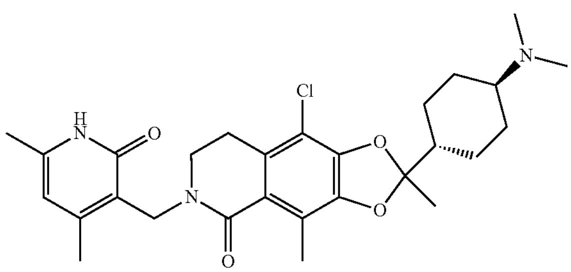 | 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 514.2 |
| | $^1$H-NMR spectrum (300 MHz, CDCl$_3$) δ 11.40(bs, 1H), 5.91(s, 1H), 4.77(s, 2H), 3.48(t, 2H), 2.79(t, 2H), 2.50(s, 3H), 2.29-2.28(m, 12H), 2.25-2.20(m, 1H), 1.98-1.96(m, 4H), 1.90-1.85(m, 1H), 1.61(s, 3H), 1.28-1.25(m, 4H). | | |
| 10 | 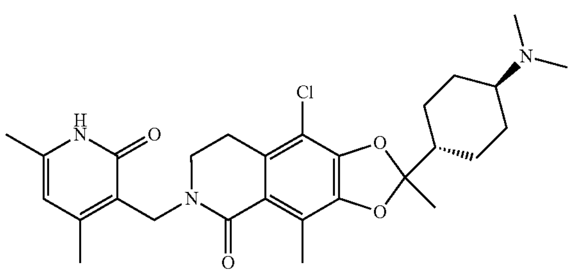 | 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer A | 514.2 |
| | $^1$H-NMR was not measured due to limited quantities. | | |
| 11 | 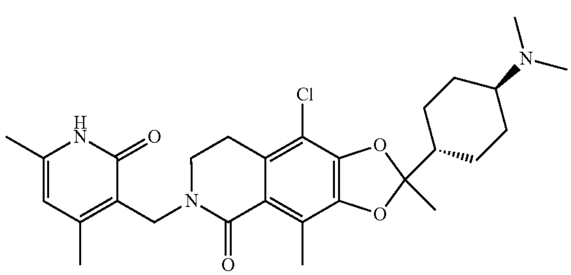 | 9-chloro-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer B | 514.2 |
| | $^1$H-NMR was not measured due to limited quantities. | | |

TABLE 2-continued

| | | | |
|---|---|---|---|
| 12 | 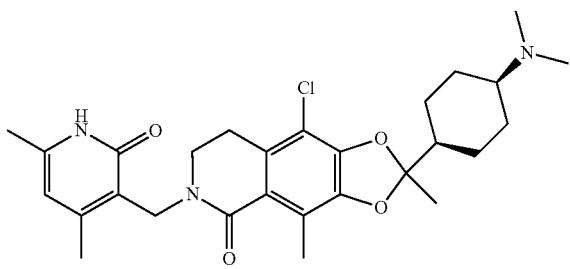 | 9-chloro-6-((4,6-dimethyl-2-oxo-1,2-dihydropyridin-3-yl)methyl)-2-(cis-4-(dimethylamino)cyclohexyl)-2,4-dimethyl-7,8-dihydro-[1,3]dioxolo[4,5-g]isoquinolin-5(6H)-one | 514.2 |

$^{1}$H-NMR spectrum (300 MHz, CDCl$_3$) δ 5.93(s, 1H), 4.78(s, 2H), 3.49(t, 2H), 2.80(t, 2H), 2.50(s, 3H), 2.28(s, 12H), 2.25-2.20(m, 1H), 2.00-1.97(m, 4H), 1.90-1.85(m, 1H), 1.61(s, 3H), 1.28-1.25(m, 4H).

| | | | |
|---|---|---|---|
| 13 | 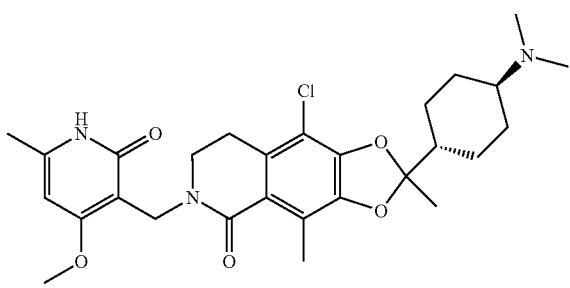 | 9-chloro-2-(trans-4-(dimethylamino)cyclohexyl)-6-((4-methoxy-6-methyl-2-oxo-1,2-dihydropyridin-3-yl)methyl)-2,4-dimethyl-7,8-dihydro-[1,3]dioxolo[4,5-g]isoquinolin-5(6H)-one | 530.2 |

$^{1}$H-NMR spectrum (300 MHz, CDCl$_3$) δ 5.89(s, 1H), 4.73(s, 2H), 3.83(s, 3H), 3.38(t, 2H), 2.80(t, 2H), 2.51(s, 3H), 2.31(s, 3H), 2.28-2.25(m, 6H), 2.27-2.17(m, 1H), 1.99-1.96(m, 4H), 1.83-1.80(m, 1H), 1.61(s, 3H), 1.25-1.23(m, 4H).

| | | | |
|---|---|---|---|
| 14 | 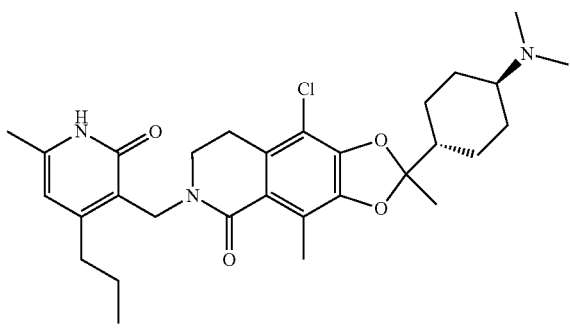 | 9-chloro-2-(trans-4-(dimethylamino)cyclohexyl)-2,4-dimethyl-6-((6-methyl-2-oxo-4-propyl-1,2-dihydropyridin-3-yl)methyl)-7,8-dihydro-[1,3]dioxolo[4,5-g]isoquinolin-5(6H)-one | 542.3 |

$^{1}$H-NMR spectrum (300 MHz, CDCl$_3$) δ 11.10(bs, 1H) 5.93(s, 1H), 4.79(s, 2H), 3.48(t, 2H), 2.80(t, 2H), 2.61(t, 2H), 2.51(s, 3H), 2.27(s, 6H) 2.25-2.10(m, 1H), 2.09-1.89(m, 4H), 1.88-1.71(m, 1H), 1.70-1.45(m, 8H), 1.39-1.10(m, 4H), 0.94(t, 3H).

| | | | |
|---|---|---|---|
| 15 | 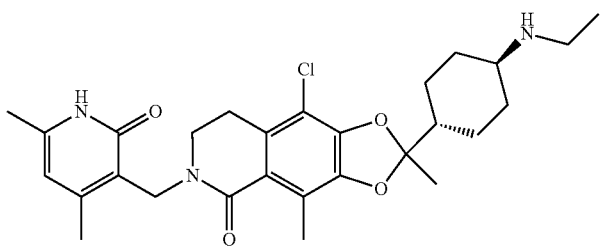 [SMILES: CCN[C@H]1CC[C@H](C2(C)Oc3c(C)c4c(c(Cl)c3O2)CCN(Cc2c(C)cc(C)[nH]c2=O)C4=O)CC1] | 9-chloro-6-((4,6-dimethyl-2-oxo-1,2-dihydropyridin-3-yl)methyl)-2-(trans-4-(ethylamino)cyclohexyl)-2,4-dimethyl-7,8-dihydro-[1,3]dioxolo[4,5-g]isoquinolin-5(6H)-one | 514.2 |

$^{1}$H-NMR spectrum (300 MHz, CDCl$_3$) δ 5.93(s, 1H), 4.77(s, 2H), 3.51-3.47(m, 2H), 2.83-2.73(m, 2H), 2.51(s, 3H), 2.30(s, 3H), 2.29(s, 3H), 2.12-1.88(m, 4H), 1.63(s, 3H), 1.35-1.17(m, 8H), 0.95-0.81(m, 3H).

TABLE 2-continued

| 16 | 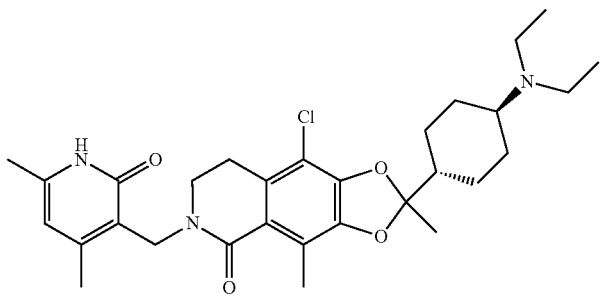 [SMILES: CCN(CC)[C@H]1CC[C@H](C2(C)Oc3c(C)c4c(c(Cl)c3O2)CCN(Cc2c(C)cc(C)[nH]c2=O)C4=O)CC1] | 9-chloro-2-(trans-4-(diethylamino)cyclohexyl)-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one | 542.3 |

$^1$H-NMR spectrum (300 MHz, CDCl$_3$) δ 5.91(s, 1H), 4.75(s, 2H), 3.47(t, 2H), 3.04-3.01(m, 4H), 2.79(t, 2H), 2.48(s, 3H), 2.28(s, 3H), 2.27(s, 3H), 2.26-2.21(m, 2H), 2.10-2.06(m, 3H), 1.89-1.85(m, 4H), 1.67-1.62(m, 1H), 1.60(s, 3H), 1.37(t, 6H).

| 17 | 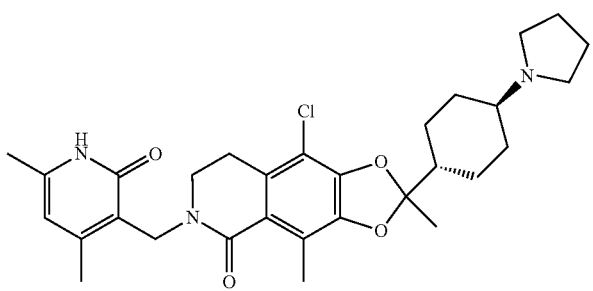 [SMILES: Cc1cc(C)c(CN2CCc3c(Cl)c4c(c(C)c3C2=O)OC(C)([C@H]2CC[C@H](N3CCCC3)CC2)O4)c(=O)[nH]1] | 9-chloro-6-((4,6-dimethyl-2-oxo-1,2-dihydropyridin-3-yl)methyl)-2,4-dimethyl-2-(trans-4-(piperidine)-1-yl)cyclohexyl)-7,8-dihydro-[1,3]dioxolo[4,5-g]isoquinolin-5(6H)-one | 554.3 |

$^1$H-NMR spectrum (300 MHz, CDCl$_3$) δ 12.59(bs, 1H), 5.92(s, 1H), 4.77(s, 2H), 3.50(t, 2H), 2.79(t, 2H), 2.50(s, 3H), 2.49(s, 3H), 2.41(s, 1H), 2.27(s, 6H), 1.98(s, 2H) 1.98(s, 1H), 1.95(s, 1H), 1.79-1.77(m, 1H), 1.60(s, 4H), 1.59(s, 3H), 1.24-1.17(m, 6H), 0.87-0.81(m, 1H).

| 18 | 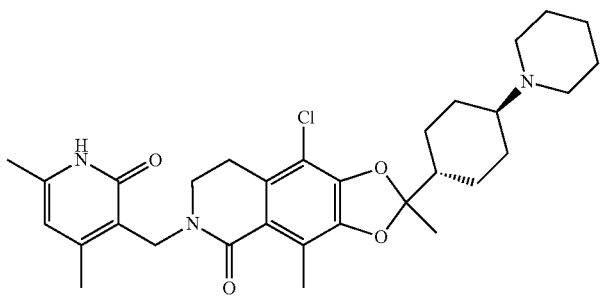 [SMILES: Cc1cc(C)c(CN2CCc3c(Cl)c4c(c(C)c3C2=O)OC(C)([C@H]2CC[C@H](N3CCCCC3)CC2)O4)c(=O)[nH]1] | 9-chloro-6-((4,6-dimethyl-2-oxo-1,2-dihydropyridin-3-yl)methyl)-2,4-dimethyl-2-(trans-4-(pyrrolidine)-1-yl)cyclohexyl)-7,8-dihydro-[1,3]dioxolo[4,5-g]isoquinolin-5(6H)-one | 540.3 |

$^1$H-NMR spectrum (300 MHz, CDCl$_3$) δ 11.89(bs, 1H), 5.91(s, 1H), 4.76(s, 1H), 3.47(t, 2H), 2.79(t, 2H), 2.73(s, 3H), 2.49(s, 3H), 2.28(s, 3H), 2.26(s, 3H), 2.16-2.08(m, 4H), 1.98-1.94(m, 4H), 1.84(s, 4H) 1.61(s, 3H), 1.29-1.25(m, 4H).

| 19 | 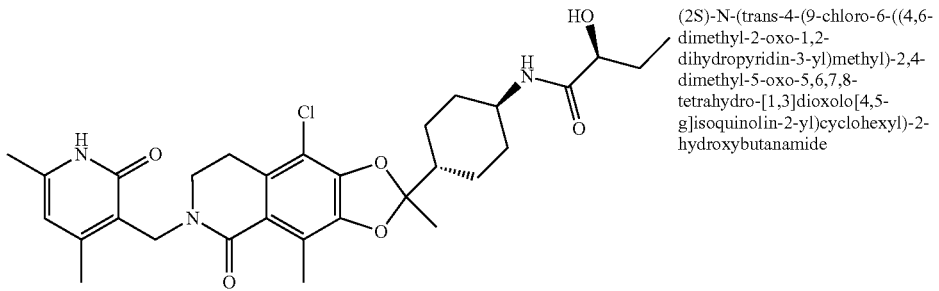 | (2S)-N-(trans-4-(9-chloro-6-((4,6-dimethyl-2-oxo-1,2-dihydropyridin-3-yl)methyl)-2,4-dimethyl-5-oxo-5,6,7,8-tetrahydro-[1,3]dioxolo[4,5-g]isoquinolin-2-yl)cyclohexyl)-2-hydroxybutanamide | 572.2 |

$^1$H-NMR spectrum (300 MHz, CDCl$_3$) δ 11.65(bs, 1H), 6.27(s, 1H), 5.91(s, 1H), 4.75(s, 2H), 4.05(s, 1H), 3.75(q, 1H), 3.65(t, 2H), 2.79(t, 2H), 2.49(s, 3H), 2.28(s, 3H), 2.26(s, 3H), 2.07-1.81(m, 6H), 1.61(s, 3H), 1.39-1.36(m, 4H), 1.24-1.22(m, 1H), 1.18-1.13(m, 1H), 0.96(t, 3H).

TABLE 2-continued

| 20 | [structure] | 2-((trans-4-aminocyclohexyl)methyl)-9-chloro-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one | 500.2 |

$^1$H-NMR spectrum (300 MHz, CDCl$_3$) δ 5.91(s, 1H), 4.76(s, 2H), 3.48(t, 2H), 3.16(s, 2H), 2.80(t, 2H), 2.61(s, 1H), 2.48(s, 3H), 2.28(s, 3H), 2.26(s, 3H), 1.87(s, 4H), 1.85(s, 2H), 1.66(s, 3H), 1.59-1.51(m, 1H), 0.88-0.85(m, 4H).

| 21 | [structure] | 9-chloro-6-((4,6-dimethyl-2-oxo-1,2-dihydropyridin-3-yl)methyl)-2-((trans-4-(dimethylamino)cyclohexyl)methyl)-2,4-dimethyl-7,8-dihydro-[1,3]dioxolo[4,5-g]isoquinolin-5(6H)-one | 528.3 |

$^1$H-NMR spectrum (300 MHz, CDCl$_3$) δ 12.11(bs, 1H), 5.91(s, 1H), 4.76(s, 2H), 3.48(s, 2H), 2.79(t, 2H), 2.49(s, 9H), 2.28(s, 6H), 2.02(s, 2H), 1.98(s, 1H), 1.89(s, 1H), 1.55(s, 1H), 1.37-1.33(m, 2H), 1.29-1.25(m, 2H), 1.10(t, 2H), 0.88-0.80(m, 4H).

| 22 | [structure] | 9-chloro-2-cyclohexyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one | 471.2 |

$^1$H-NMR spectrum (300 MHz, CDCl$_3$) δ 5.90(s, 1H), 4.76(s, 2H), 3.79-3.75(m, 2H), 3.66-3.61(m, 2H), 3.47(t, 2H), 2.79(t, 2H), 2.49(s, 3H), 2.27(s, 3H), 2.26(s, 3H), 1.70-1.60(m, 1H), 1.59(s, 3H), 1.24-1.17(m, 6H).

| 23 | [structure] | 9-chloro-2-cyclopentyl-6-((4,6-dimethyl-2-oxo-1,2-dihydropyridin-3-yl)methyl)-2,4-dimethyl-7,8-dihydro-[1,3]dioxolo[4,5-g]isoquinolin-5(6H)-one | 457.2 |

$^1$H-NMR spectrum (300 MHz, CDCl$_3$) δ 11.42(bs, 1H), 5.90(s, 1H), 4.76(s, 2H), 3.48(t, 2H), 2.79(t, 2H), 2.48(s, 3H), 2.27(s, 3H), 2.25(s, 3H), 1.77-1.75(m, 1H), 1.67(s, 3H), 1.61-1.50(m, 8H).

| 24 | [structure] | 9-chloro-6-((4,6-dimethyl-2-oxo-1,2-dihydropyridin-3-yl)methyl)-2,4-dimethyl-2-(tetrahydro-2H-pyran-4-yl)-7,8-dihydro-[1,3]dioxolo[4,5-g]isoquinolin-5(6H)-one | 473.2 |

$^1$H-NMR spectrum (300 MHz, CDCl$_3$) δ 10.55(bs, 1H), 5.90(s, 1H), 4.76(s, 2H), 4.03(t, 2H), 3.47(t, 2H), 3.37(t, 2H), 2.80(t, 2H), 2.49(s, 3H), 2.28(s, 3H), 2.25(s, 3H), 1.70(t, 1H), 1.63(s, 3H), 0.88-0.83(m, 4H).

TABLE 2-continued

| | | | |
|---|---|---|---|
| 25 | | 9-chloro-6-((4,6-dimethyl-2-oxo-1,2-dihydropyridin-3-yl)methyl)-2-(4-(dimethylamino)phenyl)-2,4-dimethyl-7,8-dihydro-[1,3]dioxolo[4,5-g]isoquinolin-5(6H)-one | 508.2 |

$^1$H-NMR spectrum (300 MHz, CDCl$_3$) δ 7.45(s, 1H), 7.42(s, 1H), 6.69(s, 1H), 6.66(s, 1H), 5.90(s, 1H), 4.76(s, 2H), 3.45(t, 2H), 2.94(s, 6H), 2.77(t, 2H), 2.55(s, 3H), 2.26(s, 4H), 2.25(s, 3H), 2.02(s, 3H).

| | | | |
|---|---|---|---|
| 26 | | 9-chloro-6-((4,6-dimethyl-2-oxo-1,2-dihydropyridin-3-yl)methyl)-2-(4-(dimethylamino)butyl)-2,4-dimethyl-7,8-dihydro-[1,3]dioxolo[4,5-g]isoquinolin-5(6H)-one | 488.2 |

$^1$H-NMR spectrum (300 MHz, CDCl$_3$) δ 5.94(s, 1H), 4.79(s, 2H), 3.50(t, 2H), 2.81(t, 2H), 2.58-2.53(m, 2H), 2.50(s, 3H), 2.44(s, 3H), 2.29(s, 6H), 2.04-1.98(m, 2H), 1.67(s, 3H), 1.60-1.51(m, 2H), 1.32-1.26(m, 5H).

| | | | |
|---|---|---|---|
| 27 | | 9-chloro-6-((4,6-dimethyl-2-oxo-1,2-dihydropyridin-3-yl)methyl)-2-(3,5-(dimethylisoxazol-4-yl)-2,4-dimethyl-7,8-dihydro-[1,3]dioxolo[4,5-g]isoquinolin-5(6H)-one | 484.2 |

$^1$H-NMR spectrum (300 MHz, CDCl$_3$) δ 5.92(s, 1H), 4.76(d, 2H), 3.49(t, 2H), 2.81(t, 2H), 2.54(s, 3H), 2.50(s, 3H), 2.37(s, 3H), 2.27(s, 6H), 2.01(s, 3H).

| | | | |
|---|---|---|---|
| 28 | | 9-chloro-6-((4,6-dimethyl-2-oxo-1,2-dihydropyridin-3-yl)methyl)-2,4-dimethyl-2-(piperidin-4-yl)-7,8-dihydro-[1,3]dioxolo[4,5-g]isoquinolin-5(6H)-one | 472.2 |

$^1$H-NMR spectrum (300 MHz, CDCl$_3$) δ 5.90(s, 1H), 4.76(s, 2H), 3.49(t, 2H), 3.16-3.12(m, 2H), 2.79(t, 2H), 2.59(t, 2H), 2.49(s, 3H), 2.28(s, 3H), 2.26(s, 3H), 2.00-1.92(m, 1H), 1.84-1.80(m, 2H), 1.62(s, 3H), 1.44-1.38(m, 2H).

| | | | |
|---|---|---|---|
| 29 | | 9-chloro-6-((4,6-dimethyl-2-oxo-1,2-dihydropyridin-3-yl)methyl)-2,4-dimethyl-2-(1-methylpiperidin-4-yl)-7,8-dihydro-[1,3]dioxolo[4,5-g]isoquinolin-5(6H)-one | 486.2 |

$^1$H-NMR spectrum (300 MHz, CDCl$_3$) δ 11.53(bs, 1H), 5.90(s, 1H), 4.76(s, 2H), 3.48(t, 2H), 2.79(t, 2H), 2.48(s, 3H), 2.28(s, 3H), 2.26(s, 6H), 1.92-1.88(m, 1H), 1.84-1.79(m, 4H), 1.70-1.52(m, 7H).

TABLE 2-continued

| 30 | | 9-chloro-6-((4,6-dimethyl-2-oxo-1,2-dihydropyridin-3-yl)methyl)-2-(1-((R)-2-hydroxybutanoyl)piperidin-4-yl)-2,4-dimethyl-7,8-dihydro-[1,3]dioxolo[4,5-g]isoquinolin-5(6H)-one | 558.2 |
|---|---|---|---|

¹H-NMR spectrum (300 MHz, CDCl₃) δ 11.64(bs, 1H), 5.91(s, 1H), 4.76(s, 2H), 4.72(s, 1H), 4.30(s, 1H), 3.79-3.77(m, 2H), 3.51(t, 2H), 3.00(t, 1H), 2.80(t, 2H), 2.61(t, 1H), 2.49(s, 3H), 2.28(s, 3H), 2.26(s, 3H), 2.12-2.09(m, 1H), 1.94-1.91(m, 1H), 1.62(s, 3H), 1.46-1.38(m, 4H), 1.20(t, 3H), 0.87-0.82(m, 1H).

| 31 | | 9-chloro-6-((4,6-dimethyl-2-oxo-1,2-dihydropyridin-3-yl)methyl)-2,4-dimethyl-2-(1-(2,2,2)-trifluoroethyl)piperidin-4-yl)-7,8-dihydro-[1,3]dioxolo[4,5-g]isoquinolin-5(6H)-one | 554.2 |

¹H-NMR spectrum (300 MHz, CDCl₃) δ 5.93(s, 1H), 4.78(s, 2H), 3.03-3.00(m, 2H), 2.82(t, 2H), 2.51(s, 3H), 2.30(s, 3H), 2.27(s, 3H), 1.87-1.81(m, 2H), 1.64(s, 3H), 1.30(s, 5H), 0.95-0.82(m, 4H).

| 32 | | 9-chloro-6-((4,6-dimethyl-2-oxo-1,2-dihydropyridin-3-yl)methyl)-2,4-dimethyl-2-(1-methyl-1H-indol-5-yl)-7,8-dihydro-[1,3]dioxolo[4,5-g]isoquinolin-5(6H)-one | 518.2 |

¹H-NMR spectrum (300 MHz, CDCl₃) δ 7.85(d, 1H), 7.44(dd, 1H), 7.31(d, 1H), 7.06(d, 1H), 6.49(d, 1H), 5.87(s, 1H), 4.75(s, 2H), 3.77(s, 3H), 3.47-3.40(m, 2H), 2.79-2.74(m, 2H), 2.57(s, 3H), 2.24(d, 6H), 2.10(s, 3H)

| 33 | | 9-chloro-6-((4,6-dimethyl-2-oxo-1,2-dihydropyridin-3-yl)methyl)-2-(trans-4-methoxycyclohexyl)-2,4-dimethyl-7,8-dihydro-[1,3]dioxolo[4,5-g]isoquinolin-5(6H)-one | 501.2 |

¹H-NMR spectrum (300 MHz, CDCl₃) δ 13.0(bs, 1H), 5.94(s, 1H), 4.78(s, 2H), 3.50(t, 2H), 3.47(s, 3H), 3.14-3.09(m, 1H), 2.80(t, 2H), 2.51(s, 3H), 2.29(s, 6H), 2.15-2.12(m, 2H), 1.99-195(m, 2H), 1.85(t, 1H), 1.62(s, 3H), 1.33-1.13(m, 4H).

| 34 | | 9-chloro-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one | 500.2 |

TABLE 2-continued

¹H-NMR spectrum (300 MHz, CDCl₃) δ 5.91(s, 1H), 4.77(s, 2H), 3.49(t, 2H), 2.80(t, 2H), 2.50(s, 3H), 2.42(s, 3H), 2.35-2.30(m, 1H), 2.29(s, 3H), 2.27(s, 3H), 2.04-1.93(m, 5H), 1.86-1.81(m, 1H), 1.62(s, 3H), 1.34-1.26(m, 2H), 1.11-0.99(m, 2H).

35 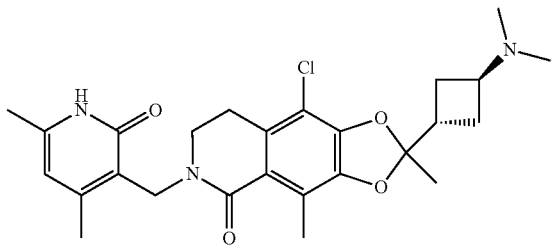

9-chloro-6-((4,6-dimethyl-2-oxo-1,2-dihydropyridin-3-yl)methyl)-2-(trans-3-(dimethylamino)cyclobutyl)-2,4-dimethyl-7,8-dihydro-[1,3]dioxolo[4,5-g]isoquinolin-5(6H)-one — 486.2

¹H-NMR spectrum (300 MHz, CDCl₃) δ 11.5(bs, 1H), 5.91(s, 1H), 4.77(s, 2H), 3.51(t, 2H), 2.81(t, 2H), 2.76-2.68(m, 2H), 2.53(s, 3H), 2.30(s, 3H), 2.27(s, 3H), 2.11(s, 10H), 1.62(s, 3H).

36 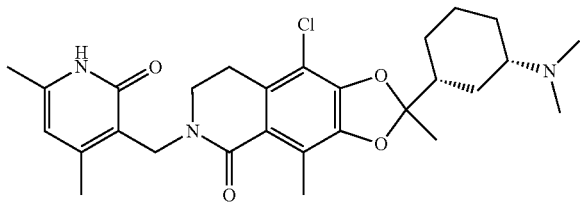

9-chloro-6-((4,6-dimethyl-2-oxo-1,2-dihydropyridin-3-yl)methyl)-2-(cis-3-(dimethylamino)cyclohexyl)-2,4-dimethyl-7,8-dihydro-[1,3]dioxolo[4,5-g]isoquinolin-5(6H)-one — 514.2

¹H-NMR spectrum (300 MHz, CDCl₃) δ 12.8(bs, 1H), 5.94(s, 1H), 4.78(s, 2H), 3.49(t, 2H), 2.80(t, 2H), 2.50(s, 3H), 2.29(s, 13H), 2.10-2.06(m, 1H), 1.96-1.87(m, 4H), 1.62(s, 3H), 1.29-1.10(m, 4H).

37 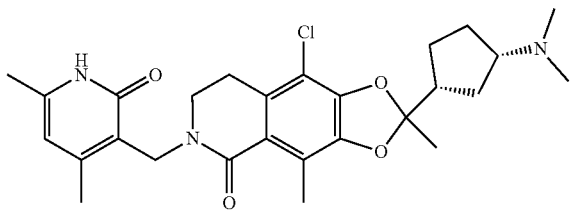

9-chloro-6-((4,6-dimethyl-2-oxo-1,2-dihydropyridin-3-yl)methyl)-2-(cis-3-(dimethylamino)cyclopentyl)-2,4-dimethyl-7,8-dihydro-[1,3]dioxolo[4,5-g]isoquinolin-5(6H)-one — 500.2

¹H-NMR spectrum (300 MHz, CDCl₃) δ 12.23(bs, 1H), 5.91(s, 1H), 4.76(s, 2H), 3.47(t, 2H), 2.78(t, 2H), 2.50-2.35(m, 1H), 2.47(s, 3H), 2.27(d, 6H), 2.22(d, 6H), 2.01-1.99(m, 2H), 1.87-1.83(m, 1H), 1.75-1.71(m, 2H), 1.59-1.43(m, 2H), 1.24(s, 3H)

[Synthesis Example 33] 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one [Compound 38] and 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one [Compound 39]

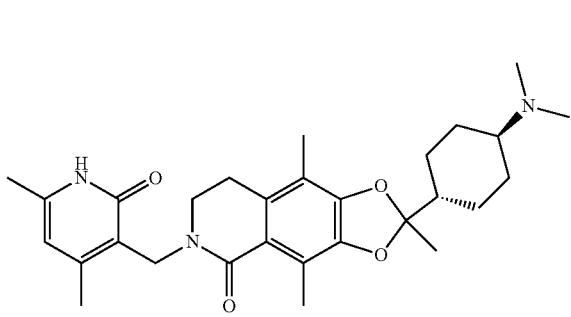

Step 1. Production of t-butyl-((trans-4-(2,4,9-trimethyl-5-oxo-5,6,7,8-tetrahydro-[1,3]dioxolo[4,5-g]isoquinolin-2-yl)cyclohexyl)carbamate

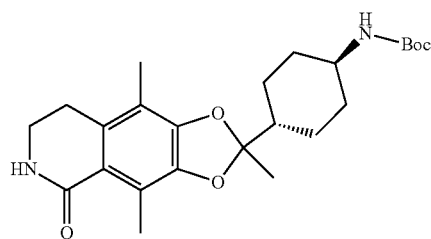 [SMILES: Cc1c2c(c(C)c3c1OC(C)([C@H]1CC[C@H](NC(=O)OC(C)(C)C)CC1)O3)C(=O)NCC2]

The title compound (800 g) was obtained by performing the same reaction as in Step 1 of Synthesis Example 2, except that 6,7-dihydroxy-5,8-dimethyl-3,4-dihydroisoquinolin-1(2H)-one [Intermediate 3] was used instead of 6,7-dihydroxy-3,4-dihydroisoquinolin-1(2H)-one in Step 1 of Synthesis Example 2.

Step 2. Production of t-butyl-((trans-4-(6-((2-(benzyloxy)-4,6-dimethylpyridin-3-yl)methyl)-2,4,9-trimethyl-5-oxo-5,6,7,8-tetrahydro-[1,3]dioxolo[4,5-g]isoquinolin-2-yl)cyclohexyl)carbamate

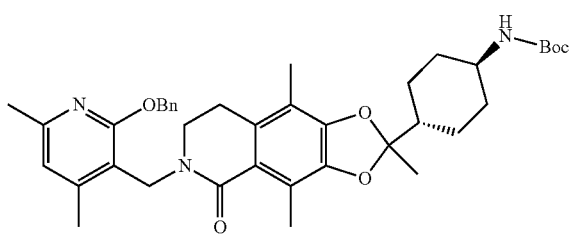 [SMILES: Cc1cc(C)c(CN2CCc3c(C)c4c(c(C)c3C2=O)OC(C)([C@H]2CC[C@H](NC(=O)OC(C)(C)C)CC2)O4)c(OCc2ccccc2)n1]

The title compound (258 g) was obtained by performing the same reaction as in Step 2 of Synthesis Example 2 using t-butyl-((trans-4-(2,4,9-trimethyl-5-oxo-5,6,7,8-tetrahydro-[1,3]dioxolo[4,5-g]isoquinolin-2-yl)cyclohexyl)carbamate (200 mg, 0.46 mmol) synthesized in Step 1 above.

Step 3. Production of 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one [Compound 38]

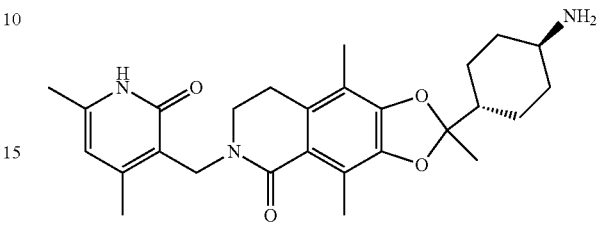

t-butyl-((trans-4-(6-((2-(benzyloxy)-4,6-dimethylpyridin-3-yl)methyl)-2,4,9-trimethyl-5-oxo-5,6,7,8-tetrahydro-[1,3]dioxolo[4,5-g]isoquinolin-2-yl)cyclohexyl)carbamate (258 mg, 0.41 mmol) synthesized in Step 2 above and 4M hydrochloric acid-1,4-dioxane solution (1.5 ml) were sequentially added to methanol, and then the reaction solution was stirred at room temperature for 12 hours. After completion of the reaction, the reaction solution was neutralized by adding saturated aqueous sodium bicarbonate solution and extracted using 20% methanol-chloroform. The extracted organic layer was dried using anhydrous sodium sulfate and concentrated under reduced pressure. The resulting residue was stirred in a mixture solution of 20% ethyl ester-diethyl ether for 1 hour, and the resulting solid was filtered and washed to obtain the title compound (137 mg).

Step 4. Production of 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one [Compound 39]

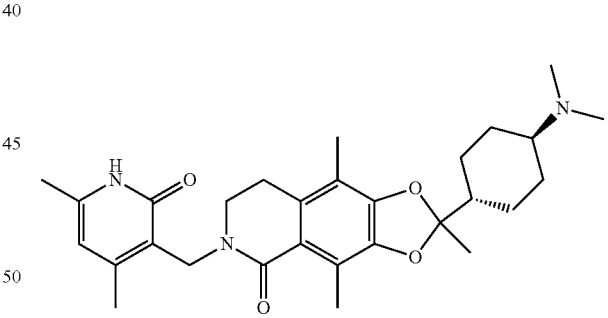

The title compound (80 mg) was obtained by performing the same reaction as in Step 5 of Synthesis Example 2 using 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one (130 mg, 0.27 mmol) synthesized in Step 3 above.

[Synthesis Example 34] 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one isomers A and B [Compound 40 and Compound 41]

6-((4,6-dimethyl-2-oxo-1,2-dihydropyridin-3-yl)methyl)-2-(trans-4-(dimethylamino)cyclohexyl)-2,4,9-trimethyl-7,8- dihydro-[1,3]dioxolo[4,5-g]isoquinolin-5(6H)-one synthesized in Synthesis Example 33 was separated into enantiomers under the following conditions. The absolute stereochemistry of each isomer was not determined.

Column: Daicel Chiralcel OZ-H, 4.6×250 mm, 5 μM
Temperature: 35° C.
Flow rate: 0.8 ml/min
Wavelength: 270 nm
Elution solvent: n-hexane:ethanol:diethylamine=500:500:0.4 (v/v %)
First peak: 15.8 min—isomer A (99.9% ee)
Second peak: 23.1 min—isomer B (99.9% ee)

[Synthesis Example 35] 2-(trans-4-(dimethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one [Compound 42]

The title compound (30 mg) was obtained by performing the same reactions as in Synthesis Example 33, except that 2-(benzyloxy)-3-(chloromethyl)-4-methoxy-6-methylpyridine was used instead of 2-(benzyloxy)-3-(chloromethyl)-4,6-dimethylpyridine in Step 2 of Synthesis Example 33.

[Synthesis Example 36] 2-(trans-4-(dimethylamino)cyclohexyl)-2,4,9-trimethyl-6-((6-methyl-2-oxo-4-propyl-1,2)-dihydropyridin-3-yl)methyl)-7,8-dihydro-[1,3]dioxolo[4,5-g]isoquinolin-5(6H)-one [Compound 43]

The title compound (35 mg) was obtained by performing the same reactions as in Synthesis Example 33, except that 2-(benzyloxy)-3-(chloromethyl)-6-methyl-4-propylpyridine was used instead of 2-(benzyloxy)-3-(chloromethyl)-4,6-dimethylpyridine in Step 2 of Synthesis Example 33.

[Synthesis Example 37] 2-cyclohexyl-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one [Compound 44]

The title compound (123 mg) was obtained by performing the same reactions as Step 1 to Step 4 of Synthesis Example 32, except that ethynylcyclohexane was used instead of t-butyl-(trans-4-ethynylcyclohexyl)carbamate in Step 1 of Synthesis Example 33.

[Synthesis Example 38] 2-(trans-4-(ethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one [Compound 45] and 2-(trans-4-(diethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one [Compound 46]

The same reaction as in Step 4 of Synthesis Example 35 was performed except that 2-(trans-4-aminocyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one (78 mg, 0.10 mmol) and acetaldehyde (9.3 mg, 0.21 mmol) were used instead of 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one and 37% formaldehyde aqueous solution, respectively, in Step 4 of Synthesis Example 33. The resulting residues were purified by basic silica gel column chromatography to obtain the title compounds (45 mg of Compound 45 and 11 mg of Compound 46).

[Synthesis Example 39] 2-(trans-4-(ethyl(methyl)amino)cyclohexyl)-6-((4-methoxy-6-methyl-2-oxo-1,2-dihydropyridin)-3-yl)methyl)-2,4,9-trimethyl-7,8-dihydro-[1,3]dioxolo[4,5-g]isoquinolin-5(6H)-one [Compound 47]

The title compound (21 mg) was obtained by performing the same reaction as in Step 4 of Synthesis Example 33, except that 2-(trans-4-(ethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one [Compound 45] synthesized in Synthesis Example 38 was used instead of 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one in Step 4 of Synthesis Example 33.

TABLE 3

| 38 | | 2-(trans-4-aminocyclohexyl)-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one | 466.3 |
|---|---|---|---|

$^1$H-NMR spectrum (300 MHz, CDCl$_3$) δ 5.95 (s, 1H), 4.75 (s, 2H), 3.38 (t, 2H), 2.64-2.60 (m, 3H), 2.46 (s, 3H), 2.25 (s, 6H), 2.04 (s, 3H), 1.96-1.92 (m, 4H), 1.82-1.75 (m, 1H), 1.55 (s, 3H), 1.30-1.11 (m, 4H).

TABLE 3-continued

| 39 | 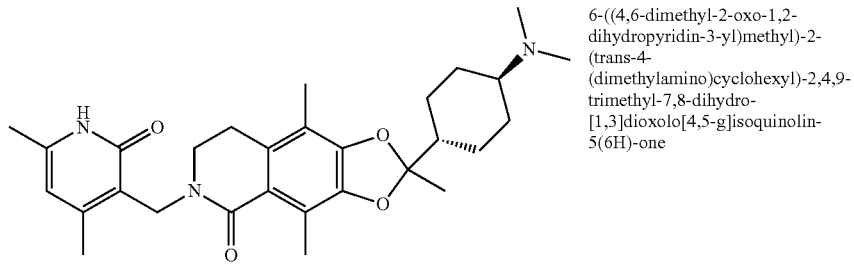 | 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one | 494.3 |

$^1$H-NMR spectrum (300 MHz, CDCl$_3$) δ 5.94 (s, 1H), 4.80 (s, 2H), 3.42 (t, 2H), 2.62 (t, 2H), 2.50 (s, 3H), 2.29 (s, 3H), 2.27 (s, 9H), 2.24-2.20 (m, 1H), 2.04 (s, 3H), 1.99-1.96 (m, 4H), 1.80-1.75 (m, 1H), 1.56 (s, 3H), 1.24-1.20 (m, 4H).

| 40 | 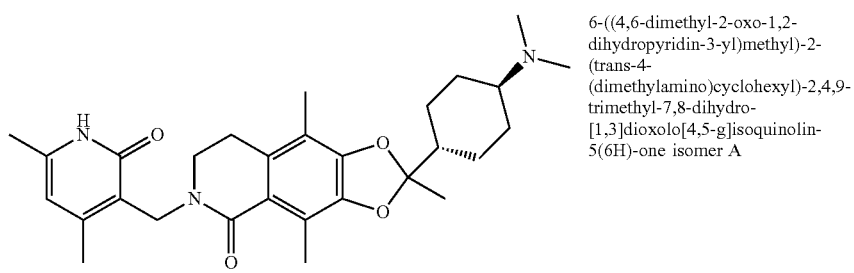 | 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one isomer A | 494.3. |

$^1$H-NMR was not measured due to limited quantities.

| 41 | 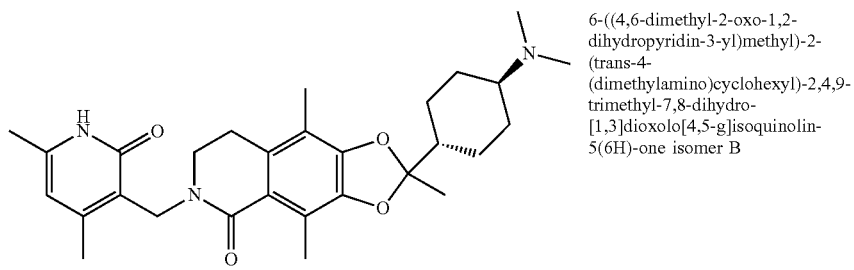 | 6-((4,6-dimethyl-2-oxo-1,2-dihydropyridin-3-yl)methyl)-2-(trans-4-(dimethylamino)cyclohexyl)-2,4,9-trimethyl-7,8-dihydro-[1,3]dioxolo[4,5-g]isoquinolin-5(6H)-one isomer B | 494.3 |

$^1$H-NMR was not measured due to limited quantities.

| 42 | 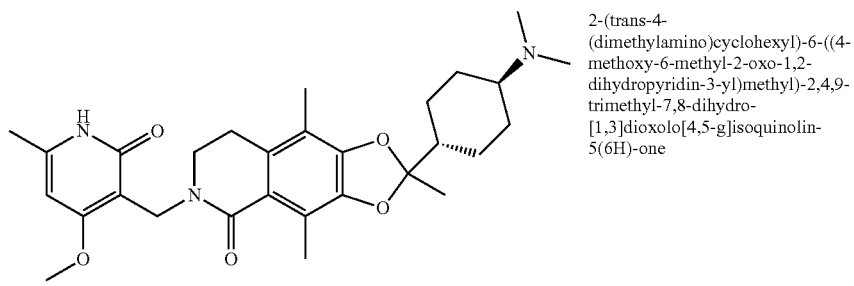 | 2-(trans-4-(dimethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one | 510.3 |

$^1$H-NMR spectrum (300 MHz, CDCl$_3$) δ 5.89 (s, 1H), 4.75 (s, 2H), 3.82 (s, 3H), 3.33 (t, 2H), 2.62 (t, 2H), 2.51 (s, 3H), 2.33 (s, 3H), 2.26 (s, 6H), 2.22-2.16 (m, 1H), 2.04 (s, 3H), 1.98-1.96 (m, 4H), 1.78-1.74 (m, 1H), 1.55 (s, 3H), 1.25-1.20 (m, 4H).

TABLE 3-continued

| 43 | 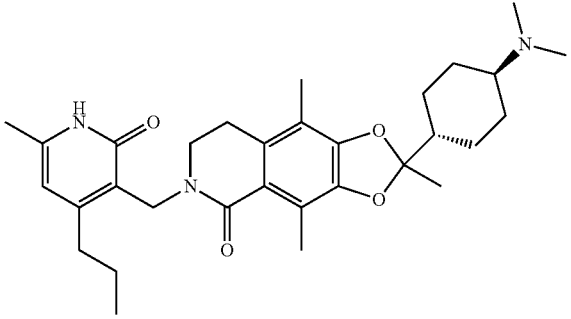 | 2-(trans-4-(dimethylamino)cyclohexyl)-2,4,9-trimethyl-6-((6-methyl-2-oxo-4-propyl-1,2-dihydropyridin-3-yl))methyl)-7,8-dihydro-[1,3]dioxolo[4,5-g]isoquinolin-5(6H)-one | 522.3 |

$^1$H-NMR spectrum (300 MHz, CDCl$_3$) δ 5.95 (s, 1H), 4.82 (s, 2H), 3.43 (t, 2H), 2.62-2.59 (m, 4H), 2.51 (s, 3H), 2.30 (s, 3H), 2.27 (s, 6H), 2.20-2.16 (m, 1H), 2.04 (s, 3H), 1.98-1.96 (m, 4H), 1.80-1.77 (m, 1H), 1.56-1.50 (m, 5H), 1.25-1.21 (m, 4H), 0.94 (t, 3H).

| 44 | 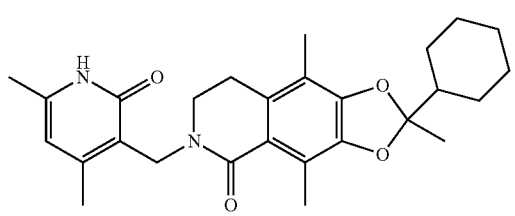 [SMILES: Cc1cc(C)c(CN2CCc3c(C)c4c(c(C)c3C2=O)OC(C)(C2CCCCC2)O4)c(=O)[nH]1] | 2-cyclohexyl-6-((4,6-dimethyl-2-oxo-1,2-dihydropyridin-3-yl)methyl)-2,4,9-trimethyl-7,8-dihydro-[1,3]dioxolo[4,5-g]isoquinolin-5(6H)-one | 451.3 |

$^1$H-NMR spectrum (300 MHz, CDCl$_3$) δ 5.90 (s, 1H), 4.79 (s, 2H), 3.43 (t, 2H), 2.61 (t, 2H), 2.50 (s, 3H), 2.27 (s, 3H), 2.26 (s, 3H), 2.04 (s, 3H), 1.90-1.87 (m, 2H), 1.79-1.76 (m, 3H), 1.68-1.66 (m, 1H), 1.61 (s, 3H), 1.25-1.20 (m, 5H).

| 45 | 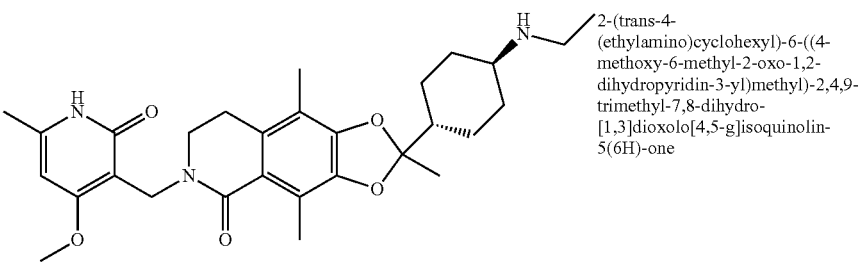 | 2-(trans-4-(ethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one | 510.3 |

$^1$H-NMR spectrum (300 MHz, CDCl$_3$) δ 5.91 (s, 1H), 4.90 (d, 1H), 4.46 (d, 1H), 3.85 (s, 3H), 3.48 (t, 2H), 2.90 (q, 2H), 2.65-2.63 (m, 1H), 2.61 (t, 2H), 2.48 (s, 3H), 2.41 (s, 3H), 2.10-2.05 (m, 1H), 2.04 (s, 3H), 1.98-1.96 (m, 4H), 1.50 (s, 3H), 1.35 (t, 3H), 1.25-1.18 (m, 4H).

| 46 | 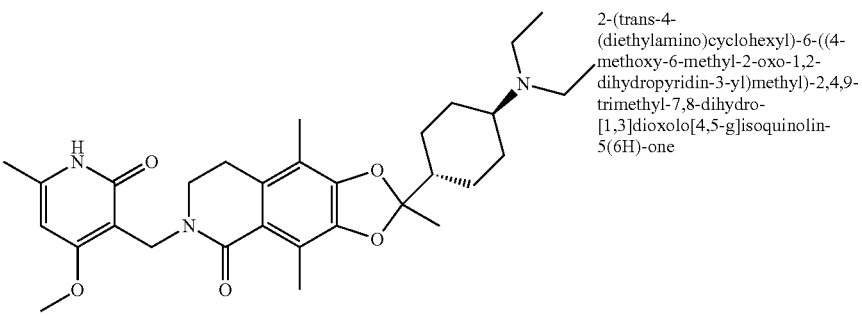 | 2-(trans-4-(diethylamino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one | 538.3 |

$^1$H-NMR spectrum (300 MHz, CDCl$_3$) δ 11.73 (bs, 1H), 5.90 (s, 1H), 4.74 (d, 2H), 3.83 (s, 3H), 3.47 (q, 4H), 3.34 (t, 2H), 3.30-3.15 (m, 5H), 2.62 (t, 2H), 2.50 (s, 3H), 2.33 (s, 3H), 2.04 (s, 3H), 1.98-1.96 (m, 1H), 1.55 (s, 3H), 1.45 (t, 6H), 1.25-1.22 (m, 4H).

TABLE 3-continued

| 47 | | 2-(trans-4-(ethyl(methyl)amino)cyclohexyl)-6-((4-methoxy-6-methyl-2-oxo-1,2-dihydropyridin-3-yl)methyl)-2,4,9-trimethyl-7,8-dihydro-[1,3]dioxolo[4,5-g]isoquinolin-5(6H)-one | 524.3 |
|---|---|---|---|

¹H-NMR spectrum (300 MHz, CDCl₃) δ 5.89 (s, 1H), 4.74 (s, 2H), 3.82 (s, 3H), 3.35 (t, 2H), 2.64-2.58 (m, 4H), 2.51 (s, 3H), 2.50-2.47 (m, 1H), 2.31 (s, 3H), 2.27 (s, 3H), 2.04 (s, 3H), 2.00-1.92 (m, 4H), 1.78-1.74 (m, 1H), 1.55 (s, 3H), 1.28-1.20 (m, 4H), 1.08 (t, 3H).

[Synthesis Example 40] 9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 48]

t-butyl-((trans-4-(2,4-dimethyl-5-oxo-5,6,7,8-tetrahydro-[1,3]dioxolo[4,5-g]isoquinolin-2-yl)cyclohexyl)carbamate (616 mg, 1.48 mmol) synthesized in Step 1 of Synthesis Example 7 was added to acetonitrile (7.5 ml), followed by the addition of N-bromosuccinimide (316 mg, 1.77 mmol). The reaction solution was stirred at room temperature for 13 hours, neutralized by adding saturated aqueous sodium bicarbonate solution and extracted using ethyl acetate. The extracted organic layer was dried using anhydrous sodium sulfate and distilled under reduced pressure. The resulting residue was purified by silica gel column chromatography to obtain t-butyl-((trans-4-(9-bromo-2,4-dimethyl-5-oxo-5,6,7,8-tetrahydro-[1,3]dioxolo[4,5-g]isoquinolin-2-yl)cyclohexyl)carbamate (550 mg).

The title compound (120 mg) was obtained by performing the same reactions as in Step 3 to Step 5 of Synthesis Example 7 using the above-synthesized t-butyl-((trans-4-(9-bromo-2,4-dimethyl-5-oxo-5,6,7,8-tetrahydro-[1,3]dioxolo)[4,5-g]isoquinolin-2-yl)cyclohexyl)carbamate.

[Synthesis Example 41] 9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomers [Compound 49 and Compound 50]

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one synthesized in Synthesis Example 40 was separated into enantiomers under the following conditions. The absolute stereochemistry of each isomer was not determined.

Column: Daicel Chiralcel OZ-H, 4.6×250 mm, 5 μM
Temperature: 35° C.
Flow rate: 0.8 ml/min
Wavelength: 270 nm
Elution solvent: n-hexane:ethanol:diethylamine=500:500:0.4 (v/v %)
First peak: 14.0 min—isomer A (99.9% ee)
Second peak: 20.6 min—isomer B (99.9% ee)

[Synthesis Example 42] 9-bromo-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one [Compound 51]

The title compound (70 mg) was obtained by performing the same reactions as in Step 1 to Step 5 of Synthesis Example 40, except that t-butyl(trans-4-ethynylcyclohexyl)(methyl)carbamate [Intermediate 11] was used instead of t-butyl-(trans-4-ethynylcyclohexyl)carbamate in Synthesis Example 40.

[Synthesis Example 43] 6-((4,6-dimethyl-2-oxo-1,2-dihydropyridin-3-yl)methyl)-2-(trans-4-(dimethylamino)cyclohexyl)-2,4-dimethyl-9-vinyl-7,8-dihydro-[1,3]dioxolo[4,5-g]isoquinolin-5(6H)-one [Compound 52]

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one (43 mg, 0.08 mmol, Compound 48) synthesized in Synthesis Example 40, 4,4,5,5-tetramethyl-2-vinyl-1,3,2-dioxaborolane (12 mg, 0.08 mmol), potassium phosphate (41 mg, 0.19 mmol) and a [1,1'-bis(diphenylphosphino)ferrocene]palladium(II) dichloride dichloromethane complex (1:1) (8 mg, 0.01 mmol) were sequentially added to a mixture solution of 1,4-dioxane:water (8 ml, 4:1), argon gas replacement was performed, and then the mixture was refluxed at 90° C. for 13 hours. The reaction solution was cooled to room temperature, dichloromethane and water were added thereto, and the organic layer was extracted. The extracted organic layer was dried using anhydrous sodium sulfate and distilled under reduced pressure. The resulting residue was purified by basic silica gel column chromatography to obtain the title compound (37 mg).

[Synthesis Example 44] 6-((4,6-dimethyl-2-oxo-1,2-dihydropyridin-3-yl)methyl)-2-(trans-4-(dimethylamino)cyclohexyl)-9-ethynyl-2,4-dimethyl-7,8-dihydro-[1,3]dioxolo[4,5-g]isoquinolin-5(6H)-one [Compound 53]

Step 1. Production of 6-((4,6-dimethyl-2-oxo-1,2-dihydropyridin-3-yl)methyl)-2-(trans-4-(dimethylamino)cyclohexyl)-2,4-dimethyl-5-oxo-5,6,7,8-tetrahydro-[1,3]dioxolo[4,5-g]isoquinolin-9-carbaldehyde 6-((4,6-dimethyl-2-oxo-1,2-dihydropyridin-3-yl)methyl)-2-(trans-4-(dimethylamino)cyclohexyl)-2,4-dimethyl-9-vinyl-7,8-dihydro-[1,3]dioxolo[4,5-g]isoquinolin-5(6H)-one (33 mg, 0.07 mmol, Compound 52) synthesized in Synthesis Example 43 was added to a mixture of tetrahydrofuran (0.6 ml) and water (0.3 ml), and 4% osmium tetroxide (21 µl, 0.003 mmol) and sodium periodate (28 mg, 0.13 mmol) were sequentially added thereto. The reaction solution was stirred at room temperature for 13 hours, and then insoluble matter was removed by filtration, and saturated sodium nitrite was added to the filtrate, followed by extraction with dichloromethane. The extracted organic layer was dried using anhydrous sodium sulfate and distilled under reduced pressure to obtain the title compound (26.7 mg).

Step 2. 6-((4,6-dimethyl-2-oxo-1,2-dihydropyridin-3-yl)methyl)-2-(trans-4-(dimethylamino)cyclohexyl)-9-ethynyl-2,4-dimethyl-7,8-dihydro-[1,3]dioxolo[4,5-g]isoquinolin-5(6H)-one [Compound 53]

6-((4,6-dimethyl-2-oxo-1,2-dihydropyridin-3-yl)methyl)-2-(trans-4-(dimethylamino)cyclohexyl)-2,4-dimethyl-5-oxo-5,6,7,8-tetrahydro-[1,3]dioxolo[4,5-g]isoquinolin-9-carbaldehyde (26.8 mg, 0.05 mmol) synthesized in Step 1 above was added to methanol (0.6 ml), and potassium carbonate (8.8 mg, 0.06 mmol) and dimethyl(1-diazo-2-oxopropyl)phosphonate (12.3 mg, 0.06 mmol) were sequentially added thereto. The reaction solution was stirred at room temperature for 13 hours, and saturated brine and dichloromethane were added thereto to extract the organic layer. The extracted organic layer was dried using anhydrous sodium sulfate and distilled under reduced pressure. The resulting residue was purified by basic silica gel column chromatography to obtain the title compound (10 mg).

[Synthesis Example 45] 9-cyclopropyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 54]

The title compound (12 mg) was obtained by performing the same reactions as in Synthesis Example 43, except that cyclopropylboronic acid was used instead of 4,4,5,5-tetramethyl-2-vinyl-1,3,2-dioxaborolane in Synthesis Example 43.

[Synthesis Example 46] 6-((4,6-dimethyl-2-oxo-1,2-dihydropyridin-3-yl)methyl)-2-(trans-4-(dimethylamino)cyclohexyl)-2,4-dimethyl-9-(4-(morpholinomethyl)phenyl)-7,8-dihydro-[1,3]dioxolo[4,5-g]isoquinolin-5(6H)-one [Compound 55]

The title compound (14 mg) was obtained by performing the same reactions as in Synthesis Example 43, except that 4-(4-(4,4,5,5-tetramethyl-1,3,2-dioxaborolan-2-yl)benzyl)morpholine was used instead of 4,4,5,5-tetramethyl-2-vinyl-1,3,2-dioxaborolane in Synthesis Example 43.

[Synthesis Example 47] 6-((4,6-dimethyl-2-oxo-1,2-dihydropyridin-3-yl)methyl)-2-(trans-4-(dimethylamino)cyclohexyl)-2,4-dimethyl-9-phenyl-7,8-dihydro-[1,3]dioxolo[4,5-g]isoquinolin-5(6H)-one [Compound 56]

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one (70 mg, 0.13 mmol, Compound 48) synthesized in Synthesis Example 40, phenylboronic acid (46 mg, 0.38 mmol), potassium triphosphate (80 mg, 0.38 mmol) and Pd(dppf)Cl$_2$·CH$_2$Cl$_2$ (1:1) (21 mg, 0.03 mmol) were dissolved in 1,4-dioxane/water (4:1, 3.5 mL), and then argon gas replacement was performed. The reaction solution was stirred at 80° C. for 18 hours, cooled to room temperature and then filtered through celite. The resulting product was extracted with dichloromethane, dried using anhydrous sodium sulfate, and then distilled under reduced pressure. The resulting residue was purified by silica gel column chromatography to obtain the title compound (50 mg).

[Synthesis Example 48] 9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 57]

The title compound (100 mg) was obtained by performing the same reactions as in Synthesis Example 47, except that 1-cyclopentenylboronic acid was used instead of phenylboronic acid in Synthesis Example 47.

[Synthesis Example 49] 9-cyclopentyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 58]

9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one (75 mg, 0.14 mmol) synthesized in Synthesis Example 48 and 10% palladium/carbon (75 mg) were dissolved in ethyl acetate/methanol (1:1, 5 mL), and then a hydrogen balloon was attached. The reaction solution was stirred at room temperature for 18 hours, filtered through celite, and distilled under reduced pressure. The resulting residue was purified by silica gel column chromatography to obtain the title compound (50 mg).

[Synthesis Example 50] 9-(cyclohex-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 59]

The title compound (80 mg) was obtained by performing the same reactions as in Synthesis Example 47, except that 1-cyclohexenylboronic acid was used instead of phenylboronic acid in Synthesis Example 47.

[Synthesis Example 51] 9-cyclohexyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 60]

The title compound (25 mg) was obtained by performing the same reactions as in Synthesis Example 49, except that 9-(cyclohex-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one [Compound 59] was used instead of 9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one in Synthesis Example 49.

[Synthesis Example 52] 6-((4,6-dimethyl-2-oxo-1,2-dihydropyridin-3-yl)methyl)-2-(trans-4-(dimethylamino)cyclohexyl)-2,4-dimethyl-9-(prop-1-en-2-yl)-7,8-dihydro-[1,3]dioxolo[4,5-g]isoquinolin-5(6H)-one [Compound 61]

The title compound (80 mg) was obtained by performing the same reactions as in Synthesis Example 47, except that 2-isopropenylboronic acid pinacol ester was used instead of phenylboronic acid in Synthesis Example 47.

[Synthesis Example 53] 6-((4,6-dimethyl-2-oxo-1,2-dihydropyridin-3-yl)methyl)-2-(trans-4-(dimethylamino)cyclohexyl)-9-isopropyl-2,4-dimethyl-7,8-dihydro-[1,3]dioxolo[4,5-g]isoquinolin-5(6H)-one [Compound 62]

The title compound (27 mg) was obtained by performing the same reactions as in Synthesis Example 49, except that 6-((4,6-dimethyl-2-oxo-1,2-dihydropyridin-3-yl)methyl)-2-(trans-4-(dimethylamino)cyclohexyl)-2,4-dimethyl-9-(prop-1-en-2-yl)-7,8-dihydro-[1,3]dioxolo[4,5-g]isoquinolin-5(6H)-one [Compound 61] was used instead of 9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one in Synthesis Example 49.

[Synthesis Example 54] 6-((4,6-dimethyl-2-oxo-1,2-dihydropyridin-3-yl)methyl)-2-(trans-4-(dimethylamino)cyclohexyl)-9-ethyl-2,4-dimethyl-7,8-dihydro-[1,3]dioxolo[4,5-g]isoquinolin-5(6H)-one [Compound 63]

The title compound (22 mg) was obtained by performing the same reactions as in Synthesis Example 49, except that 6-((4,6-dimethyl-2-oxo-1,2-dihydropyridin-3-yl)methyl)-2-(trans-4-(dimethylamino)cyclohexyl)-2,4-dimethyl-9-vinyl-7,8-dihydro-[1,3]dioxolo[4,5-g]isoquinolin-5(6H)-one [Compound 52] was used instead of 9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one in Synthesis Example 49.

[Synthesis Example 55] 6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one [Compound 64]

The title compound (27 mg) was obtained by performing the same reactions as in Synthesis Example 47, except that furan-2-boronic acid was used instead of phenylboronic acid in Synthesis Example 47.

[Synthesis Example 56] 9-(3,6-dihydro-2H-pyran-4-yl)-6-((4,6-dimethyl-2-oxo-1,2-dihydropyridin-3)-yl) methyl)-2-(trans-4-(dimethylamino)cyclohexyl)-2,4-dimethyl-7,8-dihydro-[1,3]dioxolo[4,5-g] isoquinolin-5(6H)-one [Compound 65]

The title compound (37 mg) was obtained by performing the same reactions as in Synthesis Example 47, except that 3,6-dihydro-2H-pyran-4-borolane was used instead of phenylboronic acid in Synthesis Example 47.

[Synthesis Example 57] 6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one [Compound 66]

The title compound (38 mg) was obtained by performing the same reactions as in Synthesis Example 47, except that pyridin-3-ylboronic acid was used instead of phenylboronic acid in Synthesis Example 47.

[Synthesis Example 58] 6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one [Compound 67]

The title compound (13 mg) was obtained by performing the same reactions as in Synthesis Example 47, except that 5-(4,4,5,5-tetramethyl-1,3,2-dioxaborolan-2-yl)thiazole was used instead of phenylboronic acid in Synthesis Example 47.

[Synthesis Example 59] 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5 (6H)-one [Compound 68]

The title compound (36 mg) was obtained by performing the same reactions as in Synthesis Example 47, except that 1-methylpyrazole-4-borolane was used instead of phenylboronic acid in Synthesis Example 47.

[Synthesis Example 60] 6-((4,6-dimethyl-2-oxo-1,2-dihydropyridin-3-yl)methyl)-2-(trans-4-(dimethylamino)cyclohexyl)-2,4-dimethyl-5-oxo-5,6,7,8-tetrahydro-[1,3]dioxolo[4,5-g]isoquinolin-9-carbonitrile [Compound 69]

9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one (50 mg, 0.09 mmol, Compound 48) synthesized in Synthesis Example 40, tris(dibenzylideneacetone)dipalladium(0) (33 mg, 0.036 mmol), 1,1'-bis(diphenylphosphino)

ferrocene (40 mg, 0.072 mmol), zinc cyanide (32 mg, 0.27 mmol) and zinc (5 mg, 0.072 mmol) were sequentially added to dimethylacetamide (2 ml), and argon gas replacement was performed. The mixture was refluxed at 80° C. for 16 hours. The reaction solution was cooled to room temperature, dichloromethane and water were added thereto, and the organic layer was extracted. The extracted organic layer was dried using anhydrous sodium sulfate and distilled under reduced pressure. The resulting residue was purified by basic silica gel column chromatography to obtain the title compound (26 mg).

TABLE 4

| 48 | 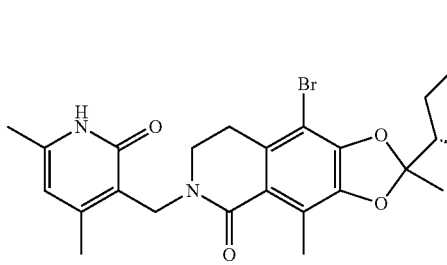 | 9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 558.2 |
|---|---|---|---|

$^1$H-NMR spectrum (300 MHz, CDCl$_3$) δ 11.72 (bs, 1H), 5.91 (s, 1H), 4.77 (s, 2H), 3.48 (t, 2H), 2.80 (t, 2H), 2.48 (s, 3H), 2.28 (s, 3H), 2.26 (s, 9H), 2.15-2.12 (m, 1H), 1.98-1.96 (m, 4H), 1.83-1.77 (m, 1H), 1.61 (s, 3H), 1.28-1.22 (m, 4H).

| 49 | 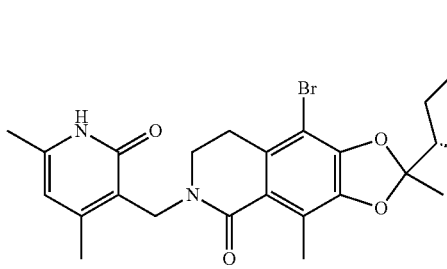 | 9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer A | 558.2 |
|---|---|---|---|

$^1$H-NMR spectrum (300 MHz, CDCl3) δ 12.33 (brs, 1H), 5.92 (s, 1H), 4.77 (d, 2H), 3.48 (t, 2H), 2.80 (t, 2H), 2.49 (s, 3H), 2.28 (s, 6H), 2.26 (s, 6H), 2.15 (t, 1H), 1.98-1.96 (m, 4H), 1.79 (t, 1H), 1.62 (s, 3H), 1.28-1.22 (m, 4H).

| 50 | 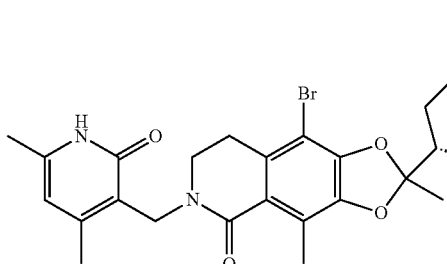 | 9-bromo-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one isomer B | 558.2 |
|---|---|---|---|

$^1$H-NMR spectrum (300 MHz, CDCl3) δ 12.42 (brs, 1H), 5.92 (s, 1H), 4.77 (d, 2H), 3.48 (t, 2H), 2.80 (t, 2H), 2.49 (s, 3H), 2.28 (s, 6H), 2.26 (s, 6H), 2.15 (t, 1H), 1.98-1.96 (m, 4H), 1.81 (t, 1H), 1.62 (s, 3H), 1.32-1.14 (m, 4H).

| 51 | 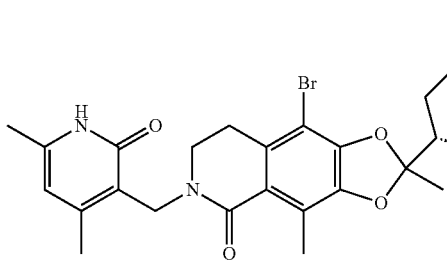 | 9-bromo-6-((4,6-dimethyl-2-oxo-1,2-dihydropyridin-3-yl)methyl)-2,4-dimethyl-2-(trans-4-(methylamino)cyclohexyl)-7,8-dihydro-[1,3]dioxolo[4,5-g]isoquinolin-5(6H)-one | 558.2 |
|---|---|---|---|

$^1$H-NMR spectrum (300 MHz, CDCl$_3$) δ 5.92 (s, 1H), 4.77 (s, 2H), 3.48 (t, 2H), 2.80 (t, 2H), 2.49 (s, 3H), 2.43 (s, 3H), 2.38-2.32 (m, 1H), 2.28 (s, 6H), 2.04-1.90 (m, 5H), 1.86-1.81 (m, 1H), 1.62 (s, 3H), 1.34-1.21 (m, 2H), 1.13-1.01 (m, 2H).

| | | | |
|---|---|---|---|
| 52 | 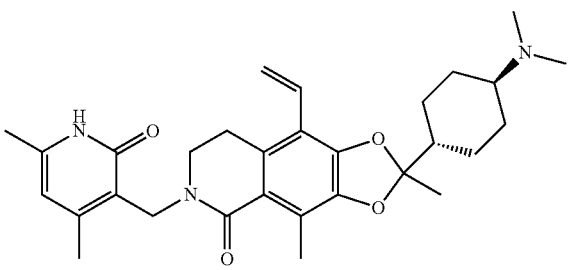 | 6-((4,6-dimethyl-2-oxo-1,2-dihydropyridin-3-yl)methyl)-2-(trans-4-(dimethylamino)cyclohexyl)-2,4-dimethyl-9-vinyl-7,8-dihydro-[1,3]dioxolo[4,5-g]isoquinolin-5(6H)-one | 506.3 |

¹H-NMR spectrum (300 MHz, CDCl₃) δ 12.90 (bs, 1H), 6.58 (dd, 1H), 5.92 (s, 1H), 5.85 (d, 1H), 5.45 (d, 1H), 4.79 (s, 2H), 3.43 (t, 2H), 2.76 (t, 2H), 2.50 (s, 3H), 2.28 (s, 12H), 2.26-2.22 (m, 1H), 1.99-1.97 (m, 4H), 1.81-1.79 (m, 1H), 1.61 (s, 3H), 1.26-1.22 (m, 4H).

| | | | |
|---|---|---|---|
| 53 | 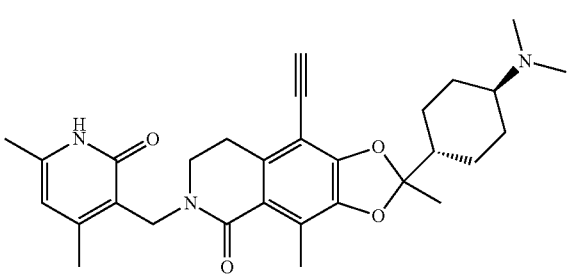 | 6-((4,6-dimethyl-2-oxo-1,2-dihydropyridin-3-yl)methyl)-2-(trans-4-(dimethylamino)cyclohexyl)-9-ethynyl-2,4-dimethyl-7,8-dihydro-[1,3]dioxolo[4,5-g]isoquinolin-5(6H)-one | 504.3 |

¹H-NMR spectrum (300 MHz, CDCl₃) δ 12.20 (bs, 1H), 5.91 (s, 1H), 4.78 (s, 2H), 3.47 (t, 2H), 3.37 (s, 1H), 2.87 (t, 2H), 2.52 (s, 3H), 2.31 (s, 6H), 2.27 (s, 6H), 2.17-2.15 (m, 1H), 2.04-1.98 (m, 4H), 1.83-1.80 (m, 1H), 1.61 (s, 3H), 1.28-1.26 (m, 4H).

| | | | |
|---|---|---|---|
| 54 | 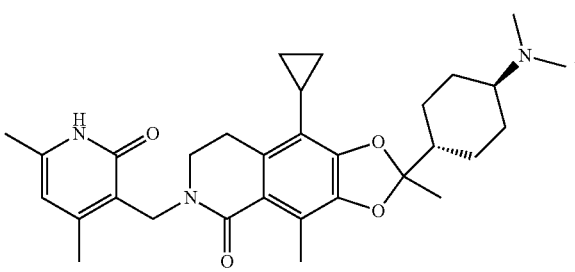 | 9-cyclopropyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 520.3 |

¹H-NMR spectrum (300 MHz, CDCl₃) δ 12.50 (bs, 1H), 5.92 (s, 1H), 4.80 (s, 2H), 3.44 (t, 2H), 2.85 (t, 2H), 2.49 (s, 3H), 2.29-2.28 (m, 12H), 2.15-2.12 (m, 1H), 1.98-1.96 (m, 4H), 1.80-1.76 (m, 1H), 1.56-1.52 (m, 4H), 1.25-1.20 (m, 4H), 0.86 (dd, 2H), 0.65 (dd, 2H).

| | | | |
|---|---|---|---|
| 55 | 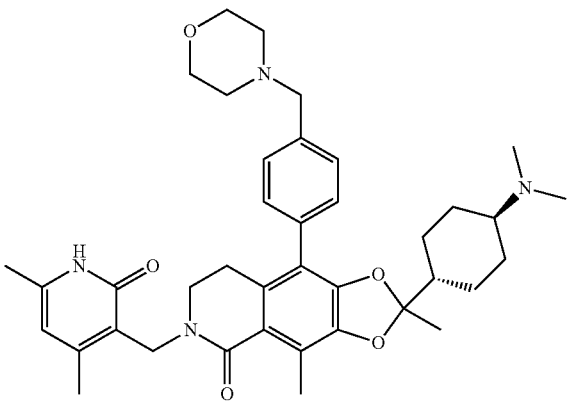 | 6-((4,6-dimethyl-2-oxo-1,2-dihydropyridin-3-yl)methyl)-2-(trans-4-(dimethylamino)cyclohexyl)-2,4-dimethyl-9-(4-(morpholinomethyl)phenyl)-7,8-dihydro-[1,3]dioxolo[4,5-g]isoquinolin-5(6H)-one | 655.4 |

¹H-NMR spectrum (300 MHz, CDCl₃) δ 10.80 (bs, 1H), 7.34 (d, 2H), 7.19 (d, 2H), 5.87 (s, 1H), 4.76 (s, 2H), 3.72 (t, 4H), 3.51 (s, 2H), 3.33 (t, 2H), 2.55 (s, 3H), 2.50-2.46 (m, 6H), 2.30-2.29 (m, 9H), 2.20 (s, 3H), 1.97-1.94 (m, 4H), 1.83-1.77 (m, 2H), 1.54 (s, 3H), 1.25-1.22 (m, 4H).

| | | | |
|---|---|---|---|
| 56 | 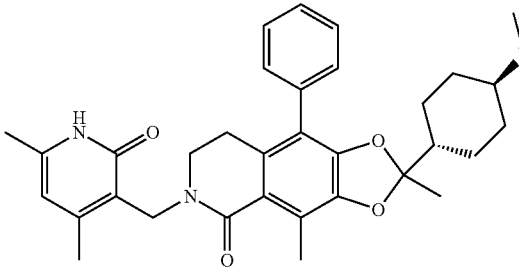 | 6-((4,6-dimethyl-2-oxo-1,2-dihydropyridin-3-yl)methyl)-2-(trans-4-(dimethylamino)cyclohexyl)-2,4-dimethyl-9-phenyl-7,8-dihydro-[1,3]dioxolo[4,5-g]isoquinolin-5(6H)-one | 556.3 |

¹H-NMR spectrum (300 MHz, CDCl₃) δ 7.42-7.33 (m, 4H), 7.26-7.24 (m, 1H), 5.89 (s, 1H), 4.78 (s, 2H), 3.35 (t, 2H), 2.61-2.57 (m, 5H), 2.31 (s, 3H), 2.30 (s, 6H), 2.21-2.19 (m, 4H), 1.97-1.95 (m, 4H), 1.75 (m, 1H), 1.55 (s, 3H), 1.26-1.22 (m, 4H)

| | | | |
|---|---|---|---|
| 57 | 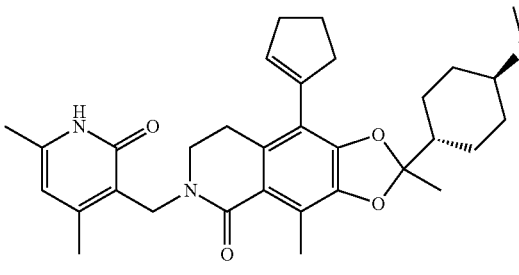 | 9-(cyclopent-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 546.3 |

¹H-NMR spectrum (300 MHz, CDCl₃) δ 11.87 (brs, 1H), 5.91 (s, 1H), 5.62 (d, 1H), 4.79 (d, 2H), 3.38 (m, 2H), 2.69 (t, 2H), 2.63-2.47 (m, 7H), 2.44 (s, 3H), 2.30 (s, 9H), 2.15 (m, 1H), 2.01-1.96 (m, 6H), 1.77 (m, 1H), 1.56 (s, 3H), 1.26-1.23 (m, 4H)

| | | | |
|---|---|---|---|
| 58 | 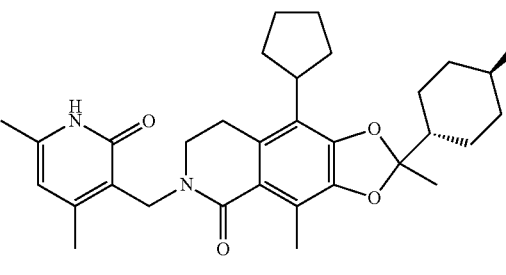 | 9-cyclopentyl-6-((4,6-dimethyl-2-oxo-1,2-dihydropyridin-3-yl)methyl)-2-(trans-4-dimethylamino)cyclohexyl)-2,4-dimethyl-7,8-dihydro-[1,3]dioxolo[4,5-g]isoquinolin-5(6H)-one | 548.3 |

¹H-NMR spectrum (300 MHz, CDCl₃) δ 10.98 (brs, 1H), 5.90 (s, 1H), 4.80 (s, 2H), 3.44 (t, 2H), 3.01 (m, 1H), 2.75 (t, 2H), 2.50 (s, 3H), 2.29-2.27 (m, 12H), 2.17 (m, 1H), 1.98 (m, 4H), 1.82 (m, 5H), 1.61 (m, 4H), 1.57 (s, 3H), 1.24 (m, 4H).

| | | | |
|---|---|---|---|
| 59 | 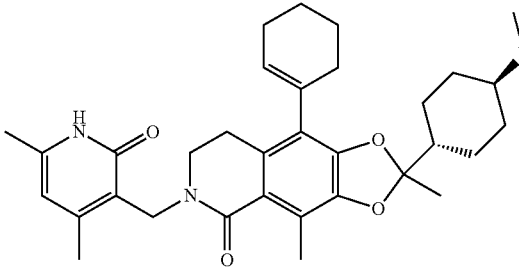 | 9-(cyclohex-1-en-1-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 560.3 |

¹H-NMR spectrum (300 MHz, CDCl₃) δ 11.89 (brs, 1H), 5.90 (s, 1H), 5.52 (s, 1H), 4.79 (s, 2H), 3.39 (t, 2H), 2.67-2.63 (m, 2H), 2.52 (s, 3H), 2.31-2.27 (m, 12H), 2.13 (m, 5H), 1.97 (m, 4H), 1.73-1.65 (m, 5H), 1.56 (s, 3H), 1.26-1.21 (m, 4H).

TABLE 4-continued

| 60 | 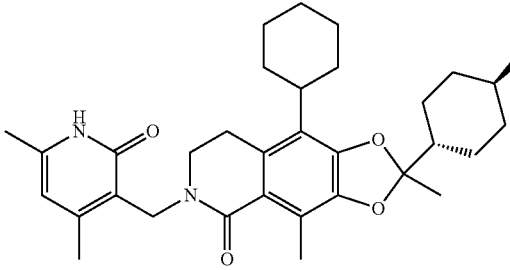 | 9-cyclohexyl-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 562.4 |

¹H-NMR spectrum (300 MHz, CDCl₃) δ 5.90 (s, 1H), 4.79 (s, 2H), 4.74 (s, 1H), 3.45 (t, 2H), 2.71 (t, 2H), 2.49 (s, 3H), 2.30-2.26 (m, 12H), 2.20 (m, 1H), 2.05-1.98 (m, 4H), 1.81 (m, 7H), 1.56 (s, 3H), 1.27 (m, 4H), 0.89-0.84 (m, 4H).

| 61 | 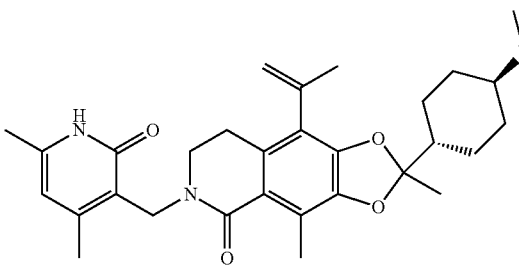 | 6-((4,6-dimethyl-2-oxo-1,2-dihydropyridin-3-yl)methyl)-2-(trans-4-(dimethylamino)cyclohexyl)-2,4-dimethyl-9-(prop-1-en-2-yl)-7,8-dihydro-[1,3]dioxolo[4,5-g]isoquinolin-5(6H)-one | 520.3 |

¹H-NMR spectrum (300 MHz, CDCl₃) δ 12.27 (brs, 1H), 5.91 (s, 1H), 5.30 (q, 1H), 4.83 (s, 1H), 4.80 (s, 2H), 3.41 (t, 2H), 2.68 (m, 2H), 2.52 (s, 3H), 2.29-2.27 (m, 12H), 2.16-2.12 (m, 1H), 1.97 (m, 7H), 1.77 (m, 1H), 1.58 (s, 3H), 1.24-1.9 (m, 4H).

| 62 | 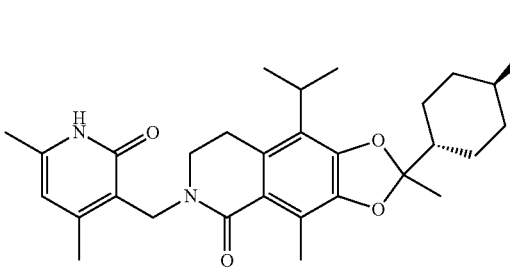 | 6-((4,6-dimethyl-2-oxo-1,2-dihydropyridin-3-yl)methyl)-2-(trans-4-(dimethylamino)cyclohexyl)-9-isopropyl-2,4-dimethyl-7,8-dihydro-[1,3]dioxolo[4,5-g]isoquinolin-5(6H)-one | 522.3 |

¹H-NMR spectrum (300 MHz, CDCl₃) δ 11.46 (brs, 1H), 5.91 (s, 1H), 4.80 (s, 2H), 3.44 (t, 2H), 2.99 (m, 1H), 2.70 (t, 2H), 2.50 (s, 3H), 2.31-2.27 (m, 12H), 2.24 (m, 1H), 2.00 (m, 4H), 1.79 (m, 1H), 1.56 (s, 3H), 1.27-1.23 (m, 10H).

| 63 | 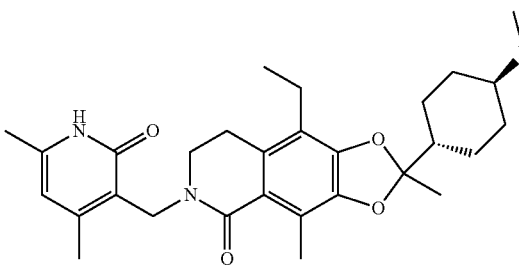 | 6-((4,6-dimethyl-2-oxo-1,2-dihydropyridin-3-yl)methyl)-2-(trans-4-(dimethylamino)cyclohexyl)-9-ethyl-2,4-dimethyl-7,8-dihydro-[1,3]dioxolo[4,5-g]isoquinolin-5(6H)-one | 508.3 |

¹H-NMR spectrum (300 MHz, CDCl₃) δ 12.73 (brs, 1H), 5.92 (s, 1H), 4.81 (s, 2H), 3.44 (t, 2H), 2.67 (t, 2H), 2.52-2.50 (m, 5H), 2.28 (s, 12H), 2.17 (m, 1H), 1.97 (m, 4H), 1.77 (m, 1H), 1.56 (s, 3H), 1.26-1.22 (m, 4H), 1.06 (t, 3H).

TABLE 4-continued

| | Structure | Name | MS |
|---|---|---|---|
| 64 | 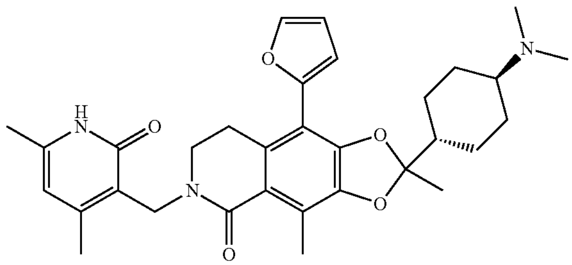 | 6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5(6H)-one | 545.3 |

$^1$H-NMR spectrum (300 MHz, CDCl$_3$) δ 11.92 (bs, 1H), 7.45 (dd, 1H), 6.60 (dd, 1H), 6.48 (dd, 1H), 5.91 (s, 1H), 4.80 (s, 2H), 3.41 (t, 2H), 2.95-2.90 (m, 2H), 2.54 (s, 3H), 2.30 (s, 3H), 2.27 (s, 9H), 2.17 (t, 1H), 2.00-1.97 (m, 4H), 1.80 (t, 1H), 1.60 (s, 3H), 1.33-1.15 (m, 4H).

| | Structure | Name | MS |
|---|---|---|---|
| 65 | | 9-(3,6-dihydro-2H-pyran-4-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5(6H)-one | 562.3 |

$^1$H-NMR spectrum (300 MHz, CDCl$_3$) δ 11.5 (bs, 1H), 5.90 (s, 1H), 5.57 (s 1H), 4.78 (s, 2H), 4.27-4.26 (m, 2H), 3.89 (t, 2H), 3.41 (t, 2H), 2.68 (t, 2H), 2.51 (s, 3H), 2.34 (s, 3H), 2.29 (s, 3H), 2.27 (s, 3H), 2.26 (s, 3H), 2.14 (t, 1H), 1.97-1.94 (m, 4H), 1.76-1.72 (m, 3H), 1.55 (s, 3H), 1.26-1.09 (m, 4H).

| | Structure | Name | MS |
|---|---|---|---|
| 66 | | 6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5(6H)-one | 557.3 |

$^1$H-NMR spectrum (300 MHz, CDCl$_3$) δ 8.57-8.52 (m, 2H), 7.58-7.55 (dt, H), 7.35-7.31 (dd, 1H), 5.88 (s, 1H), 4.76 (s, 2H), 3.37 (t, 2H), 2.57 (t, 2H), 2.56 (s, 3H), 2.29 (d, 9H), 2.21 (s, 3H), 2.00-1.90 (m, 5H), 1.85-1.70 (m, 1H), 1.25 (s, 3H), 1.15-1.08 (m, 2H), 0.92-0.79 (m, 2H)

| | Structure | Name | MS |
|---|---|---|---|
| 67 | | 6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5(6H)-one | 563.3 |

$^1$H-NMR spectrum (300 MHz, CDCl$_3$) δ 8.85 (s, 1H), 7.80 (s, 1H), 5.90 (s, 1H), 4.76 (s, 2H), 3.45-3.38 (m, 2H), 2.82-2.68 (m, 2H), 2.54 (s. 3H), 2.30 (d, 9H), 2.22 (s, 3H), 2.03-1.96 (m, 5H), 1.87-1.72 (m, 1H), 1.25 (s, 3H), 0.94-0.79 (m, 4H)

TABLE 4-continued

| | | | |
|---|---|---|---|
| 68 | [structure] | 6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5(6H)-one | 560.3 |
| | $^1$H-NMR spectrum (300 MHz, CDCl$_3$) δ 11.5 (bs, 1H), 7.57 (s, 1H), 7.47(s 1H), 5.91 (s, 1H), 4.79 (s, 2H), 3.94 (s, 3H), 3.41 (t, 2H), 2.79 (t, 2H), 2.54 (s, 3H), 2.31 (s, 3H), 2.28 (s, 6H), 2.25 (s, 3H), 2.17 (t, 1H), 1.99-1.97 (m, 4H), 1.80 (t, 1H), 1.58 (s, 3H), 1.25-1.19 (m, 4H). | | |
| 69 | [structure] | 6-((4,6-dimethyl-2-oxo-1,2-dihydropyridin-3-yl)methyl)-2-(trans-4-(dimethylamino)cyclohexyl)-2,4-dimethyl-5-oxo-5,6,7,8-tetrahydro-[1,3]dioxolo[4,5-g]isoquinolin-9-carbonitrile | 505.3 |
| | $^1$H-NMR spectrum (300 MHz, CDCl$_3$) δ 12.1 (bs, 1H), 5.93 (s, 1H), 4.75 (s 2H), 3.57 (t, 2H), 2.90 (t, 2H), 2.55 (s, 3H), 2.30 (s, 3H), 2.28 (s, 9H), 2.17 (t, 1H), 1.99-1.97 (m, 4H), 1.82 (t, 1H), 1.63 (s, 3H), 1.28-1.18 (m, 4H). | | |

Experimental Example 1: Evaluation of Inhibitory Activity Against EZH1/EZH2 methyltransferase The inhibitory activities of the synthetic compounds against EZH1 or EZH2 methyltransferase were measured. The experiment was conducted by Reaction Biology Corp., and the activity of EZH1 or EZH2 was measured using a radiometric scintillation proximity assay. To measure the IC$_{50}$ of each of the synthetic compounds for EZH1 or EZH2, 2.3 nmol/L EZH1 or EZH2, 1 □mol/L histone H3 (21-44)-lys (biotin), 1.5 □mol/L S-adenyl medthionine (SAM), and 500 nmol/L $^3$H-SAM were added to each compound or DMSO in a reaction buffer and allowed to react at room temperature for 90 minutes. The reaction buffer consisted of 50 mmol/L Tris-HCl (pH 8.0), 50 mmol/L NaCl, 1 mmol/L EDTA, 1 mmoL/L DTT, 1 mmol/L PMSF, and 1% DMSO. Trichloroacetic acid was added to terminate the reaction, and PVT streptavidin-coated SPA beads were added to each reaction solution, followed by further reaction at room temperature for 1 hour again. The methylation value of the substrate peptide was measured using the TopCount NXT plate reader. Based on average value of DMSO-treated wells set to 100% and the background average value set to 0%, the measured values were converted to percent activity, and then the IC$_{50}$ value was determined using the "log (inhibitor) vs. "normalized response—variable slope" analysis method of the GraphPad PRISM v6 program.

Experimental Example 2: Cell Growth Inhibition Test

In order to confirm the inhibitory effects of the synthetic compounds against the growth of blood cancer cell lines, evaluation was performed against KARPAS 422, RPMI 8226, KMS-11, JeKo-1, MV-4-11, Mino, Pfeiffer, SU-DHL-4, and RS4; 11 cell lines. A test for the Pfeiffer and SU-DHL-4 cell lines was performed by KYinno Co., Ltd., a test for the RS4; 11 cell line was performed by Shanghai Chempartner Co., Ltd., and a test for the Kasumi-1, MV-4-11, MM.1S, KMS-11, JeKo-1, Mino (ATCC), RPMI 8226 (KCLB), and KARPAS 422 (ECACC) cell lines was performed after purchase.

DMSO at a final concentration of 0.1% or less or a DMSO solution of each of the synthetic compounds was added to media to have the concentration and treatment time described in Table 5 below, and cells were cultured at 37° C. under 5% CO$_2$. Each type of the cultured cells was seeded in 6-well plates or 48-96 well plates, and subculture or medium replacement was performed every 3 to 4 days. Next, the cells were subcultured for a total of 7 to 14 days, and then seeded in 96-well plates. 3 to 5 days before the measurement of the effect, the cells were seeded in 96-well plates, and then the absorbance (Tz) on the day of seeding was measured. The absorbance after the reaction was measured by the plate reader device Synergy NeoAlpha (Biotek) using Cell-Titer-Glo Cell Viability Assay (Promega, G7573) according to the attached manual. Based on the absorbance (Tz) measured on the seeding day and the absorbance of each of the DMSO-treated group (C) and the sample-added group (Ti) measured on the day of effect determination, the percentage of cell proliferation inhibition was calculated according to the following Equation 1.

$[(Ti-Tz)/(C-Tz)] \times 100$ for concentrations for which $Ti \geq Tz$ $[(Ti-Tz)/C] \times 100$ for concentrations for which $Ti < Tz$.   [Equation 1]

TABLE 5

| Cell line | Source | Culture medium | Culture time | Treatment concentration |
|---|---|---|---|---|
| KARPAS 422 | ECACC | 20% RPMI 1640 | 7 days | 0.001~1000 nM (1/10 dilution) |
| RPMI 8226 | KCLB | 10% RPMI 1640 | 7 days | 0.06~1,000 nM (1/5 dilution) |
| KMS-11 | ATCC | 10% RPMI 1640 | 10 days | 0.1~10,000 nM (1/10 dilution) |
| JeKo-1 | ATCC | 20% RPMI 1640 | 10 days | 0.1~10,000 nM (1/10 dilution) |
| MV4;11 | ATCC | 10% IMDM | 10 days | 0.32~1,000 nM (1/5 dilution) |
| Kasumi-1 | ATCC | 20% RPMI 1640 | 10 days | 0.32~1,000 nM (1/5 dilution) |
| MM.1S | ATCC | 10% RPMI 1640 | 11 days | 0.01~1,000 nM (1/10 dilution) |
| Mino | ATCC | 15% RPMI 1640 | 14 days | 0.1~10,000 nM (1/10 dilution) |

The results of Experimental Examples 1 and 2 are shown in Tables 6 and 7 below.

TABLE 6

| Compound No. | Enzyme inhibitory activity (IC$_{50}$, nM) | | Cell growth inhibitory activity (GI$_{50}$, nM) | |
|---|---|---|---|---|
| | EZH1 | EZH2 | KARPAS-422 (EZH2$^{Y641N}$ mutation) | Pfeiffer (EZH2$^{A677G}$ mutation) |
| 1 | 97.6 | 14.3 | — | — |
| 2 | 371 | 7.9 | — | — |
| 3 | — | — | 39 | — |
| 4 | 20 | 2.6 | 1.9~2.6 | — |
| 5 | 16 | 1.3 | 2.4 | — |
| 6 | — | — | 310 | — |
| 7 | 54 | 3.8 | 4.8 | — |
| 8 | 57 | 3.2 | 13 | — |
| 9 | 16~43 | 1.5~5.0 | 2.0~15 | 0.97 |
| 10 | 10~21 | 0.8~1.4 | 2.5~13 | 0.84 |
| 11 | >1,000 | 116~473 | 563~>1,000 | — |
| 12 | 23~50 | 3.2 | 4.9~15 | 0.66 |
| 13 | 23~35 | 1.8~2.3 | 1.8~9.6 | 0.27 |
| 14 | 27 | 3.2 | 50 | — |
| 15 | 65 | 3.6 | 18 | — |
| 16 | 89 | 11 | 68 | — |
| 17 | 74 | 5.6 | 52 | — |
| 18 | 47 | 4.3 | 16 | — |
| 19 | 45 | 4.4 | 440 | — |
| 20 | 48 | 3.7 | 18 | — |
| 21 | 137 | 7.2 | 75 | — |
| 22 | 180 | 16 | >1,000 | — |
| 23 | 68 | 4.4 | >1,000 | — |
| 24 | 34 | 3.0 | 62 | — |
| 25 | 166 | 11 | — | — |
| 26 | 85 | 6.2 | 99 | — |
| 27 | 310 | 3.9 | — | — |
| 28 | 55 | 3.2 | 14 | — |
| 29 | 136 | 5.0 | 51 | — |
| 30 | 190 | 3.4 | 307 | — |
| 31 | 51 | 3.8 | 231 | — |
| 32 | — | — | >1,000 | — |
| 33 | — | — | 187 | — |
| 34 | 9.7 | 1.4 | 3.2 | 1.48 |
| 35 | — | — | 57 | — |
| 36 | — | — | 87 | — |
| 37 | — | — | 22 | — |
| 38 | 54 | 4.4 | — | — |
| 39 | 9.7~30 | 1.2~6.2 | 3.2~8.4 | 0.76~0.99 |
| 40 | 28 | 1.8 | 1.8 | 0.71 |
| 41 | >1,000 | 69 | 69 | — |
| 42 | 31~34 | 3.4~6.0 | 2.6~8.8 | 0.97~1.41 |
| 43 | 8.1 | 1.4 | 58 | 6.76 |
| 44 | 34 | 0.4 | — | — |
| 45 | 18 | 6.2 | — | — |
| 46 | 16 | 9.7 | — | — |
| 47 | 20 | 7.0 | — | — |
| 48 | 2.6~40 | 0.4~2.6 | 3.7~12.4 | 0.77 |
| 49 | 7.0~16 | 0.35~1.4 | 1.2~9.7 | 0.21 |
| 50 | >1,000 | 205 | 419 | — |
| 51 | 41 | 1.6 | 4.4 | — |
| 52 | 32~55 | 3.4~3.7 | 4.4~9.7 | — |
| 53 | 27~139 | 4.5~9.1 | 5.1~14 | — |
| 54 | 41 | 6.4 | 19 | — |
| 55 | 26 | 5.6 | — | — |
| 56 | — | — | 11 | — |
| 57 | — | — | 13 | — |
| 58 | — | — | 13 | — |
| 59 | — | — | 28 | — |
| 60 | — | — | 28 | — |
| 61 | — | — | 4.8 | — |
| 62 | — | — | 6.2 | — |
| 63 | — | — | 4.4 | — |
| 64 | — | — | 5.0 | — |
| 65 | — | — | 8.8 | — |
| 66 | — | — | 6.4 | — |
| 67 | — | — | 4.3 | — |
| 68 | — | — | 5.1 | — |
| 69 | 65 | 2.7 | 10 | — |
| Control A | 83~197 | 2.0~2.9 | 19~77 | 1.93 |
| Control B | 17~46 | 1.0~2.0 | 1.3~15 | 0.57 |

TABLE 7

| Cell line | Cell growth inhibitory activity (GI$_{50}$, nM) | | |
|---|---|---|---|
| | Control A | Control B | Compound 49 |
| SU-DHL-4 | 281 | 21 | 11 |
| RS4;11 | 932 | 62 | 24 |
| MV4-11 | 220 | 6.1 | 3.9 |
| Kasumi-1 | >1,000 | 324 | 51 |
| MM.1S | 204 | 2.3 | 1.4 |
| RPMI8226 | 315 | 7.8 | 6.4 |
| KMS-11 | 554 | 25 | 8.1 |
| Mino | 225 | 2.5 | 2.0 |
| JeKo-1 | 3,582 | 71 | 42 |

Experimental Example 3: Test for Metabolic Stability in Liver Microsomes

In order to confirm the metabolic stability of the synthetic compounds in the liver, 5 µM test compound and 1 mg/mL human, dog, rat or mouse liver microsomes were allowed to react with each other at 37° C. in the presence of the NADPH regenerating system for 1 hour. After 1 hour, the reaction was terminated and the supernatant obtained by centrifugation was analyzed by HPLC. With the peak value obtained as the analysis result, the residual amount (%) was calculated using the following equation through the peak value of the test compound after 1 hour of the reaction versus the peak value of the test compound at 0 min.

Residual amount (%)=(peak value of test compound after 1 hour of reaction/peak value of test compound at 0 min)×100

The results of Experimental Example 3 are shown in Table 8 below.

TABLE 8

| Compound No. | Residual amount (%) of test compound after 1 hour of reaction | | | |
|---|---|---|---|---|
| | Human | Dog | Rat | Mouse |
| 4 | 84 | NT | NT | 79 |
| 5 | 89 | NT | NT | 78 |
| 9 | 57 | NT | NT | 56 |
| 10 | 79 | NT | NT | 55 |
| 11 | 37 | NT | NT | 70 |
| 12 | 57 | NT | NT | 61 |
| 13 | 82 | NT | NT | 79 |
| 34 | 66 | NT | NT | 100 |
| 39 | 62 | NT | NT | 80 |
| 40 | 82 | NT | NT | 84 |
| 41 | 53 | NT | NT | 63 |
| 42 | 74 | NT | NT | 88 |
| 43 | 52 | NT | NT | 61 |
| 48 | 54 | NT | NT | 52 |
| 49 | 67 | 74 | 84 | 52 |
| 50 | 35 | NT | NT | 54 |
| 51 | 70 | NT | NT | 64 |
| 52 | 62 | NT | NT | 61 |
| 53 | 67 | NT | NT | 85 |
| Control A | NA | 14 | NA | NA |
| Control B | 65 | 83 | 81 | 50 |

NT: not tested; NA: not applicable

Experimental Example 4: Mouse Pharmacokinetics

Pharmacokinetics of the synthetic compounds as EZH2 inhibitors in mice (ICR, 8-week-old, male) were tested.

The oral administration group was maintained in a fasting state from the day before the test to 4 hours after administration of the test compound. On the day of administration of the test compound, the weight of each animal was measured and each synthetic compound was formulated using a selected solvent based on 30 mg/kg (10 mL/kg). Each test compound was administered orally in a single dose, a certain amount of the blood was taken at a predetermined time, plasma was isolated therefrom, and the concentration of each test compound in the plasma was analyzed using LC-MS/MS (Waters UPLC H-Class/Xevo TQ; Waters, USA). Pharmacokinetic coefficients were calculated by a linear-log trapezoidal summation formula using a non-compartment analysis of the Phoenix™ WinNonlin (Certara, USA) program through the plasma concentration curve over time. The results of Experimental Example 4 are shown in Table 9.

TABLE 9

| Compound No. | Area under oral curve (AUC) (ng · hr/mL) | Half life T1/2 (hr) |
|---|---|---|
| 4 | 770 | NC |
| 9 | 14,942~16,449 | 2.4~2.3 |
| 13 | 1,036 | NC |
| 39 | 3,649 | NC |
| 48 | 17,296~18,676 | 2.8~3.2 |
| 49 | 9,963 | 2.9 |
| 50 | 12,239 | 2.5 |
| 51 | 1,523 | NC |
| Control A | 4,884 | 0.6 |
| Control B | 3,425~5,003 | NC~1.0 |

NC: not calculated

Comparative Example

Control A is N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (tazemetostat), the synthesis of which is described in Example No. 44 on page 220 of International Patent Publication No. WO2012/142504. Control A has the following structure:

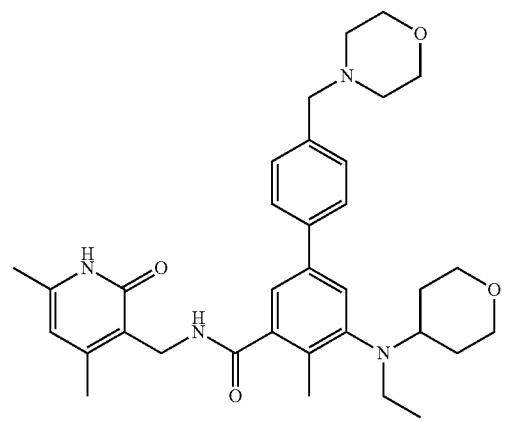 [SMILES: CCN(c1cc(-c2ccc(CN3CCOCC3)cc2)cc(C(=O)NCc2c(C)cc(C)[nH]c2=O)c1C)C1CCOCC1]

Control B is (2R)-7-chloro-2-[trans-4-(dimethylamino)cyclohexyl]-N-[(4,6-dimethyl-2-oxo-1,2-dihydropyridine)-3-yl)methyl]-2,4-dimethyl-1,3-benzodioxole-5-carboxamide (valemetostat), the synthesis of which is described in Example No. 35 on page 137 of International Patent Publication No. WO2015/141616. Control B has the following structure:

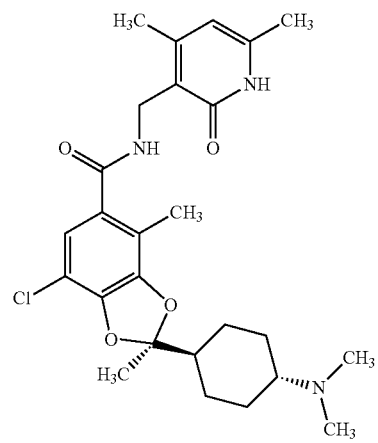 [SMILES: Cc1cc(C)c(CNC(=O)c2cc(Cl)c3c(c2C)O[C@@](C)([C@H]2CC[C@H](N(C)C)CC2)O3)c(=O)[nH]1]

Comparative Experimental Example: Tests for Inhibitory Activity Against EZH1/EZH2 Methyltransferase and for Inhibitory Activity Against Growth of Blood Cancer Cell Lines Control A [N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide (tazemetostat)] and control B [(2R)-7-chloro-2-[trans-4-(dimethylamino)cyclohexyl]-N-[(4,6-dimethyl-2-oxo-1,2-dihydropyridine)-3-yl)methyl]-2,4-dimethyl-1,3-benzodioxole-5-carboxamide (valemetostat)], synthesized according to the methods described in the Comparative Example, were tested for their inhibitory activities against EZH1/EZH2 methyltransferase and against the growth of blood cancer cell lines according to the same methods as described in Experimental Examples 1 and 2 above.

The results are shown in Tables 6 and 7 above.

As shown in Tables 6 and 7 above, it can be seen that the compounds according to the present disclosure have better inhibitory activity against EZH1 and/or EZH2 methyltransferase than control A or B, suggesting that these compounds have better inhibitory activity against the growth of blood cancer cell lines.

INDUSTRIAL APPLICABILITY

The present disclosure relates to novel heterotricyclic derivative compounds and the use thereof, and more particularly, to novel heterotricyclic derivative compounds having inhibitory activity against EZH1 (enhancer of zeste homolog 1) and/or EZH2 (enhancer of zeste homolog 2) activity, pharmaceutically acceptable salts thereof, or pharmaceutical compositions containing these compounds.

The invention claimed is:

1. A compound selected from among a heterotricyclic compound of the following Formula 1, a pharmaceutically acceptable salt thereof, an optical isomer thereof, and a hydrate thereof:

[Formula 1]

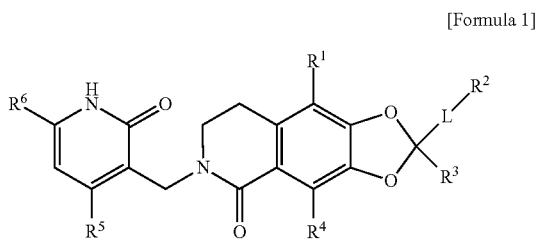

wherein:
$R^1$ is a 5- to 6-membered aromatic heterocyclyl containing 1 to 3 heteroatoms independently selected from the group consisting of N, O and S in a ring thereof, wherein the 5- to 6-membered aromatic heterocyclyl containing 1 to 3 heteroatoms independently selected from the group consisting of N, O and S in the ring thereof is unsubstituted or substituted with one to three independently selected from Group A below;
L is a bond, $C_{1-6}$ alkylene, or oxy ($C_{1-6}$)alkylene;
$R^2$ is $C_{3-6}$ cycloalkyl; substituted with $NR^{20}R^{21}$, wherein $R^{20}$ and $R^{21}$ are each independently H, formyl, $C_{1-6}$ alkyl, or substituted or unsubstituted $C_{1-6}$ alkylcarbonyl;
$R^3$ is $C_{1-6}$ alkyl;
$R^4$ is H, a halogen, or a $C_{1-6}$ alkyl containing 0 to 3 halogen atoms;
$R^5$ is $C_{1-6}$ alkyl or $C_{1-6}$ alkoxy;
$R^6$ is $C_{1-6}$ alkyl;
Group A comprises a halogen, $C_{1-6}$ alkyl, $C_{1-6}$ alkoxy, and a 5 to 6-membered aliphatic heterocyclyl containing 1 or 2 heteroatoms independently selected from the group consisting of N, O and S in a ring thereof, wherein the $C_{1-6}$ alkyl, the $C_{1-6}$ alkoxy and the 5 to 6-membered aliphatic heterocyclyl are unsubstituted or substituted with one to three independently selected from Group B below; and
Group B comprises a halogen, $C_{1-6}$ alkyl, and a 5 to 6-membered aliphatic heterocyclyl containing 1 or 2 heteroatoms independently selected from the group consisting of N, O and S in a ring thereof.

2. The compound of claim 1, wherein
$R^2$ is $C_{3-6}$ cycloalkyl substituted with amino, $C_{1-6}$ alkylamino, or di($C_{1-6}$)alkylamino.

3. The compound of claim 2, wherein
L is a bond or methylene;
$C_{3-6}$ cycloalkyl of $R^2$ is cyclobutyl, cyclopentyl, or cyclohexyl; and
$R^3$ is methyl, wherein the cyclobutyl, cyclopentyl, or cyclohexyl is unsubstituted or substituted with one independently selected from the group consisting of methyl, ethyl, ethylsulfonyl, hydroxy, methoxy, amino, methylamino, ethylamino, dimethylamino, diethylamino, ethylmethylamino, piperidyl, pyrrolidyl, trifluoroethyl, and (R)-2-hydroxybutanamide.

4. The compound of claim 1, wherein
L is a bond;
$R^4$ is H, a halogen, or methyl; and
$R^3$, $R^5$ and $R^6$ are methyl.

5. The compound of claim 1, wherein the heterotricyclic compound of Formula 1 is selected from the group consisting of the following compounds:
6-((4,6-dimethyl-2-oxo-1,2-dihydropyridin-3-yl)methyl)-2-(trans-4-(dimethylamino)cyclohexyl)-9-(furan-2-yl)-2,4-dimethyl-7,8-dihydro-[1,3]dioxolo[4,5-g]isoquinolin-5 (6H)-one;
9-(3,6-dihydro-2H-pyran-4-yl)-6-((4,6-dimethyl-2-oxo-1,2-dihydropyridin-3-yl)methyl)-2-(trans-4-(dimethylamino)cyclohexyl)-2,4-dimethyl-7,8-dihydro-[1,3]dioxolo[4,5-g]isoquinolin-5 (6H)-one;
6-((4,6-dimethyl-2-oxo-1,2-dihydropyridin-3-yl)methyl)-2-(trans-4-(dimethylamino)cyclohexyl)-2,4-dimethyl-9-(pyridin-3-yl)-7,8-dihydro-[1,3]dioxolo[4,5-g]isoquinolin-5 (6H)-one;
6-((4,6-dimethyl-2-oxo-1,2-dihydropyridin-3-yl)methyl)-2-(trans-4-(dimethylamino)cyclohexyl)-2,4-dimethyl-9-(thiazol-5-yl)-7,8-dihydro-[1,3]dioxolo[4,5-g]isoquinolin-5 (6H)-one; and
6-((4,6-dimethyl-2-oxo-1,2-dihydropyridin-3-yl)methyl)-2-(trans-4-(dimethylamino)cyclohexyl)-2,4-dimethyl-9-(1-methyl-1H-pyrazol-4-yl)-7,8-dihydro-[1,3]dioxolo[4,5-g]isoquinolin-5 (6H)-one.

6. A pharmaceutical composition comprising, as an active ingredient, the compound of claim 1.

7. The pharmaceutical composition of claim 6, which is in the form of tablets, pills, powders, capsules, syrups or emulsions.

8. A pharmaceutical composition comprising, as an active ingredient, the compound of claim 2.

9. A pharmaceutical composition comprising, as an active ingredient, the compound of claim 3.

10. A pharmaceutical composition comprising, as an active ingredient, the compound of claim 4.

11. A pharmaceutical composition comprising, as an active ingredient, the compound of claim 5.

12. A method for treating cancer or tumor in a subject in need thereof, comprising administering an effective amount of a composition comprising the compound of claim 1 to the subject, wherein the cancer or tumor is associated with an increased enzymatic activity of EZH1 (enhancer of zeste homolog 1) and/or EZH2 (enhancer of zeste homolog 2).

* * * * *